(12) United States Patent
Luzzio et al.

(10) Patent No.: US 11,530,207 B2
(45) Date of Patent: Dec. 20, 2022

(54) COMPOUNDS FOR THE TREATMENT OF CANCER

(71) Applicant: SKYHAWK THERAPEUTICS, INC., Waltham, MA (US)

(72) Inventors: Michael Luzzio, Waltham, MA (US); Kathleen McCarthy, Waltham, MA (US)

(73) Assignee: SKYHAWK THERAPEUTICS, INC., Waltham, MA (US)

( * ) Notice: Subject to any disclaimer, the term of this patent is extended or adjusted under 35 U.S.C. 154(b) by 45 days.

(21) Appl. No.: 17/046,245

(22) PCT Filed: Apr. 10, 2019

(86) PCT No.: PCT/US2019/026788
§ 371 (c)(1),
(2) Date: Oct. 8, 2020

(87) PCT Pub. No.: WO2019/199972
PCT Pub. Date: Oct. 17, 2019

(65) Prior Publication Data
US 2021/0292316 A1    Sep. 23, 2021

Related U.S. Application Data

(60) Provisional application No. 62/655,431, filed on Apr. 10, 2018.

(51) Int. Cl.
| | | |
|---|---|---|
| C07D 451/02 | (2006.01) | |
| C07D 451/04 | (2006.01) | |
| C07D 451/14 | (2006.01) | |
| A61K 31/501 | (2006.01) | |
| A61K 45/06 | (2006.01) | |

(52) U.S. Cl.
CPC ........... *C07D 451/14* (2013.01); *A61K 45/06* (2013.01); *C07D 451/04* (2013.01)

(58) Field of Classification Search
CPC .. C07D 451/02; C07D 451/04; C07D 451/14; A61K 31/501
See application file for complete search history.

(56) References Cited

U.S. PATENT DOCUMENTS

| | | |
|---|---|---|
| 4,873,192 A | 10/1989 | Kunkel |
| 7,291,737 B2 | 11/2007 | Kuhar et al. |
| 9,956,223 B2 | 5/2018 | Ebeling et al. |
| 2004/0229864 A1 | 11/2004 | Bourrain et al. |
| 2008/0275048 A1 | 11/2008 | Frost et al. |
| 2009/0247530 A1 | 10/2009 | Nolte et al. |
| 2018/0170923 A1 | 6/2018 | Metzger et al. |
| 2018/0344737 A1 | 12/2018 | Ebeling et al. |

FOREIGN PATENT DOCUMENTS

| | | |
|---|---|---|
| WO | WO-2006045716 A1 | 5/2006 |
| WO | WO-2007103694 A2 | 9/2007 |
| WO | WO-2017100726 A1 | 6/2017 |
| WO | WO-2019028440 A1 | 2/2019 |
| WO | WO-2019060917 A2 | 3/2019 |

OTHER PUBLICATIONS

Agrawal, et al., Targeting splicing abnormalities in cancer, Curr Opin Genet Dev., Feb. 2018;48:67-74. doi: 10.1016/j.gde.2017.10.010. Epub Nov. 12, 2017. PMID: 29136527.
Almada et al., "Promoter directionality is controlled by U1 snRNP and polyadenylation signals", Nature, Jul. 18, 2013, vol. 499, pp. 360-363.
Bertram K, et al., Cryo-EM structure of a human spliceosome activated for step 2 of splicing, Nature. Feb. 16, 2017;542(7641):318-323. doi: 10.1038/nature21079. Epub Jan. 11, 2017. PMID: 28076346.
Bertram K, et al., Cryo-EM Structure of a Pre-catalytic Human Spliceosome Primed for Activation, Cell. Aug. 10, 2017;170(4):701-713.e11. doi:10.1016/j.cell.2017.07.011. Epub Aug. 3, 2017. PMID: 28781166.
Birman et al., "Second-harmonic generation-based methods to detect and characterize ligand-induced RNA conformational changes", Methods, Sep. 2019, vol. 167, pp. 92-104.
Boutz, et al. Detained introns are a novel, widespread class of post-transcriptionally spliced introns. Genes Dev. Jan. 1, 2015;29(1):63-80. doi: 10.1101/gad.247361.114.
Braun et al., "Coordinated Splicing of Regulatory Detained Introns within Oncogenic Transcripts Creates and Exploitable Vulnerability in Malignant Glioma", Cancer Cell, 2017, vol. 32, pp. 411-426.
Butko et al., "Detection of Ligand-Induced Conformational Changes in Oligonucleotides by Second-Harmonic Generation at a Supported Lipid Bilayer Interface", Anal. Chem., 2016, vol. 88, p. 10482-10489.
Cheng et al., "Probes and drugs that interfere with protein translation via targeting to the RNAs or RNA-protein interactions", Methods, 2019, vol. 167, pp. 124-133.
Cheung et al., Discovery of Small Molecule Splicing Modulators of Survival Motor Neuron-2 (SMN2) for the Treatment of Spinal Muscular Atrophy (SMA), J Med Chem., Dec. 27, 2018;61(24):11021-11036. doi: 10.1021/acs.jmedchem.8b01291. Epub Dec. 13, 2018. PMID: 30407821.
Clark et al., "Long-read sequencing reveals the splicing profile of the calcium channel gene CACNA1C in human brain", bioRxiv 260562; pp. 1-19, doi: https://doi.org/10.1101/260562.
Clery et al., "switchSENSE: A new technology to study protein-RNA interactions", Methods, Apr. 2017, vol. 118-119, pp. 137-145.
Cooper, Thomas A., "Use of minigene systems to dissect alternative splicing elements", Methods, Dec. 2005, vol. 37, Issue 4, pp. 331-340.
Cretu C, et al., Structural Basis of Splicing Modulation by Antitumor Macrolide Compounds, Mol Cell. Apr. 19, 2018;70(2):265-273.e8.doi:10.1016/j.molcel.2018.03.011. Epub Apr. 12, 2018. PMID: 29656923.

(Continued)

*Primary Examiner* — Bruck Kifle
(74) *Attorney, Agent, or Firm* — Wilson Sonsini Goodrich & Rosati

(57) ABSTRACT

Described herein are splice modifying compounds affecting splicing of mRNA, such as pre-mRNA, expressed from the FOXM1 gene, compositions comprising thereof, and methods using the same.

20 Claims, 23 Drawing Sheets

Specification includes a Sequence Listing.

(56) References Cited

OTHER PUBLICATIONS

Czech, Christian et al., Biomarker for Spinal Muscular Atrophy: Expression of SMN in Peripheral Blood of SMA Patients and Healthy Controls, PloS one vol. 10,10 e0139950. Oct. 15, 2015, doi:10.1371/journal.pone.0139950.
Fica, Sebastian M, and Kiyoshi Nagai, Cryo-electron microscopy snapshots of the spliceosome: structural insights into a dynamic ribonucleoprotein machine, Nature structural & molecular biology vol. 24,10 (2017): 791-799. doi:10.1038/nsmb.3463.
Finci, Lorenzo I et al., The cryo-EM structure of the SF3b spliceosome complex bound to a splicing modulator reveals a pre-mRNA substrate competitive mechanism of action, Genes& development vol. 32,3-4 (2018): 309-320. doi:10.1101/gad.311043.117.
Henderson et al., "Generation of small molecule-binding RNA arrays and their application to fluorogen-binding RNA aptamers", Methods, 2019, vol. 167, pp. 39-53.
Hermann T, Patel DJ, RNA bulges as architectural and recognition motifs, Structure.Mar. 15, 2000;8(3):R47-54. doi: 10.1016/S0969-2126(00)00110-6. PMID: 10745015.
Hug, Nele et al. , Mechanism and regulation of the nonsense-mediated decay pathway, Nucleic acids research vol. 44,4 (2016): 1483-95. doi:10.1093/nar/gkw010.
Kastner B, et al., Structural Insights into Nuclear pre-mRNA Splicing in Higher Eukaryotes, Cold Spring Harb Perspect Biol. Nov. 1, 2019;11(11):a032417. doi:10.1101/cshperspect.a032417. PMID: 30765414; PMCID: PMC6824238.
Kletzl et al., "The oral splicing modifier RG7800 increases full length survival of motor neuron 2 mRNA and survival of motor neuron protein: Results from trials in healthy adults and patients with spinal and muscular atrophy", Neuromuscular Disorders, 2019, vol. 29, Issue 1, pp. 21-29.
Knezevic et al., "Quantitation of Affinity, Avidity, and Binding Kinetics of Protein Analytes with a Dynamically Switchable Biosurface", J. Am. Chem. Soc., 2012, vol. 134, pp. 15225-15228.
Kondo, Yasushi et al., Crystal structure of human U1 snRNP, a small nuclear ribonucleoprotein particle, reveals the mechanism of 5' splice site recognition, eLife vol. 4 e04986. Jan. 2, 2015, doi:10.7554/eLife.04986.
Korver et al.: The winged-helix transcription factor Trident is expressed in cycling cells. Nucleic Acids Res. 25(9):1715-1719 (1997).
Lee et al., "Mechanisms and Regulation of Alternative Pre-mRNA Splicing", Annual Review of Biochemistry, 2015, vol. 84, pp. 291-323.
Li et al., "Annotation-free quantification of RNA splicing using LeafCutter", Nat Genet., Jan. 2018, vol. 50, No. 1, pp. 151-158. doi:10.1038/s41588-017-0004-9.
Li, Xueni et al., CryoEM structure of *Saccharomyces cerevisiae* U1 snRNP offers insight into alternative splicing, Nature communications vol. 8,1 1035. Oct. 19, 2017, doi:10.1038/s41467-017-01241-9.
Liu et al.: FoxM1B is overexpressed in human glioblastomas and critically regulates the tumorigenicity of glioma cells. Cancer Res. 66(7):3593-3602 (2006).
Martin et al., "Using SHAPE-MaP to probe small molecule-RNA interactions", Methods, Sep. 2019, vol. 167, pp. 105-116.
Mashalidis et al., "A three-stage biophysical screening cascade for fragment-based drug discovery", Nature Protocols, 2013, vol. 8, No. 11 pp. 2309-2324.
McGovern-Gooch et al., "Fluorescence-based investigations of RNA-small molecule interactions", Methods, Sep. 2019, vol. 167, pp. 54-65, doi: 10.1016/j.ymeth.2019.05.017.
Montes, Matias et al., RNA Splicing and Disease: Animal Models to Therapies, Trends in genetics : TIG vol. 35,1 (2019): 68-87. doi:10.1016/j.tig.2018.10.002.
Murata et al., "Modulating RNA secondary and tertiary structures by mismatch binding ligands", Methods, 2019, vol. 167, pp. 78-91.

Muto Y, et al., The structure and biochemical properties of the human spliceosomal protein U1C, J Mol Biol. Jul. 30, 2004;341(1):185-98. doi: 10.1016/j.jmb.2004.04.078. PMID:15312772.
Nakamura et al.: Genome-wide cDNA microarray analysis of gene expression profiles in pancreatic cancers using populations of tumor cells and normal ductal epithelial cells selected for purity by laser microdissection. Oncogene 23(13):2385-2400 (2004).
Nelissen, R L et al., Zinc finger-like structure in U1-specific protein C is essential for specific binding to U1 snRNP, Nucleic acids research vol. 19,3 (1991): 449-54.doi:10.1093/nar/19.3.449.
Palacino J, et al., SMN2 splice modulators enhance U1-pre-mRNA association and rescue SMA mice, Nat Chem Biol. Jul. 2015;11(7):511-7. doi:10.1038/nchembio.1837. Epub Jun. 1, 2015. Erratum in: Nat Chem Biol. Sep. 2015;11(9):741. Erratum in: Nat Chem Biol. Apr. 2016; 12(4):304. PMID: 26030728.
Parra et al., "An important class of intron retention events in human erythroblasts is regulated by cryptic exons proposed to function as splicing decoys", RNA, 24(9):1255-1265, Cold Spring Harbor Press Laboratory for the RNA Society.
PCT/US2019/026788 International Search Report and Written Opinion dated Aug. 19, 2019.
Pilarsky et al.: Identification and validation of commonly overexpressed genes in solid tumors by comparison of microarray data. Neoplasia 6(6):744-750 (2004).
Pinard E, et al., Discovery of a Novel Class of Survival Motor Neuron 2 Splicing Modifiers forthe Treatment of Spinal Muscular Atrophy, J Med Chem. May 25, 2017;60(10):4444-4457. doi:10.1021/acs.jmedchem.7b00406. Epub May 4, 2017. PMID: 28441483.
Plaschka C, Newman AJ, Nagai K., Structural Basis of Nuclear pre-mRNA Splicing: Lessons from Yeast, Cold Spring Harb Perspect Biol. May 1, 2019 ;11(5):a032391. doi:10.1101/cshperspect.a032391. PMID: 30765413; PMCID: PMC6496352.
Poirier, Agnès et al., Risdiplam distributes and increases SMN protein in both the central nervous system and peripheral organs, Pharmacology research & perspectives vol. 6,6 e00447. Nov. 29, 2018, doi:10.1002/prp2.447.
Ratni et al., "Rewriting the (tran)script: Application to spinal muscular atrophy", Progress in Medicinal Chemistry, 2019, vol. 58, pp. 119-156.
Ratni H, et al., Discovery of Risdiplam, a Selective Survival of Motor Neuron-2 ( SMN2) Gene Splicing Modifier for the Treatment of Spinal Muscular Atrophy (SMA), J Med Chem. Aug. 9, 2018;61(15):6501-6517. doi: 10.1021/acs.jmedchem.8b00741. Epub Jul. 25, 2018.PMID: 30044619.
Ratni H, et al., Specific Correction of Alternative Survival Motor Neuron 2 Splicing by Small Molecules: Discovery of a Potential Novel Medicine to Treat Spinal Muscular Atrophy, J Med Chem. Jul. 14, 2016;59(13):6086-100. doi:10.1021/acs.jmedchem.6b00459. Epub Jul. 6, 2016. PMID: 27299419.
Rizvi et al., "Discovery of Selective RNA-Binding Small Molecules by Affinity-Selection Mass Spectrometry", ACS Chem Biol., 2018, vol. 13, No. 3, pp. 820-831.
Rizvi et al., "RNA-ALIS: Methodology for screening soluble RNAs as small molecule targets using ALIS affinity-selection mass spectrometry", Methods, Sep. 1, 2019, vol. 167, pp. 28-38.
Roca, Xavier et al., Widespread recognition of 5' splice sites by noncanonical base-pairing to U1snRNA involving bulged nucleotides, Genes & development vol. 26,10 (2012):1098-109. doi:10.1101/gad.190173.112.
Romero-Barrios, Natali et al., Splicing regulation by long noncoding RNAs, Nucleic acids research vol. 46,5 (2018): 2169-2184. doi:10.1093/nar/gky095.
Rosenberg et al., "Learning the Sequence Determinants of Alternative Splicing from Millions of Random Sequences", Cell, 2015, vol. 163, pp. 698-711.
Sco I 11 et al., "RNA mis-splicing in disease", Nat Rev Genet., Jan. 2016, vol. 17, No. 1, pp. 19-32, doi: 10.1038/nrg.2015.3.
Shi Y., The Spliceosome: A Protein-Directed Metalloribozyme, J MolBiol. Aug. 18, 2017;429(17):2640-2653. doi: 10.1016/j.jmb.2017.07.010. Epub Jul. 19, 2017. PMID: 28733144.
Sibley, Christopher R et al., Lessons from non-canonical splicing,Nature reviews. Genetics vol. 17,7 (2016): 407-421. doi:10.1038/nrg.2016.46.

(56) References Cited

OTHER PUBLICATIONS

Silvers et al., "Differential Scanning Fluorimetry for Monitoring RNA Stability", ChemBioChem, May 4, 2015, vol. 16, No. 7, pp. 1109-1114.
Smola et al., "Selective 2'-hydroxyl acylation analyzed by primer extension and mutational profiling (SHAPE-MaP) for direct, versatile, and accurate RNA structure analysis", Nat Protoc., Nov. 2015, vol. 10, No. 11, pp. 1643-1669. doi:10.1038/nprot.2015.103.
Spraggon et al., "U1 snRNP-Dependent Suppression of Polyadenylation: Physiological Role and Therapeutic Opportunities in Cancer", International Journal of Cell Biology, 2013, vol. 2013, Article ID 846510, pp. 1-10, doi.org/10.1155/2013/846510.
Sturm, Stefan et al., A phase 1 healthy male volunteer single escalating dose study of the pharmacokinetics and pharmacodynamics of risdiplam(RG7916, RO7034067), a SMN2 splicing modifier, British journal of clinical pharmacology vol. 85,1 (2019): 181-193. doi:10.1111/bcp.13786.
Taladriz-Sender et al., "Splice-switching small molecules: A new therapeutic approach to modulate gene expression", Methods, Sep. 2019, vol. 167, pp. 134-142, doi: 10.1016/j.ymeth.2019.06.011.
Tan et al., Noncanonical registers and base pairs in human 5' splice-site selection, Nucleic Acids Research, 2016, vol. 44, No. 8, pp. 3908-3921. doi:10.1093/nar/gkw163.
Teh et al.: FOXM1 is a downstream target of Gli1 in basal cell carcinomas. Cancer Res 62(16):4773-4780 (2002).
Teng, Teng et al. ,Splicing modulators act at the branch point adenosine binding pocket defined by the PHF5A-SF3b complex, Nature communications vol. 8 15522. May 25, 2017,doi: 10.1038/ncomms15522.
Thompson et al., "NMR characterization of RNA small molecule interactions", Methods, 2019, vol. 167, pp. 66-77.
Tilgner et al., "Comprehensive transcriptome analysis using synthetic long-read sequencing reveals molecular co-association of distant splicing events", Nat Biotechnol., Jul. 2015, vol. 33, No. 7, pp. 736-742, doi: 10.1038/nbt.3242.
Treutlein et al., "Cartography of neurexin alternative splicing mapped by single-molecule long-read mRNA sequencing", PNAS, Apr. 1, 2014, 111 (13) E1291-E1299.
Van Nostrand et al., "Robust transcriptosome-wide discovery of RNA binding protein binding sites with enhanced CLIP (eCLIP)", Nat Methods, Jun. 2016, vol. 13, No. 6, pp. 508-514. doi:10.1038/nmeth.3810.
Vaquero-Garcia et al., "A new view of transcriptome complexity and regulation through the lens of local splicing variations", eLife, 2016, 5:e11752, pp. 1-30, DOI: 10.7554/eLife.11752.
Verbist et al., "Using transcriptomics to guide lead optimization in drug discovery projects: Lessons learned from the QSTAR project", Drug Discovery Today, May 2015, vol. 20, No. 5, pp. 505-513.
Vo et al., "Biosensor-surface plasmon resonance: A strategy to help establish a new generation of RNA-specific small molecules", Methods, 2019, vol. 167, pp. 15-27.
Wahl MC, Will CL, Luhrmann R, The spliceosome: design principles of a dynamic RNP machine, Cell. Feb. 20, 2009;136(4):701-18. doi:10.1016/j.cell.2009.02.009. PMID: 19239890.
Wan R, et al., Structure of an Intron Lariat Spliceosome from *Saccharomyces cerevisiae*, Cell. Sep. 21, 2017;171(1):120-132.e12. doi:10.1016/j.cell.2017.08.029. Epub Sep. 14, 2017. PMID: 28919079.
Wang et al.: The Forkhead Box m1b transcription factor is essential for hepatocyte DNA replication and mitosis during mouse liver regeneration. PNAS USA 99(26):16881-16886 (2002).
Weber, Gert et al., Functional organization of the Sm core in the crystal structure of human U1 snRNP, The EMBO journal vol. 29,24 (2010): 4172-84. doi:10.1038/emboj.2010.295.
Wicks et al., "Fluorescent indicator displacement assays to identify and characterize small molecule interactions with RNA", Methods, 2019, vol. 167, pp. 3-14.
Will, Cindy L, and Reinhard Luhrmann, Spliceosome structure and function, Cold Spring Harbor perspectives in biology vol. 3,7 a003707. Jul. 1, 2011, doi:10.1101/cshperspect.a003707.
Wong et al., "Quantitative Activity Profile and Context Dependence of All Human 5' Splice Sites", Molecular Cell, May 2018, vol. 71, pp. 1012-1026.
Yan, Chuangye et al. , Molecular Mechanisms of pre-mRNA Splicing through Structural Biology of the Spliceosome, Cold Spring Harbor perspectives in biology vol. 11,1 a032409. Jan. 2, 2019,doi:10.1101/cshperspect.a032409.
Yan et al., "miRNA inhibition by proximity-enabled Dicer inactivation", Methods, 2019, vol. 167, pp. 117-123.
Ye et al., "DRUG-seq for miniaturized high-throughput transcriptome profiling in drug discovery", Nature Communications, 2018, 9:4307, pp. 1-9, doi.org/10.1038/S41467-018-06500-x.
Ye et al.: Hepatocyte nuclear factor 3/fork head homolog 11 is expressed in proliferating epithelial and mesenchymal cells of embryonic and adult tissues. Mol Cell Biol. 17(3):1626-1641 (1997).
Zaworski, Phillip et al., SMN Protein Can Be Reliably Measured in Whole Blood with an Electrochemiluminescence (ECL) Immunoassay: Implications for Clinical Trials, PloS one vol. 11,3e0150640. Mar. 8, 2016, doi:10.1371/journal.pone.0150640.
Zubradt et al., "DMS-MaPseq for genome-wide or targeted RNA structure probing in vivo", Nat Methods, Jan. 2017, vol. 14, No. 1, pp. 75-82. doi:10.1038/nmeth.4057.

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acaggtggtg tttggttaca                                               20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaattaaaca agctggtgat ggg                                           23

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gtggcgatct gcgaga                                                   16

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagcttgccc gccatag                                                  17

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctggtcctgc agaagaaaga g                                             21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ccaaggtgct gctagctgag ga    22

<210> SEQ ID NO 7
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ggctagcctc gagaattcgt ttttggggaa caggtggtgt ttggttacat gagtaagttc    60
tttagtggcg atctgcgaga ttttggtaca cccatcacca gcttgtttaa ttttatctttt  120
ctttgtttat cagcggccgc ttcccttttag    150

<210> SEQ ID NO 8
<211> LENGTH: 1031
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ggctagcctc gagaattcgg cggaagatga agccactgct accacgggtc agctcatacc    60
tggtacctat ccagttcccg gtgaaccagt cactggtgtt gcagccctcg gtgaaggtgc   120
cattgcccct ggcggcttcc ctcatgagct cagagcttgc ccgccatagc aagcgagtcc   180
gcattgcccc caaggtgctg ctagctgagg aggggatagc tcctctttct tctgcaggac   240
cagggaaaga ggagaaactc ctgtttggag aagggttttc tcctttgctt ccagttcaga   300
ctatcaagga ggaagaaatc cagcctgggg aggaaatgcc acacttagcg agacccatca   360
aagtggagag ccctcccttg gaagagtggc cctccccggc cccatctttc aaagaggaat   420
catctcactc ctgggaggat tcgtcccaat ctcccacccc aagacccaag aagtcctaca   480
gtgggcttag gtccccaacc cggtgtgtct cggaaatgct tgtgattcaa cacagggaga   540
ggagggagag gagccggtct cggaggaaac agcatctact gcctccctgt gtggatgagc   600
cggagctgct cttctcagag gggcccagta cttcccgctg ggccgcagag ctcccgttcc   660
cagcagactc ctctgacccct gcctcccagc tcagctactc ccaggaagtg ggaggacctt   720
ttaagacacc cattaaggaa acgctgccca tctcctccac cccgagcaaa tctgtcctcc   780
ccagaacccc tgaatcctgg aggctcacgc ccccagccaa agtaggggga ctggatttca   840
gcccagtaca aacctcccag ggtgcctctg accccttgcc tgaccccctg gggctgatgg   900
atctcagcac cactcccttg caaagtgctc ccccccttga atcaccgcaa aggctcctca   960
gttcagaacc cttagacctc atctccgtcc cctttggcaa ctcttctccc tcagcggccg  1020
cttccctttag  1031

<210> SEQ ID NO 9
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

| | |
|---|---|
| ggctagcctc gagaattcgg ccaggctcgt gccgttttgc agacgccacc gccgaggaaa | 60 |
| accgtgtact attagccatg gtcaaccca ccgtgttctt cgacattgcc gtcgacggcg | 120 |
| agcccttggg ccgcgtctcc tttgagctgt ttgcagacaa ggtcccaaag acagcagaaa | 180 |
| attttcgtgc tctgagcact ggagagaaag gatttggtta taagggttcc tgctttcaca | 240 |
| gaattattcc agggtttatg tgtcagggtg gtgacttcac acgccataat ggcactggtg | 300 |
| gcaagtccat ctatggggag aaatttgaag atgagaactt catcctaaag catacgggtc | 360 |
| ctggcatctt gtccatggca aatgctggac ccaacacaaa tggttccgc ggccgcttcc | 420 |
| ctttag | 426 |

COMPOUNDS FOR THE TREATMENT OF CANCER

CROSS REFERENCE

This application is a national phase entry of PCT/US19/26788, filed Apr. 10, 2019, which claims priority to U.S. Provisional Application No. 62/655,431, filed Apr. 10, 2018, each of which is incorporated herein by reference in its entirety.

BACKGROUND

The majority of protein-coding genes in the human genome are composed of multiple exons (coding regions) that are separated by introns (non-coding regions). Gene expression results in a single precursor messenger RNA (pre-mRNA). The intron sequences are subsequently removed from the pre-mRNA by a process called splicing, which results in the mature messenger RNA (mRNA). By including different combinations of exons, alternative splicing gives rise to multiple mRNAs encoding distinct protein isoforms. The spliceosome, an intracellular complex of multiple proteins and ribonucleoproteins, catalyzes splicing.

Current therapeutic approaches to direct and control mRNA expression require methods such as gene therapy, genome editing, or a wide range of oligonucleotide technologies (antisense, RNAi, etc.). Gene therapy and genome editing act upstream of transcription of mRNA by influencing the DNA code and thereby changing mRNA expression. Oligonucleotides modulate the action of RNA via canonical base/base hybridization. The appeal of this approach is in the design of the basic pharmacophore of an oligonucleotide, which can be defined in a straightforward fashion by known base pairing to the target sequence subject. Each of these therapeutic modalities suffers from substantial technical, clinical, and regulatory challenges. Some limitations of oligonucleotides as therapeutics (e.g., antisense, RNAi) include unfavorable pharmacokinetics, lack of oral bioavailability, and lack of blood-brain-barrier penetration, with the latter precluding delivery to the brain or spinal cord after parenteral drug administration for the treatment of diseases (e.g., neurological diseases, brain cancers). In addition, oligonucleotides are not taken up effectively into solid tumors without a complex delivery system such as lipid nanoparticles. Further, most of the oligonucleotides taken up into cells and tissues remain in nonfunctional compartments (e.g., endosomes) and does not gain access to the cytosol and/or nucleus where the target is located Additionally, to anneal to a target, oligonucleotide therapies require access to complementary base pairs of the target. This approach assumes that pre-mRNA sequences exist as a linear strand of RNA in the cell. However, pre-mRNA is rarely linear; it has complex secondary and tertiary structure. Further, cis-acting elements (e.g., protein binding elements) and trans-acting factors (e.g., splicing complex components) can create additional two-dimensional and three-dimensional complexity (e.g., by binding to the pre-mRNA). These features can be potency- and efficacy-limiting for oligonucleotide therapies.

SUMMARY

The novel small molecule splicing modulators (SMSMs) described herein do not suffer from the limitations above, nor the structural and steric hindrances that greatly limit oligonucleotide therapies (e.g., by blocking hybridization to pre-mRNA targets). Small molecules have been essential in uncovering the mechanisms, regulations, and functions of many cellular processes, including DNA replication, transcription, and translation. While several recent reports have described screens for small molecule effectors of splicing, only a small number of constitutive or alternative splicing modulators have been identified and many of the small-molecule inhibitors lack specificity, lack selectivity, lack potency, exhibit toxicity, or are not orally available. Targeting the RNA transcriptome with small-molecule modulators represents an untapped therapeutic approach to treat a variety of RNA-mediated diseases. Accordingly, there remains a need to develop small-molecule RNA modulators useful as therapeutic agents. There is need in the art for novel modulators of splicing or splicing-dependent processes. Provided herein are small molecule splicing modulators and uses thereof that fulfill this need.

In one aspect, the splice modifying compounds described herein have the structure of Formula (I), or a pharmaceutically acceptable salt or solvate thereof:

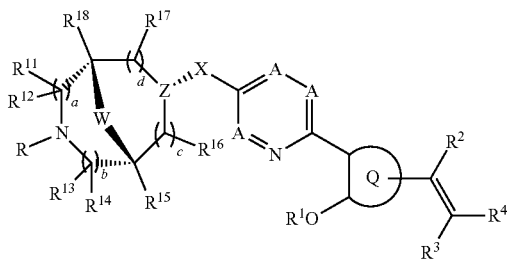

Formula (I)

wherein,
each A is independently N or $CR^4$;
each $R^4$ is independently selected from H, D, halogen, —CN, —OH, —$OR^5$, =O, =N—$OR^5$, —$SR^5$, —S(=O)$R^5$, —S(=O)$_2R^5$, —S(=O)(=$NR^5$)$R^5$, —N($R^5$)$_2$, —$NR^5$S(=O)(=$NR^5$)$R^6$, —$NR^5$S(=O)$_2R^6$, —S(=O)$_2$N($R^5$)$_2$, —C(=O)$R^5$, —OC(=O)$R^5$, —C(=O)$OR^5$, —OC(=O)$OR^5$, —C(=O)N($R^5$)$_2$, —OC(=O)N($R^5$)$_2$, —$NR^5$C(=O)$R^5$, —P(=O)($R^6$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, and substituted or unsubstituted monocyclic heteroaryl;
ring Q is substituted monocyclic aryl or substituted monocyclic heteroaryl;
X is absent, —O—, —$NR^7$—, —$CR^8R^9$—, —C(=O)—, —C(=C($R^6$)$_2$)—, —$CR^6$=$CR^6$—, —S—, —S(=O)—, —S(=O)$_2$—, or —S(=O)(=$NR^5$)—;
each $R^1$ and $R^5$ is independently H, D, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl;
each $R^2$ and $R^3$ is independently H, D, halogen, substituted or unsubstituted $C_1$-$C_6$alkyl, substituted or unsubstituted $C_1$-$C_6$haloalkyl, substituted or unsubstituted aryl, substituted or unsubstituted monocyclic heteroaryl, —OR$^5$, —N(R$^5$)$_2$, —CH$_2$OR$^5$, —C(=O)R$^5$, —C(=O)OR$^5$, —C(=O)N(R$^5$)$_2$, —S(=O)R$^5$, —S(=O)$_2$R$^5$, or —NR$^5$C(=O)R$^5$;

R$^4$ is —C(=O)R$^5$, —C(=O)OR$^5$, —C(=O)N(R$^6$)$_2$, —C=(O)N(OR$^5$)(R$^5$), —P(=O)(R$^6$)$_2$, —P(=O)(R$^6$)N(R$^6$)$_2$, —S(=O)R$^6$, —S(=O)$_2$R$^6$, —S(=O)(=NR$^5$)R$^5$, —N(R$^6$)C(=O)R$^6$, N(R$^6$)S(=O)R$^6$, N(R$^6$)S(=O)$_2$R$^6$, —C(=O)N(R$^6$)S(=O)$_2$R$^6$, —N(R$^6$)C(=O)N(R$^6$)$_2$, substituted or unsubstituted cycloalkyl, substituted or unsubstituted heterocycloalkyl, substituted or unsubstituted aryl, or substituted or unsubstituted heteroaryl;

each R$^6$ is independently H, D, substituted or unsubstituted C$_1$-C$_6$alkyl, substituted or unsubstituted C$_1$-C$_6$haloalkyl, substituted or unsubstituted aryl, substituted or unsubstituted monocyclic heteroaryl, —OR$^5$, —N(R$^5$)$_2$, —CH$_2$OR$^5$, —C(=O)R$^5$, —C(=O)OR$^5$, —C(=O)N(R$^5$)$_2$, —S(=O)R$^5$, —S(=O)$_2$R$^5$, or —NR$^5$C(=O)R$^5$; or two R$^6$ groups on the same nitrogen atom are taken together with the nitrogen atom to which they are attached to form substituted or unsubstituted C$_2$-C$_{10}$heterocycloalkyl;

R$^7$ is H, —OR$^5$, —N(R$^5$)$_2$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_8$cycloalkyl, substituted or unsubstituted C$_2$-C$_7$heterocycloalkyl, substituted or unsubstituted aryl, or substituted or unsubstituted heteroaryl;

each R$^8$ and R$^9$ is independently H, D, F, —CN, —OR$^5$, —SR$^5$, —N(R$^5$)$_2$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_1$-C$_6$alkylene-OR$^5$, substituted or unsubstituted C$_3$-C$_8$cycloalkyl, substituted or unsubstituted C$_2$-C$_7$heterocycloalkyl, substituted or unsubstituted aryl, or substituted or unsubstituted heteroaryl; or R$^8$ and R$^9$ taken together with the carbon atom to which they are attached to form substituted or unsubstituted C$_3$-C$_8$cycloalkyl or substituted or unsubstituted C$_2$-C$_7$heterocycloalkyl;

Z is CR$^6$;

W is substituted or unsubstituted C$_1$-C$_4$alkylene, substituted or unsubstituted C$_2$-C$_4$alkenylene, or substituted or unsubstituted C$_1$-C$_4$heteroalkylene;

R is selected from the group consisting of H, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_8$cycloalkyl, substituted or unsubstituted C$_2$-C$_7$heterocycloalkyl, substituted or unsubstituted aryl, and substituted or unsubstituted heteroaryl, wherein if alkyl is substituted then it is substituted with hydroxy, amino, substituted or unsubstituted mono-C$_1$-C$_6$alkylamino or substituted or unsubstituted di-C$_1$-C$_6$alkylamino;

R$^{11}$, R$^{12}$, R$^{13}$, R$^{14}$, R$^{15}$, R$^{16}$, R$^{17}$, and R$^{18}$ are each independently selected from the group consisting of H, F, OR$^5$, substituted or unsubstituted C$_1$-C$_6$alkyl, substituted or unsubstituted C$_1$-C$_6$fluoroalkyl, substituted or unsubstituted C$_1$-C$_6$heteroalkyl, wherein if alkyl is substituted then it is substituted with hydroxy, amino, methoxy, substituted or unsubstituted mono-C$_1$-C$_6$alkylamino or substituted or unsubstituted di-C$_1$-C$_6$alkylamino;

a and b are each independently selected from 0, 1, 2, or 3;

c and d are each independently selected from 1, 2, 3, or 4; and wherein the compound of Formula (I) is a single isomer substantially free of other isomers.

In another aspect, the splice modifying compounds described herein have the structure of Formula (II), or a pharmaceutically acceptable salt or solvate thereof:

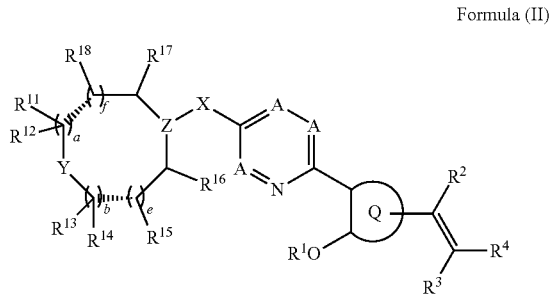

Formula (II)

wherein, each A is independently N or CR$^A$;

each R$^A$ is independently selected from H, D, halogen, —CN, —OH, —OR$^5$, =O, =N—OR$^5$, —SR$^5$, —S(=O)R$^5$, —S(=O)$_2$R$^5$, —S(=O)(=NR$^5$)R$^5$, —N(R$^5$)$_2$, —NR$^5$S(=O)(=NR$^5$)R$^6$, —NR$^5$S(=O)$_2$R$^6$, —S(=O)$_2$N(R$^5$)$_2$, —C(=O)R$^5$, —OC(=O)R$^5$, —C(=O)OR$^5$, —OC(=O)OR$^5$, —C(=O)N(R$^5$)$_2$, —OC(=O)N(R$^5$)$_2$, —NR$^5$C(=O)R$^5$, —P(=O)(R$^6$)$_2$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_8$cycloalkyl, substituted or unsubstituted C$_2$-C$_7$heterocycloalkyl, substituted or unsubstituted aryl, and substituted or unsubstituted monocyclic heteroaryl;

ring Q is substituted monocyclic aryl or substituted monocyclic heteroaryl;

X is absent, —O—, —NR$^7$—, —CR$^8$R$^9$—, —C(=O)—, —C(=C(R$^6$)$_2$)—, —CR$^6$=CR$^6$—, —S—, —S(=O)—, —S(=O)$_2$—, or —S(=O)(=NR$^5$)—;

each R$^1$ and R$^5$ is independently H, D, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_8$cycloalkyl, substituted or unsubstituted C$_2$-C$_7$heterocycloalkyl, substituted or unsubstituted aryl, or substituted or unsubstituted heteroaryl;

each R$^2$ and R$^3$ is independently H, D, halogen, substituted or unsubstituted C$_1$-C$_6$alkyl, substituted or unsubstituted C$_1$-C$_6$haloalkyl, substituted or unsubstituted aryl, substituted or unsubstituted monocyclic heteroaryl, —OR$^5$, —N(R$^5$)$_2$, —CH$_2$OR$^5$, —C(=O)R$^5$, —C(=O)OR$^5$, —C(=O)N(R$^5$)$_2$, —S(=O)R$^5$, —S(=O)$_2$R$^5$, or —NR$^5$C(=O)R$^5$;

R$^4$ is —C(=O)R$^5$, —C(=O)OR$^5$, —C(=O)N(R$^6$)$_2$, —C=(O)N(OR$^5$)(R$^5$), —P(=O)(R$^6$)$_2$, —P(=O)(R$^6$)N(R$^6$)$_2$, —S(=O)R$^6$, —S(=O)$_2$R$^6$, —S(=O)(=NR$^5$)R$^5$, —N(R$^6$)C(=O)R$^6$, N(R$^6$)S(=O)R$^6$, N(R$^6$)S(=O)$_2$R$^6$, —C(=O)N(R$^6$)S(=O)$_2$R$^6$, —N(R$^6$)C(=O)N(R$^6$)$_2$, substituted or unsubstituted cycloalkyl, substituted or unsubstituted heterocycloalkyl, substituted or unsubstituted aryl, or substituted or unsubstituted heteroaryl;

each $R^6$ is independently H, D, substituted or unsubstituted $C_1$-$C_6$alkyl, substituted or unsubstituted $C_1$-$C_6$haloalkyl, substituted or unsubstituted aryl, substituted or unsubstituted monocyclic heteroaryl, —$OR^5$, —$N(R^5)_2$, —$CH_2OR^5$, —$C(=O)R^5$, —$C(=O)OR^5$, —$C(=O)N(R^5)_2$, —$S(=O)R^5$, —$S(=O)_2R^5$, or —$NR^5C(=O)R^5$; or two $R^6$ groups on the same nitrogen atom are taken together with the nitrogen atom to which they are attached to form substituted or unsubstituted $C_2$-$C_{10}$heterocycloalkyl;

$R^7$ is H, —$OR^5$, —$N(R^5)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl;

each $R^8$ and $R^9$ is independently H, D, F, —CN, —$OR^5$, —$SR^5$, —$N(R^5)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_1$-$C_6$alkylene-$OR^5$, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl; or $R^8$ and $R^9$ taken together with the carbon atom to which they are attached to form substituted or unsubstituted $C_3$-$C_8$cycloalkyl or substituted or unsubstituted $C_2$-$C_7$heterocycloalkyl;

Y is NR or $CR^5R^6$;

Z is N or $CR^6$;

R is selected from the group consisting of H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, and substituted or unsubstituted heteroaryl, wherein if alkyl is substituted then it is substituted with hydroxy, amino, substituted or unsubstituted mono-$C_1$-$C_6$alkylamino or substituted or unsubstituted di-$C_1$-$C_6$alkylamino;

$R^{11}$, $R^{12}$, $R^{13}$, $R^{14}$, $R^{15}$, $R^{16}$, $R^{17}$, and $R^{18}$ are each independently selected from the group consisting of H, F, $OR^5$, substituted or unsubstituted $C_1$-$C_6$alkyl, substituted or unsubstituted $C_1$-$C_6$fluoroalkyl, substituted or unsubstituted $C_1$-$C_6$heteroalkyl, wherein if alkyl is substituted then it is substituted with hydroxy, amino, methoxy, substituted or unsubstituted mono-$C_1$-$C_6$alkylamino or substituted or unsubstituted di-$C_1$-$C_6$alkylamino; or $R^{11}$ and $R^{13}$ are taken together to form substituted or unsubstituted $C_1$-$C_3$alkylene group or substituted or unsubstituted $C_1$-$C_3$heteroalkylene group; or $R^{11}$ and $R^{15}$ are taken together to form substituted or unsubstituted $C_1$-$C_3$alkylene group; or $R^{15}$ and $R^{18}$ are taken together to form a bond or substituted or unsubstituted $C_1$-$C_3$alkylene group; or $R^{16}$ and $R^{17}$ are taken together to form substituted or unsubstituted $C_1$-$C_3$alkylene group;

$R^{13}$ and $R^{14}$ are taken together with the carbon atom to which they are attached to form a spirocyclic $C_3$-$C_8$cycloalkyl; or when Z is $CR^6$, then $R^{17}$ and $R^{16}$ are taken together to form a bond or substituted or unsubstituted $C_1$-$C_3$alkylene group; or when X is —$NR^7$— and Z is $CR^6$, then $R^7$ and $R^6$ are taken together with the intervening atoms to which they are attached to form a 4, 5, or 6-membered ring; or when X is —$NR^7$—, then $R^7$ and $R^{16}$ are taken together with the intervening atoms to which they are attached to form a 4, 5, or 6-membered ring;

when X is —$CR^8R^9$— and Z is $CR^6$, then $R^6$ and $R^8$ are taken together to form a bond;

a and b are each independently selected from 0, 1, 2, or 3; and e and f are each independently selected from 0, 1, or 2.

In one aspect, described herein is a compound of Formula (III), or a pharmaceutically acceptable salt or solvate thereof:

Formula (III)

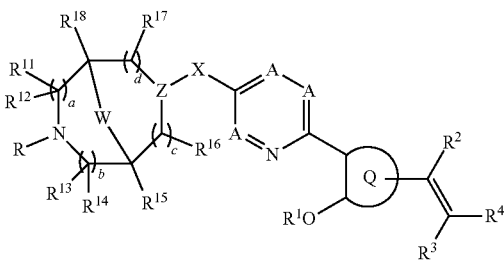

wherein, each A is independently N or $CR^4$;

each $R^4$ is independently selected from hydrogen, deuterium, halogen, —CN, —OH, —$OR^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, and substituted or unsubstituted $C_2$-$C_7$heterocycloalkyl;

ring Q is substituted monocyclic aryl or substituted monocyclic heteroaryl;

X is —O—, —S—, or —$NR^7$—;

each $R^1$ and $R^5$ is independently hydrogen, deuterium, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, or substituted or unsubstituted $C_2$-$C_7$heterocycloalkyl;

each $R^2$ and $R^3$ is independently hydrogen, deuterium, substituted or unsubstituted $C_1$-$C_4$alkyl, substituted or unsubstituted $C_1$-$C_6$haloalkyl, or substituted or unsubstituted $C_3$-$C_8$cycloalkyl;

$R^4$ is —$C(=O)R^5$, —$C(=O)OR^5$, —$C(=O)N(R^6)_2$, —$S(=O)R^6$, or —$S(=O)_2R^6$;

each $R^6$ is independently hydrogen, deuterium, substituted or unsubstituted $C_1$-$C_6$alkyl, substituted or unsubstituted $C_1$-$C_6$haloalkyl, substituted or unsubstituted aryl, substituted or unsubstituted monocyclic heteroaryl, —$OR^5$, —$N(R^5)_2$, or —$CH_2OR^5$; or two $R^6$ groups on the same nitrogen atom are taken together with the nitrogen atom to which they are attached to form substituted or unsubstituted $C_2$-$C_8$heterocycloalkyl;

R⁷ is hydrogen, —OR⁵, —N(R⁵)₂, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl;

Z is $CR^8$;

$R^8$ is hydrogen, deuterium, substituted or unsubstituted $C_1$-$C_6$alkyl, substituted or unsubstituted $C_1$-$C_6$haloalkyl, or substituted or unsubstituted $C_1$-$C_6$heteroalkyl;

W is substituted or unsubstituted $C_1$-$C_4$alkylene, substituted or unsubstituted $C_2$-$C_4$alkenylene, substituted or unsubstituted $C_1$-$C_4$heteroalkylene, or substituted or unsubstituted $C_3$-$C_6$cycloalkylene;

R is selected from the group consisting of hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, and substituted or unsubstituted heteroaryl;

$R^{11}$, $R^{12}$, $R^{13}$, $R^{14}$, $R^{15}$, $R^{16}$, $R^{17}$, and $R^{18}$ are each independently selected from the group consisting of hydrogen, F, —OR⁵, substituted or unsubstituted $C_1$-$C_6$alkyl, substituted or unsubstituted $C_1$-$C_6$fluoroalkyl, and substituted or unsubstituted $C_1$-$C_6$heteroalkyl;

a and b are each independently 0 or 1; and c and d are each independently 0 or 1.

Any combination of the groups described above or below for the various variables is contemplated herein. Throughout the specification, groups and substituents thereof are chosen by one skilled in the field to provide stable moieties and compounds.

In one aspect, described herein is a pharmaceutical composition comprising a splice modifying compound described herein or a pharmaceutically acceptable salt or solvate thereof, and at least one pharmaceutically acceptable excipient.

In some embodiments, the splice modifying compound described herein or a pharmaceutically acceptable salt or solvate thereof, is formulated for administration to a mammal by intravenous administration, subcutaneous administration, oral administration, inhalation, nasal administration, dermal administration, or ophthalmic administration. In some embodiments, the compound described herein or a pharmaceutically acceptable salt or solvate thereof, is in the form of a tablet, a pill, a capsule, a liquid, a suspension, a gel, a dispersion, a solution, an emulsion, an ointment, or a lotion.

In one aspect, described herein is a method of treating cancer mediated by forkhead box protein M1 (FOXM1) activity in a mammal comprising administering a forkhead box protein M1 (FOXM1) gene splice modifying compound as described herein, or a pharmaceutically acceptable salt or solvate thereof, to the mammal.

In another aspect, described herein is the use of a FOXM1 gene splice modifying compound as described herein, or a pharmaceutically acceptable salt or solvate thereof, in the manufacture of a medicament for the treatment or prevention of cancer that is mediated by FOXM1 activity.

In another aspect, described herein is a method of increasing expression of FOXM1 protein by cells having a mutation that causes exon skipping of pre-mRNA that encodes FOXM1 protein, the pre-mRNA comprising the mutation that causes exon skipping, the method comprising contacting the cells with a splice modifying compound described herein, or a pharmaceutically acceptable salt thereof, that binds to the pre-mRNA encoding FOXM1 protein, whereby an exon is not spliced from the pre-mRNA encoding FOXM1 protein, thereby increasing the level of mRNA encoding FOXM1 protein, and increasing the expression of FOXM1 protein in the cells.

In another aspect, described herein is a method of preventing exon skipping by cells having a mutation that causes exon skipping of pre-mRNA that encodes FOXM1 protein, the method comprising contacting the cells with a splice modifying compound described herein, or a pharmaceutically acceptable salt thereof, that binds to a pre-mRNA encoding FOXM1 protein, whereby the exon is not spliced from the pre-mRNA encoding FOXM1 protein, thereby increasing the expression of functional FOXM1 protein in the cells.

In another aspect, described herein is a method of treating a subject having a condition caused by a deficient amount or activity of FOXM1 protein comprising administering to the subject a splice modifying compound described herein, or a pharmaceutically acceptable salt thereof.

In some aspects, provided herein is a method for the treatment, prevention and/or delay of progression of cancer comprising administering an effective amount of the compound described above or a pharmaceutically acceptable salt or solvate thereof, to a subject. In some aspects, provided herein is a method of modulating splicing comprising contacting the compound described above to a pre-mRNA.

In some embodiments, the pre-mRNA is a FOXM1 pre-mRNA. In some embodiments, the compound binds to the FOXM1 pre-mRNA and modulates splicing of the FOXM1 pre-mRNA in a cell of a subject. In some embodiments, modulating comprises promoting exon skipping of the FOXM1 pre-mRNA. In some embodiments, modulating alters the ratio of a first splice variant of the FOXM1 pre-mRNA to a second splice variant of the FOXM1 pre-mRNA. In some embodiments, the first splice variant is a FOXM1 mRNA encoding a full length FOXM1 protein and wherein the second splice variant is a FOXM1 mRNA encoding a truncated FOXM1 protein. In some embodiments, modulating increases the ratio of the FOXM1 mRNA encoding the FOXM1 protein to the FOXM1 mRNA encoding the full length FOXM1 protein. In some embodiments, modulating decreases the ratio of the FOXM1 mRNA encoding the full length FOXM1 protein to the FOXM1 mRNA encoding the truncated FOXM1 protein. In some embodiments, the ratio of the FOXM1 mRNA encoding the truncated FOXM1 protein to the FOXM1 mRNA encoding the full length FOXM1 protein is altered in at least 20%, at least 50%, at least 75%, or at least 90% of the cells. In some embodiments, the compound modulates affinity between the FOXM1 pre-mRNA and a splicing complex component.

In some embodiments, the splicing complex component comprises a snRNA. In some embodiments, the snRNA comprises U1 snRNA, U2 snRNA, U4 snRNA, U5 snRNA, U6 snRNA, U11 snRNA, U12 snRNA, U4atac snRNA, U5 snRNA, U6 atac snRNA, or any combination thereof. In some embodiments, the snRNA comprises U1 snRNA. In some embodiments, the splicing complex component comprises 9G8, A1 hnRNP, A2 hnRNP, ASD-1, ASD-2b, ASF, B1 hnRNP, C1 hnRNP, C2 hnRNP, CBP20, CBP80, CELF, F hnRNP, FBP11, Fox-1, Fox-2, G hnRNP, H hnRNP, hnRNP 1, hnRNP 3, hnRNP C, hnRNP G, hnRNP K, hnRNP M, hnRNP U, Hu, HUR, I hnRNP, K hnRNP, KH-type splicing regulatory protein (KSRP), L hnRNP, M hnRNP, mBBP, muscle-blind like (MBNL), NF45, NFAR, Nova-1, Nova-2, nPTB, P54/SFRS11, polypyrimidine tract binding protein (PTB), PRP19 complex proteins, R hnRNP, RNPC1, SAM68, SC35, SF, SF1/BBP, SF2, SF3A, SF3B, SFRS10, Sm proteins, SR proteins, SRm300, SRp20, SRp30c, SRP35C, SRP36, SRP38, SRp40, SRp55, SRp75, SRSF, STAR, GSG, SUP-12, TASR-1, TASR-2, TIA, TIAR, TRA2, TRA2a/b, U hnRNP, U1 snRNP, U11 snRNP, U12 snRNP, U1-C, U2 snRNP, U2AF1-RS2, U2AF35, U2AF65, U4 snRNP, U5 snRNP, U6 snRNP, Urp, YB1, or any combination thereof.

In some embodiments, the compound binds to a splicing complex. In some embodiments, the compound modulates binding affinity of the splicing complex to the FOXM1 pre-mRNA. In some embodiments, the compound modulates binding affinity of the splicing complex to the FOXM1 pre-mRNA at the splice site sequence. In some embodiments, the compound modulates binding affinity of the splicing complex to the FOXM1 pre-mRNA upstream of the splice site sequence or downstream of the splice site sequence. In some embodiments, the compound interacts with an unpaired bulged nucleobase of an RNA duplex, and wherein the RNA duplex comprises the splice site sequence. In some embodiments, the splice site sequence comprises at least one bulged nucleotide or a mutant nucleotide at the −3, −2, −1, +1, +2, +3, +4, +5 or +6 position of the splice site sequence.

In some embodiments, the compound modulates the resonance time of the splicing complex with the FOXM1 pre-mRNA. In some embodiments, the compound modulates the resonance time of the splicing complex with the FOXM1 pre-mRNA at the splice site sequence. In some embodiments, the compound modulates the resonance time of the splicing complex with the FOXM1 pre-mRNA upstream of the splice site sequence or downstream of the splice site sequence. In some embodiments, the compound modulates steric hindrance between the splicing complex and the FOXM1 pre-mRNA. In some embodiments, the compound modulates steric hindrance between the splicing complex and the FOXM1 pre-mRNA at the splice site sequence. In some embodiments, the compound modulates steric hindrance between the splicing complex and the FOXM1 pre-mRNA upstream of the splice site sequence or downstream of the splice site sequence. In some embodiments, the splice site sequence is a 5' splice site sequence, a 3' splice site sequence, a branch point splice site sequence, an exonic splicing enhancer (ESE) sequence, an exonic splicing silencer (ESS) sequence, an intronic splicing enhancer (ISE) sequence, an intronic splicing silencer (ISS) sequence, a polypyrimidine tract sequence, a cryptic splice site sequence, or any combination thereof.

DETAILED DESCRIPTION

Figure 1:
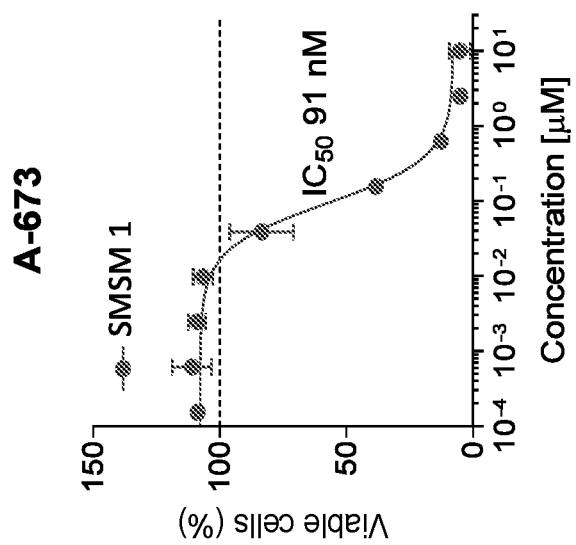
FIG. 1 depicts a graph of viable A-673 cells when incubated with the indicated concentrations of SMSM-1.

FOXM1 is a transcription factor of the Forkhead family. It is also known in the literature as Trident (in mouse), HFH-11 (in human), WIN or INS-1 (in rat), MPP-2 (partial human cDNA) or FKHL-16. The Forkhead family comprises a large number of transcription factors defined by a conserved DNA binding domain called Forkhead or winged-helix domain. The FOXM1 gene was cloned by screening cDNA libraries with degenerate primers for homologues with a conserved Forkhead DNA-binding domain (W. Korver, J. Roose, H. Clevers, Nucleic Acids Res. 25 (1997) 1715-1719). The FOXM1 gene was revealed to encode a Forkhead transcription factor family member that exhibits 45% identity in the DNA-binding domain with five of its closest related Forkhead members, namely FoxA3 (HNF-3γ, FoxC1 (fkh-1), FoxF2 (FREAC-2), FoxK1 (ILF) and FoxN2 (HTLF). The FOXM1 C-terminal region was found to have homology (76% identity) with a human partial cDNA encoding an open reading-frame of 221 amino acids, termed MPP-2. MPP-2 stands for MPM-2-reactive phosphoprotein-2 and was identified after screening a lymphoblast-derived cDNA library with the MPM-2 monoclonal antibody, which binds specifically to epitopes on mitotic proteins that are phosphorylated in a phosphoserine-proline dependent manner. FOXM1 binds DNA in vitro through the consensus site TAAACA. This motif shares the core sequence recognized by other members of the forkhead family. In particular, repeats of these motifs, in alternating orientation, were often characterized within the selected binding sequences for FOXM1.

The human FOXM1 gene is a 10-exon structure spanning approximately 25 kb on the 12p13-3 chromosomal band (telomeric position) (W. Korver, J. Roose, H. Clevers, Nucleic Acids Res. 25 (1997) 1715-1719). Two exons, named exons Va and VIIa, also referred to as exon A1 (or rat exon 6) and A2 respectively, are alternatively spliced (H. Ye, T. F. Kelly, U. Samadani, L. Lim, S. Rubio, D. G. Overdier, K. A. Roebuck, R. H. Costa, Mol. Cell Biol. 17 (1997) 1626-1641). Exon Va encodes a 15 amino-acid insertion within the C-terminal part of the DNA binding-domain, and is not seen in any of the other Forkhead transcription factor family members. Exon VIIa represents a 38 amino-acid insertion within the C-terminus of the protein. Differential splicing of exons Va and VIIa in human FOXM1, gives rise to three classes of transcripts, class A containing both alternative exons, class B containing none of the alternative exons, and class C in which exon Va only is retained (H. Ye, T. F. Kelly, U. Samadani, L. Lim, S. Rubio, D. G. Overdier, K. A. Roebuck, R. H. Costa, Mol. Cell Biol. 17 (1997) 1626-1641). Both FOXM1B and FOXM1C are transcriptionally active, whereas FOXM1A is transcriptionally inactive, due to the insertion of exon VIIa in the C-terminal transactivation domain. This disruption of the transactivation domain in FOXM1A not only leads to transcriptional inactivation, it might also cause this variant to act as a dominant-negative variant as it has retained normal DNA binding activity in the absence of a functional transactivation domain (H. Ye, T. F. Kelly, U. Samadani, L. Lim, S. Rubio, D. G. Overdier, K. A. Roebuck, R. H. Costa, Mol. Cell Biol. 17 (1997) 1626-1641).

FOXM1 is overexpressed in a broad range of tumor types, including those of neural, gastrointestinal, and reproductive origin (see Bektas et al., supra; Nakamura et al., 2004, Oncogene 23: 2385-400; Pilarsky et al., 2004, Neoplasia. Q: 744-50; Liu et al., 2006, Cancer Res 66: 3593-602). This expression pattern of FOXM1 is attributed to the ability of FOXM1 to transactivate genes required for cell cycle progression (Wang et al., 2002, Proc Nat. Acad Sci US A 99: 16881-6). Increased nuclear staining of FOXM1B found in human basal cell carcinomas suggests that FOXM1 is required for cellular proliferation in human cancers (Teh et al., 2002, Cancer Res. 62: 4773-80). The detailed role of FOXM1 in establishing or facilitating tumor progression and disease management has not been fully elucidated, however.

The problem to be solved by the present disclosure is to provide new compounds suitable for modifying splicing of the FOXM1 gene for use in the treatment of cancer.

Compounds

Described herein are compounds modifying splicing of the FOXM1 gene for use in the treatment, prevention and/or delay of progression of cancer, wherein the compounds induce a transcriptionally inactive FOXM1 variant. In some embodiments, the transcriptionally inactive FOXM1 variant is FOXM1 A. In some embodiments, the compounds modifying splicing are referred herein to as small molecule splicing modulators (SMSMs).

In one aspect, described herein is a compound of Formula (I), or a pharmaceutically acceptable salt or solvate thereof:

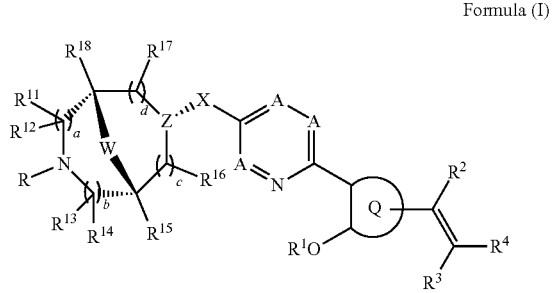

Formula (I)

wherein,
each A is independently N or $CR^4$;
each $R^A$ is independently selected from H, D, halogen, —CN, —OH, —$OR^5$, =O, =N—$OR^5$, —$SR^5$, —S(=O)$R^5$, —S(=O)$_2R^5$, —S(=O)(=$NR^5$)$R^5$, —N($R^5$)$_2$, —$NR^5$S(=O)(=$NR^5$)$R^6$, —$NR^5$S(=O)$_2$$R^6$, —S(=O)$_2$N($R^5$)$_2$, —C(=O)$R^5$, —OC(=O)$R^5$, —C(=O)$OR^5$, —OC(=O)$OR^5$, —C(=O)N($R^5$)$_2$, —OC(=O)N($R^5$)$_2$, —$NR^5$C(=O)$R^5$, —P(=O)($R^6$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, and substituted or unsubstituted monocyclic heteroaryl;
ring Q is substituted monocyclic aryl or substituted monocyclic heteroaryl;
X is absent, —O—, —$NR^7$—, —$CR^8R^9$—, —C(=O)—, —C(=C($R^6$)$_2$)—, —$CR^6$=$CR^6$—, —S—, —S(=O)—, —S(=O)$_2$—, or —S(=O)(=$NR^5$)—;
each $R^1$ and $R^5$ is independently H, D, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl;
each $R^2$ and $R^3$ is independently H, D, halogen, substituted or unsubstituted $C_1$-$C_6$alkyl, substituted or unsubstituted $C_1$-$C_6$haloalkyl, substituted or unsubstituted aryl, substituted or unsubstituted monocyclic heteroaryl, —$OR^5$, —N($R^5$)$_2$, —$CH_2OR^5$, —C(=O)$R^5$, —C(=O)$OR^5$, —C(=O)N($R^5$)$_2$, —S(=O)$R^5$, —S(=O)$_2R^5$, or —$NR^5$C(=O)$R^5$;
$R^4$ is —C(=O)$R^5$, —C(=O)$OR^5$, —C(=O)N($R^6$)$_2$, —C=(O)N($OR^5$)($R^5$), —P(=O)($R^6$)$_2$, —P(=O)($R^6$)N($R^6$)$_2$, —S(=O)$R^6$, —S(=O)$_2R^6$, —S(=O)(=$NR^5$)$R^5$, —N($R^6$)C(=O)$R^6$, N($R^6$)S(=O)$R^6$, N($R^6$)S(=O)$_2R^6$, —C(=O)N($R^6$)S(=O)$_2R^6$, —N($R^6$)C(=O)N($R^6$)$_2$, substituted or unsubstituted cycloalkyl, substituted or unsubstituted heterocycloalkyl, substituted or unsubstituted aryl, or substituted or unsubstituted heteroaryl;
each $R^6$ is independently H, D, substituted or unsubstituted $C_1$-$C_6$alkyl, substituted or unsubstituted $C_1$-$C_6$haloalkyl, substituted or unsubstituted aryl, substituted or unsubstituted monocyclic heteroaryl, —$OR^5$, —N($R^5$)$_2$, —$CH_2OR^5$, —C(=O)$R^5$, —C(=O)$OR^5$, —C(=O)N($R^5$)$_2$, —S(=O)$R^5$, —S(=O)$_2R^5$, or —$NR^5$C(=O)$R^5$; or two $R^6$ groups on the same nitrogen atom are taken together with the nitrogen atom to which they are attached to form substituted or unsubstituted $C_2$-$C_{10}$heterocycloalkyl;

$R^7$ is H, —$OR^5$, —$N(R^5)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl;

each $R^8$ and $R^9$ is independently H, D, F, —CN, —$OR^5$, —$SR^5$, —$N(R^5)_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_1$-$C_6$alkylene-$OR^5$, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl; or $R^8$ and $R^9$ taken together with the carbon atom to which they are attached to form substituted or unsubstituted $C_3$-$C_8$cycloalkyl or substituted or unsubstituted $C_2$-$C_7$heterocycloalkyl;

Z is $CR^6$;

W is substituted or unsubstituted $C_1$-$C_4$alkylene, substituted or unsubstituted $C_2$-$C_4$alkenylene, or substituted or unsubstituted $C_1$-$C_4$heteroalkylene;

R is selected from the group consisting of H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, and substituted or unsubstituted heteroaryl, wherein if alkyl is substituted then it is substituted with hydroxy, amino, substituted or unsubstituted mono-$C_1$-$C_6$alkylamino, or substituted or unsubstituted di-$C_1$-$C_6$alkylamino;

$R^{11}$, $R^{12}$, $R^{13}$, $R^{14}$, $R^{15}$, $R^{16}$, $R^{17}$, and $R^{18}$ are each independently selected from the group consisting of H, F, $OR^5$, substituted or unsubstituted $C_1$-$C_6$alkyl, substituted or unsubstituted $C_1$-$C_6$fluoroalkyl, substituted or unsubstituted $C_1$-$C_6$heteroalkyl, wherein if alkyl is substituted then it is substituted with hydroxy, amino, methoxy, substituted or unsubstituted mono-$C_1$-$C_6$alkylamino or substituted or unsubstituted di-$C_1$-$C_6$alkylamino;

a and b are each independently selected from 0, 1, 2, or 3; and c and d are each independently selected from 1, 2, 3, or 4.

In some embodiments, the compound of Formula (I) is a single isomer substantially free of other isomers.

In some embodiments, $R^{11}$ and $R^{13}$ are taken together to form substituted or unsubstituted $C_1$-$C_3$alkylene group or substituted or unsubstituted $C_1$-$C_3$heteroalkylene group; or $R^{11}$ and $R^{15}$ are taken together to form substituted or unsubstituted $C_1$-$C_3$alkylene group; or $R^{15}$ and $R^{18}$ are taken together to form a bond or substituted or unsubstituted $C_1$-$C_3$alkylene group;

$R^{16}$ and $R^{17}$ are taken together to form substituted or unsubstituted $C_1$-$C_3$alkylene group;

$R^{13}$ and $R^{14}$ are taken together to with the carbon atom to which they are attached, form a spirocyclic $C_3$-$C_8$cycloalkyl; or when Z is $CR^6$, then $R^{17}$ and $R^6$ are taken together to form a bond or substituted or unsubstituted $C_1$-$C_3$alkylene group; or when X is —$NR^7$— and Z is $CR^6$, then $R^7$ and $R^6$ are taken together with the intervening atoms to which they are attached to form a 4, 5, or 6-membered ring; or when X is —$NR^7$—, then $R^7$ and $R^{16}$ are taken together with the intervening atoms to which they are attached to form a 4, 5, or 6-membered ring; or when X is —$CR^8R^9$— and Z is $CR^6$, then $R^6$ and $R^8$ are taken together to form a bond.

In some embodiments,

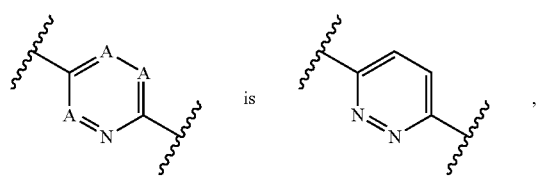 is 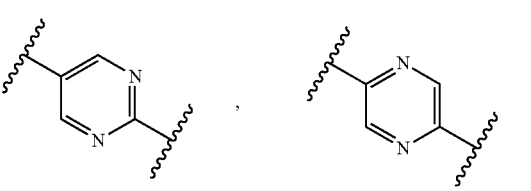,

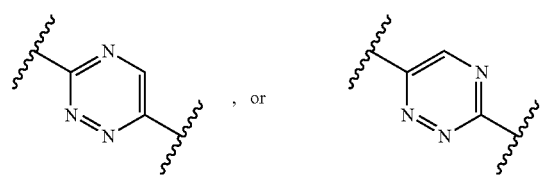, or 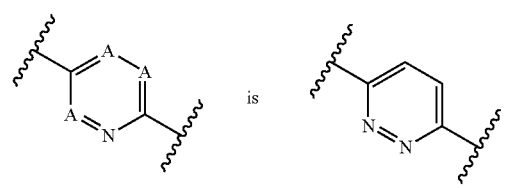.

In some embodiments,

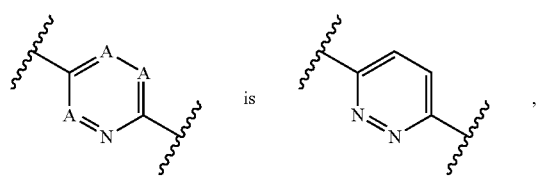 is 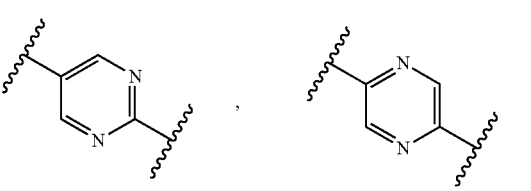.

In some embodiments,

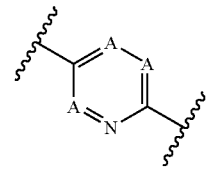

is

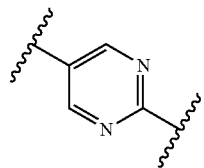

In some embodiments,

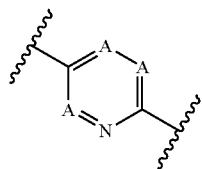

is

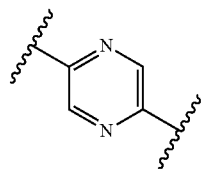

In some embodiments,

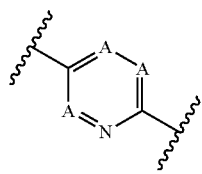

is

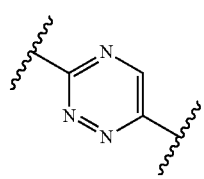

In some embodiments,

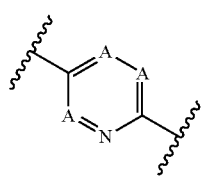

is

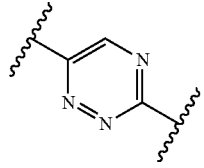

In some embodiments, X is —O—, —NR$^7$—, —S—, —CR$^8$R$^9$—, —C(=O)—, or —C(=C(R$^6$)$_2$)—. In some embodiments, X is —O—. In some embodiments, X is —NR$^7$—. In some embodiments, X is —S—. In some embodiments, X is —CR$^8$R$^9$—. In some embodiments, X is —C(=O)—. In some embodiments, X is —C(=C(R$^6$)$_2$)—.

In some embodiments, ring Q is substituted monocyclic aryl.

In some embodiments, ring Q is substituted phenyl.

In some embodiments, ring Q is

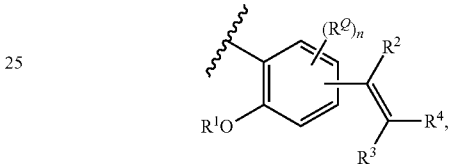

wherein each R$^Q$ is independently selected from cyano, halogen, hydroxy, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$alkoxy, substituted or unsubstituted C$_3$-C$_7$cycloalkyl, substituted or unsubstituted C$_2$-C$_8$heterocycloalkyl, heteroaryl, substituted or unsubstituted heterocycloalkyl-C$_1$-C$_6$alkyl, substituted or unsubstituted C$_1$-C$_6$alkyl-aryl, substituted or unsubstituted C$_1$-C$_6$alkyl-heterocycloalkyl, substituted or unsubstituted C$_1$-C$_6$alkyl-heteroaryl, substituted or unsubstituted C$_1$-C$_6$alkoxy-aryl, substituted or unsubstituted C$_1$-C$_6$ alkoxy-heterocycloalkyl, substituted or unsubstituted C$_1$-C$_6$ alkoxy-heteroaryl, and C$_1$-C$_6$alkoxy substituted with hydroxy, C$_1$-C$_6$alkoxy, amino, mono-C$_1$-C$_6$alkylamino and di-C$_1$-C$_6$alkylamino; and n is 0, 1, 2, or 3.

In some embodiments,

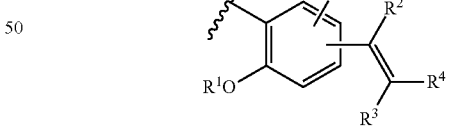

is

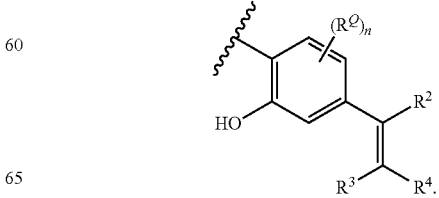

In some embodiments,

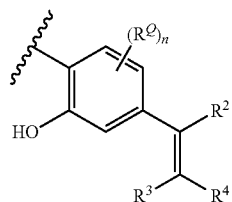

is

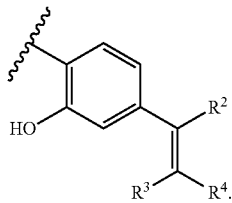

In some embodiments, ring Q is substituted monocyclic heteroaryl.

In some embodiments, ring Q is substituted 5 or 6 membered monocyclic heteroaryl.

In some embodiments, ring Q is substituted 6 membered monocyclic heteroaryl selected from the group consisting of:

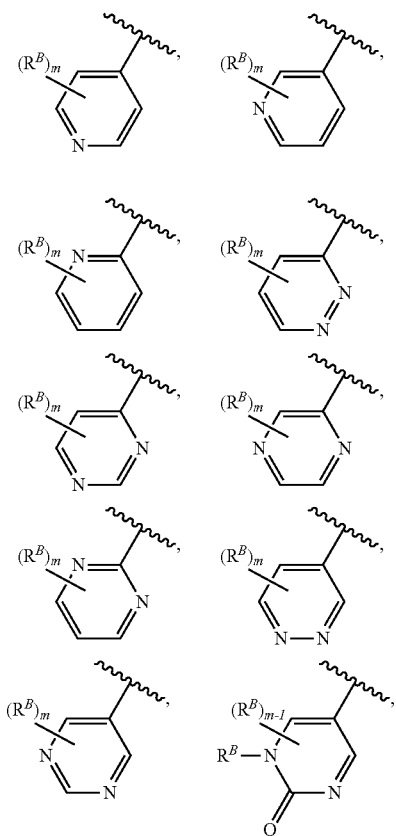

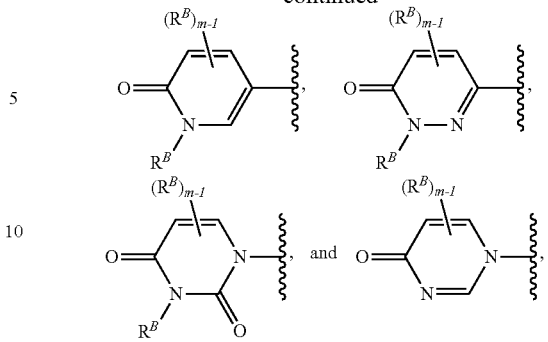

wherein each $R^B$ is independently selected from hydrogen, cyano, halogen, hydroxy, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_3$-$C_7$cycloalkyl, substituted or unsubstituted $C_2$-$C_8$heterocycloalkyl, heteroaryl, substituted or unsubstituted heterocycloalkyl-$C_1$-$C_6$alkyl, substituted or unsubstituted $C_1$-$C_6$alkyl-aryl, substituted or unsubstituted $C_1$-$C_6$alkyl-heterocycloalkyl, substituted or unsubstituted $C_1$-$C_6$alkyl-heteroaryl, substituted or unsubstituted $C_1$-$C_6$alkoxy-aryl, substituted or unsubstituted $C_1$-$C_6$alkoxy-heterocycloalkyl, substituted or unsubstituted $C_1$-$C_6$alkoxy-heteroaryl, and $C_1$-$C_6$alkoxy substituted with hydroxy, $C_1$-$C_6$alkoxy, amino, mono-$C_1$-$C_6$alkylamino and di-$C_1$-$C_6$alkylamino; and m is 1, 2, 3, or 4; provided that at least one $R^B$ is substituted or unsubstituted $C_2$-$C_6$alkenyl.

In some embodiments, X is —$NR^7$—.

In some embodiments, $R^7$ is —$OR^5$, substituted or unsubstituted $C_1$-$C_6$alkyl, substituted or unsubstituted $C_1$-$C_6$haloalkyl, substituted or unsubstituted $C_1$-$C_6$heteroalkyl, or substituted or unsubstituted $C_3$-$C_8$cycloalkyl. In some embodiments, $R^7$ is —$OR^5$. In some embodiments, $R^7$ is substituted or unsubstituted $C_1$-$C_6$alkyl. In some embodiments, $R^7$ is substituted or unsubstituted $C_1$-$C_6$haloalkyl. In some embodiments, $R^7$ is substituted or unsubstituted $C_1$-$C_6$heteroalkyl. In some embodiments, $R^7$ is substituted or unsubstituted $C_3$-$C_8$cycloalkyl.

In some embodiments, $R^7$ is $C_3$-$C_8$cycloalkyl that is selected from cyclopropyl, cyclobutyl, cyclopentyl, cyclohexyl, cycloheptyl, and cyclooctyl. In some embodiments, $R^7$ is cyclopropyl. In some embodiments, $R^7$ is cyclobutyl. In some embodiments, $R^7$ is cyclopentyl. In some embodiments, $R^7$ is cyclohexyl.

In some embodiments, $R^7$ is $C_3$-$C_8$cycloalkyl that is selected from cyclopentenyl, cyclohexenyl, cycloheptenyl, and cyclooctenyl. In some embodiments, $R^7$ is cyclopentenyl. In some embodiments, $R^7$ is cyclohexenyl.

In some embodiments, $R^7$ is —$CH_3$, —$CH_2CH_2F$, or —$CF_3$. In some embodiments, $R^7$ is —$CH_3$. In some embodiments, $R^7$ is —$CH_2CH_2F$. In some embodiments, $R^7$ is —$CF_3$.

In some embodiments, $R^7$ is —$OCH_3$, —$OCH_2CH_3$, —$OCH_2CH_2OH$, or —$OCH_2CH_2OCH_3$. In some embodiments, $R^7$ is —$OCH_3OCH_2CH_2OCH_3$. In some embodiments, $R^7$ is —$OCH_2CH_3OCH_2CH_2OCH_3$. In some embodiments, $R^7$ is —$OCH_2CH_2OH$. In some embodiments, $R^7$ is —$OCH_2CH_2OCH_3$.

In some embodiments, a is 0. In some embodiments, a is 1. In some embodiments, b is 0. In some embodiments, b is 1. In some embodiments, a is 0 and b is 0. In some embodiments, a is 0 and b is 1. In some embodiments, a is 1 and b is 0. In some embodiments, a is 1 and b is 1.

In some embodiments, c is 0. In some embodiments, c is 1. In some embodiments, d is 0. In some embodiments, d is 1. In some embodiments, c is 0 and d is 0. In some embodiments, c is 0 and d is 1. In some embodiments, c is 1 and d is 0. In some embodiments, c is 1 and d is 1.

In some embodiments,

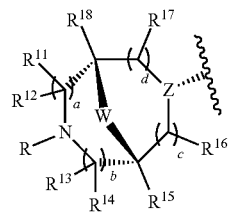

is

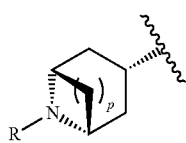 or 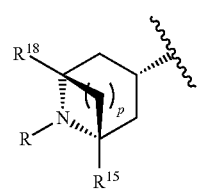

wherein p is 1, 2, or 3. In some embodiments, p is 2. In some embodiments, p is 3.

In some embodiments,

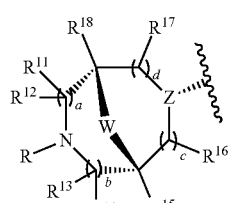

is

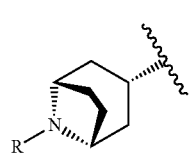 or 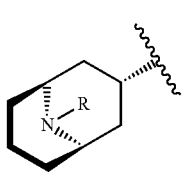

In some embodiments,

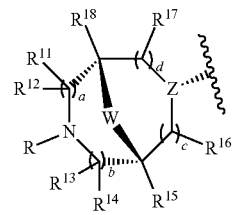

is

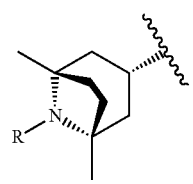

In some embodiments,

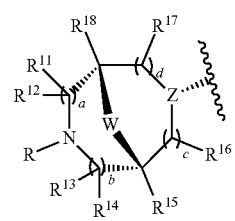

is

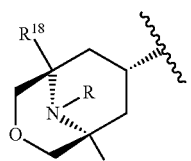 or 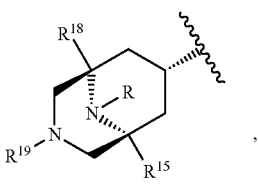, wherein
$R^{19}$ is H, D, —CN, —OH, —OR$^5$, —SR$^5$, —S(=O)R$^5$, —S(=O)$_2$R$^5$, —CH$_2$—N(R$^5$)$_2$, —S(=O)$_2$N(R$^5$)$_2$, —C(=O)R$^5$, —CO$_2$R$^5$, —C(=O)N(R$^5$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, or substituted or unsubstituted $C_2$-$C_8$heterocycloalkyl.

In some embodiments,

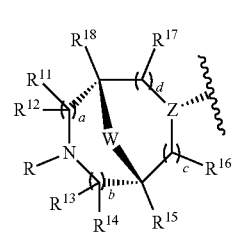

is

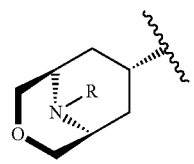

In some embodiments, the compound has the structure of Formula (Ia):

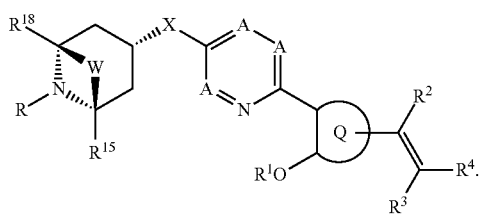

In some embodiments, each A is independently N or CH.

In some embodiments, ring Q is substituted monocyclic aryl.

In some embodiments, X is —O—, —NR$^7$—, —CR$^8$R$^9$—, —C(=O)—, or —S—.

In some embodiments, R is selected from the group consisting of H, substituted or unsubstituted C$_1$-C$_6$alkyl, substituted or unsubstituted C$_1$-C$_6$fluoroalkyl, and substituted or unsubstituted C$_1$-C$_6$heteroalkyl.

In some embodiments, each R$^{15}$ and R$^{18}$ are independently selected from the group consisting of H, F, OR$^9$, substituted or unsubstituted C$_1$-C$_6$alkyl, substituted or unsubstituted C$_1$-C$_6$fluoroalkyl.

In some embodiments, R$^1$ is H, D, substituted or unsubstituted C$_1$-C$_6$alkyl, substituted or unsubstituted C$_1$-C$_6$heteroalkyl, or substituted or unsubstituted C$_2$-C$_7$heterocycloalkyl.

In some embodiments, W is selected from the group consisting of —CH$_2$CH$_2$—, —CH$_2$CH$_2$CH$_2$—, and —CH$_2$OCH$_2$—.

In some embodiments, each R$^2$ and R$^3$ is independently H, D, halogen, or substituted or unsubstituted C$_1$-C$_6$alkyl. In some embodiments, each R$^2$ and R$^3$ is hydrogen. In some embodiments, R$^2$ is hydrogen and R$^3$ is CH$_3$. In some embodiments, R$^2$ is CH$_3$ and R$^3$ is hydrogen.

In some embodiments, R$^4$ is —C(=O)R$^5$, —C(=O)OR$^5$, —C(=O)N(R$^6$)$_2$, —C=(O)N(OR$^5$)(R$^5$), —P(=O)(R$^6$)$_2$, —P(=O)(R$^6$)N(R$^6$)$_2$, —S(=O)R$^6$, —S(=O)$_2$R$^6$, —S(=O)(=NR$^5$)R$^5$, —N(R$^6$)C(=O)R$^6$, N(R$^6$)S(=O)R$^6$, N(R$^6$)S(=O)$_2$R$^6$, —C(=O)N(R$^6$)S(=O)$_2$R$^6$, —N(R$^6$)C(=O)N(R$^6$)$_2$, substituted or unsubstituted cycloalkyl, substituted or unsubstituted heterocycloalkyl, substituted or unsubstituted aryl, or substituted or unsubstituted heteroaryl.

In some embodiments, two R$^6$ groups on the same nitrogen atom are taken together with the nitrogen atom to which they are attached to form substituted or unsubstituted C$_2$-C$_{10}$heterocycloalkyl.

In some embodiments, R$^4$ is —C(=O)OH, —C(=O)NH$_2$, —C(=O)NHCH$_3$, —C(=O)N(CH$_3$)$_2$, —C(=O)NH(OH), —C(=O)NH(OCH$_3$), —C(=O)N(CH$_3$)OH, C(=O)N(CH$_3$)OCH$_3$, —N(C(=O)CH$_3$)OH, —O—NH(C(=O)CH$_3$), —P(=O)(OH)$_2$, —PH(=O)(OH), —S(=O)$_2$OH, —S(=O)OH, —S(=O)$_2$CH$_3$, —S(=O)CH$_3$, —S(=O)$_2$NH$_2$, —S(=O)NH$_2$, —S(=O)$_2$NH(CH$_3$), —S(=O)NH(CH$_3$), —S(=O)$_2$N(CH$_3$)$_2$, —S(=O)N(CH$_3$)$_2$, —S(=O)(=NH)CH$_3$, —S(=O)(=NCH$_3$)CH$_3$, —NHS(=O)$_2$CH$_3$, —C(=O)NH(S(=O)$_2$CH$_3$), —C(=O)NH(S(=O)$_2$N(CH$_3$)$_2$), —NHC(=O)NH(S(=O)$_2$CH$_3$), or —NHC(=O)NH(C(=O)CH$_3$).

In some embodiments, R$^4$ is

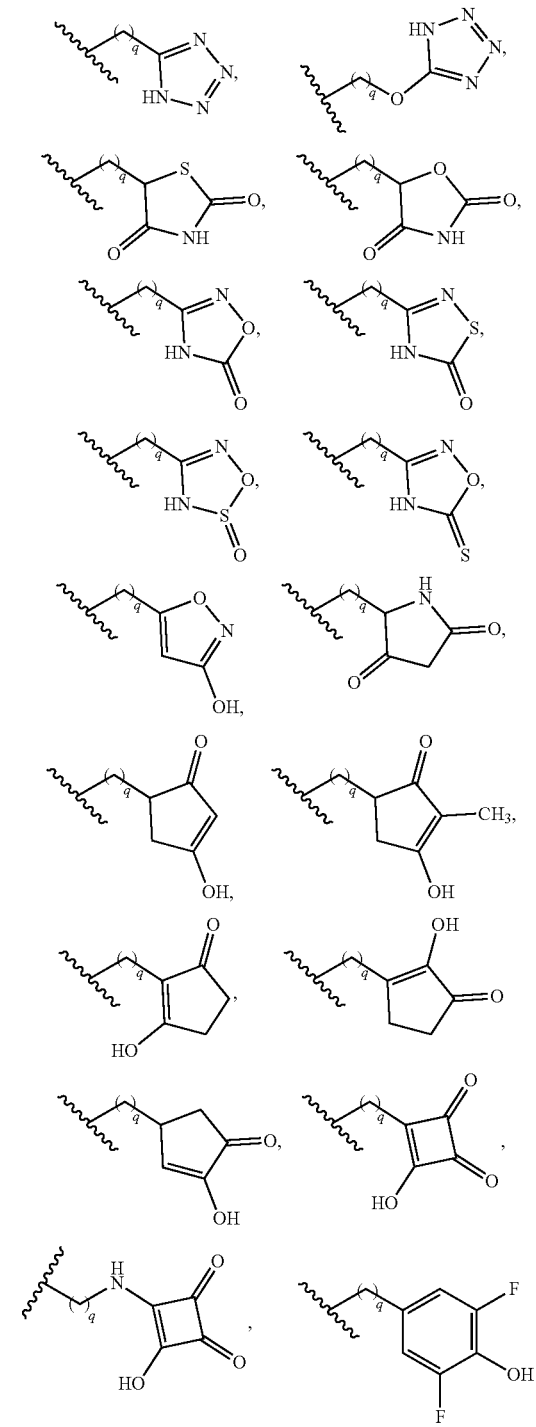

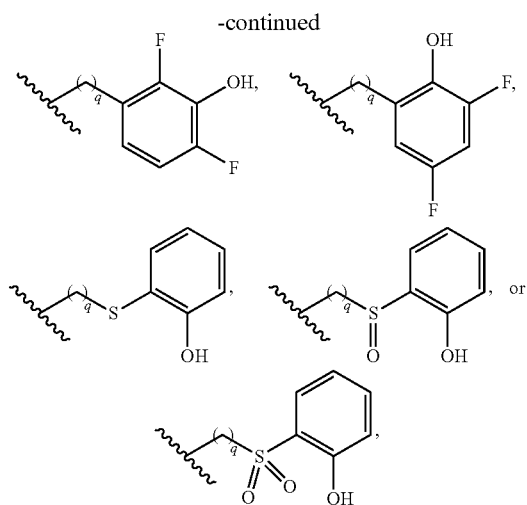

wherein q is 0, 1, or 2.

In some embodiments, the compound has the structure of Formula (Ib):

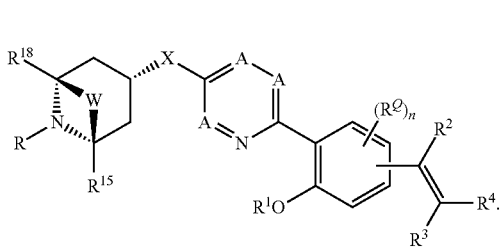

In some embodiments, the compound has the structure of Formula (Ic):

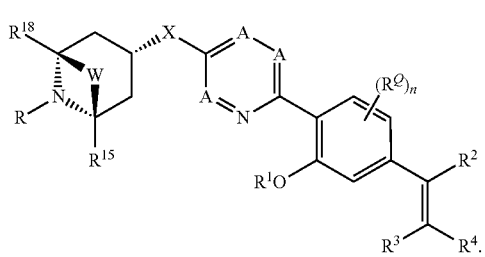

In some embodiments, the compound has the structure of Formula (Id):

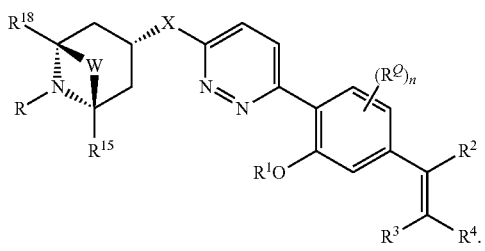

In some embodiments, the compound has the structure of Formula (Ie):

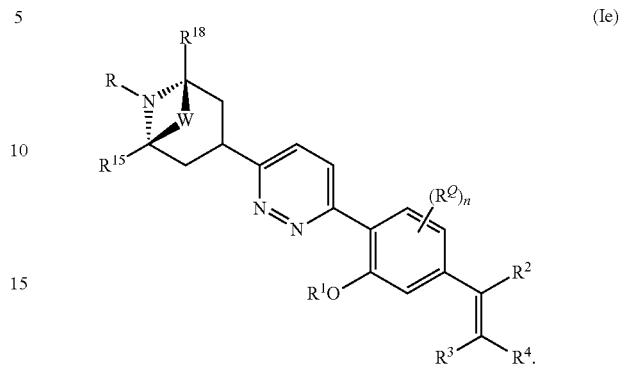

In some preferred embodiments, the compound of Formula (I) is not racemic. In some preferred embodiments, the compound of Formula (I) is substantially free of other isomers. In some preferred embodiments, the compound of Formula (I) comprises 25% or less of other isomers. In some preferred embodiments, the compound of Formula (I) comprises 20% or less of other isomers. In some preferred embodiments, the compound of Formula (I) comprises 15% or less of other isomers. In some preferred embodiments, the compound of Formula (I) comprises 10% or less of other isomers. In some preferred embodiments, the compound of Formula (I) comprises 5% or less of other isomers. In some preferred embodiments, the compound of Formula (I) comprises 1% or less of other isomers.

In some preferred embodiments, the asymmetric carbon atom (Z=CR$^6$) of the compound of Formula (I) is present in enantiomerically enriched form. In certain embodiments, the asymmetric carbon atom (Z=CR$^6$) of the compound of Formula (I) has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (S)- or (R)-configuration.

In another aspect, described herein is a compound of Formula (II), or a pharmaceutically acceptable salt or solvate thereof:

Formula (II)

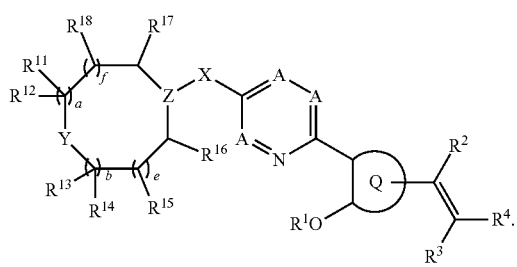

wherein,
each A is independently N or CR$^A$;
each R$^A$ is independently selected from H, D, halogen, —CN, —OH, —OR$^5$, =O, =N—OR$^5$, —SR$^5$, —S(=O)R$^5$, —S(=O)$_2$R$^5$, —S(=O)(=NR$^5$)R$^5$, —N(R$^5$)$_2$, —NR$^5$S(=O)(=NR$^5$)R$^6$, —NR$^5$S(=O)$_2$R$^6$, —S(=O)$_2$N(R$^5$)$_2$, —C(=O)R$^5$, —OC(=O)R$^5$, —C(=O)OR⁵, —OC(=O)OR⁵, —C(=O)N(R⁵)₂, —OC(=O)N(R⁵)₂, —NR⁵C(=O)R⁵, —P(=O)(R⁶)₂, substituted or unsubstituted C₁-C₆alkyl, substituted or unsubstituted C₁-C₆haloalkyl, substituted or unsubstituted C₁-C₆heteroalkyl, substituted or unsubstituted C₃-C₈cycloalkyl, substituted or unsubstituted C₂-C₇heterocycloalkyl, substituted or unsubstituted aryl, and substituted or unsubstituted monocyclic heteroaryl;

ring Q is substituted monocyclic aryl or substituted monocyclic heteroaryl;

X is absent, —O—, —NR⁷—, —CR⁸R⁹—, —C(=O)—, —C(=C(R⁶)₂)—, —CR⁶=CR⁶—, —S—, —S(=O)—, —S(=O)₂—, or —S(=O)(=NR⁵)—;

each R¹ and R⁵ is independently H, D, substituted or unsubstituted C₁-C₆alkyl, substituted or unsubstituted C₁-C₆haloalkyl, substituted or unsubstituted C₁-C₆heteroalkyl, substituted or unsubstituted C₃-C₈cycloalkyl, substituted or unsubstituted C₂-C₇heterocycloalkyl, substituted or unsubstituted aryl, or substituted or unsubstituted heteroaryl;

each R² and R³ is independently H, D, halogen, substituted or unsubstituted C₁-C₆alkyl, substituted or unsubstituted C₁-C₆haloalkyl, substituted or unsubstituted aryl, substituted or unsubstituted monocyclic heteroaryl, —OR⁵, —N(R⁵)₂, —CH₂OR⁵, —C(=O)R⁵, —C(=O)OR⁵, —C(=O)N(R⁵)₂, —S(=O)R⁵, —S(=O)₂R⁵, or —NR⁵C(=O)R⁵;

R⁴ is —C(=O)R⁵, —C(=O)OR⁵, —C(=O)ₙ(R⁶)₂, —C=(O)N(OR⁵)(R⁵), —P(=O)(R⁶)₂, —P(=O)(R⁶)N(R⁶)₂, —S(=O)R⁶, —S(=O)₂R⁶, —S(=O)(=NR⁵)R⁵, —N(R⁶)C(=O)R⁶, N(R⁶)S(=O)R⁶, N(R⁶)S(=O)₂R⁶, —C(=O)N(R⁶)S(=O)₂R⁶, —N(R⁶)C(=O)N(R⁶)₂, substituted or unsubstituted cycloalkyl, substituted or unsubstituted heterocycloalkyl, substituted or unsubstituted aryl, or substituted or unsubstituted heteroaryl;

each R⁶ is independently H, D, substituted or unsubstituted C₁-C₆alkyl, substituted or unsubstituted C₁-C₆haloalkyl, substituted or unsubstituted aryl, substituted or unsubstituted monocyclic heteroaryl, —OR⁵, —N(R⁵)₂, —CH₂OR⁵, —C(=O)R⁵, —C(=O)OR⁵, —C(=O)N(R⁵)₂, —S(=O)R⁵, —S(=O)₂R⁵, or —NR⁵C(=O)R⁵; or two R⁶ groups on the same nitrogen atom are taken together with the nitrogen atom to which they are attached to form substituted or unsubstituted C₂-C₁₀heterocycloalkyl;

R⁷ is H, —OR⁵, —N(R⁵)₂, substituted or unsubstituted C₁-C₆alkyl, substituted or unsubstituted C₁-C₆haloalkyl, substituted or unsubstituted C₁-C₆heteroalkyl, substituted or unsubstituted C₃-C₈cycloalkyl, substituted or unsubstituted C₂-C₇heterocycloalkyl, substituted or unsubstituted aryl, or substituted or unsubstituted heteroaryl;

each R⁸ and R⁹ is independently H, D, F, —CN, —OR⁵, —SR⁵, —N(R⁵)₂, substituted or unsubstituted C₁-C₆alkyl, substituted or unsubstituted C₁-C₆haloalkyl, substituted or unsubstituted C₁-C₆heteroalkyl, substituted or unsubstituted C₁-C₆alkylene-OR⁵, substituted or unsubstituted C₃-C₈cycloalkyl, substituted or unsubstituted C₂-C₇heterocycloalkyl, substituted or unsubstituted aryl, or substituted or unsubstituted heteroaryl; or R⁸ and R⁹ taken together with the carbon atom to which they are attached to form substituted or unsubstituted C₃-C₈cycloalkyl or substituted or unsubstituted C₂-C₇heterocycloalkyl;

Y is NR or CR⁵R⁶;

Z is N or CR⁶;

R is selected from the group consisting of H, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₈cycloalkyl, substituted or unsubstituted C₂-C₇heterocycloalkyl, substituted or unsubstituted aryl, and substituted or unsubstituted heteroaryl, wherein if alkyl is substituted then it is substituted with hydroxy, amino, substituted or unsubstituted mono-C₁-C₆alkylamino or substituted or unsubstituted di-C₁-C₆alkylamino;

R¹¹, R¹², R¹³, R¹⁴, R¹⁵, R¹⁶, R¹⁷, and R¹⁸ are each independently selected from the group consisting of H, F, OR⁵, substituted or unsubstituted C₁-C₆alkyl, substituted or unsubstituted C₁-C₆fluoroalkyl, substituted or unsubstituted C₁-C₆heteroalkyl, wherein if alkyl is substituted then it is substituted with hydroxy, amino, methoxy, substituted or unsubstituted mono-C₁-C₆alkylamino or substituted or unsubstituted di-C₁-C₆alkylamino;

R¹¹ and R¹³ are taken together to form substituted or unsubstituted C₁-C₃alkylene group or substituted or unsubstituted C₁-C₃heteroalkylene group; or R¹¹ and R¹⁵ are taken together to form substituted or unsubstituted C₁-C₃alkylene group; or R¹⁵ and R¹⁸ are taken together to form a bond or substituted or unsubstituted C₁-C₃alkylene group;

R¹⁶ and R¹⁷ are taken together to form substituted or unsubstituted C₁-C₃alkylene group;

R¹³ and R¹⁴ are taken together with the carbon atom to which they are attached to form a spirocyclic C₃-C₈cycloalkyl; or when Z is CR⁶, then R¹⁷ and R⁶ are taken together to form a bond or substituted or unsubstituted C₁-C₃alkylene group; or when X is —NR⁷— and Z is CR⁶, then R⁷ and R⁶ are taken together with the intervening atoms to which they are attached to form a 4, 5, or 6-membered ring; or when X is —NR⁷—, then R⁷ and R¹⁶ are taken together with the intervening atoms to which they are attached to form a 4, 5, or 6-membered ring;

when X is —CR⁸R⁹— and Z is CR⁶, then R⁶ and R⁸ are taken together to form a bond;

a and b are each independently selected from 0, 1, 2, or 3; and e and f are each independently selected from 0, 1, or 2.

In some embodiments,

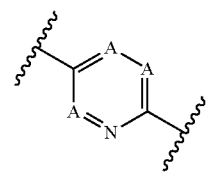

is
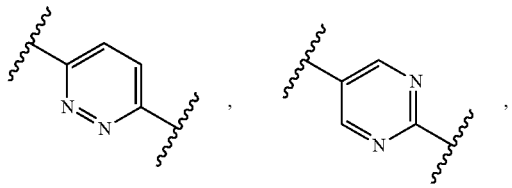
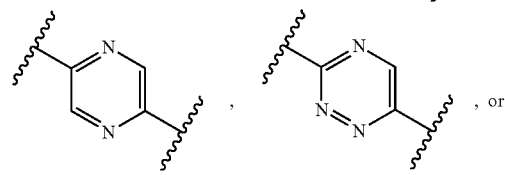
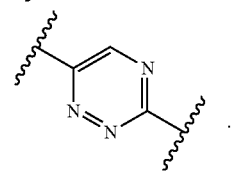
In some embodiments,
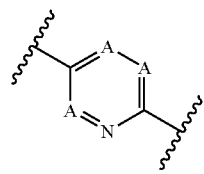
is
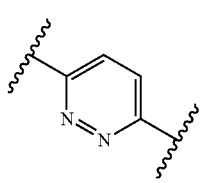
In some embodiments,
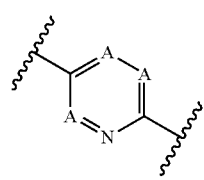
is
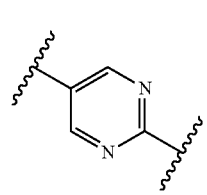
In some embodiments,
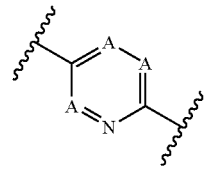
is
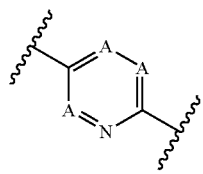
In some embodiments,
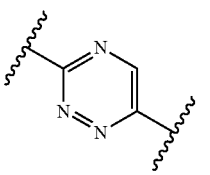
is
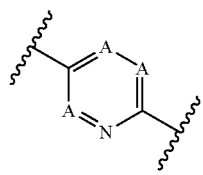
In some embodiments,
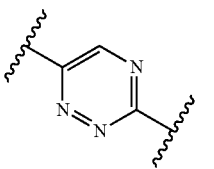
is
In some embodiments, X is —O—, —NR⁷—, —S—, —CR⁸R⁹—, —C(=O)—, or —C(=C(R⁶)₂)—. In some embodiments, X is —O—. In some embodiments, X is —NR⁷—. In some embodiments, X is —S—. In some embodiments, X is —CR⁸R⁹—. In some embodiments, X is —C(=O)—. In some embodiments, X is —C(=C(R⁶)₂)—.

In some embodiments, ring Q is substituted monocyclic aryl.

In some embodiments, ring Q is substituted phenyl.

In some embodiments, ring Q is

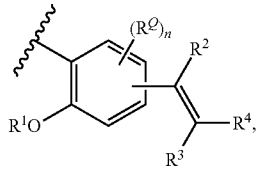

wherein each $R^Q$ is independently selected from cyano, halogen, hydroxy, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_3$-$C_7$cycloalkyl, substituted or unsubstituted $C_2$-$C_8$heterocycloalkyl, heteroaryl, substituted or unsubstituted heterocycloalkyl-$C_1$-$C_6$alkyl, substituted or unsubstituted $C_1$-$C_6$alkyl-aryl, substituted or unsubstituted $C_1$-$C_6$alkyl-heterocycloalkyl, substituted or unsubstituted $C_1$-$C_6$alkyl-heteroaryl, substituted or unsubstituted $C_1$-$C_6$alkoxy-aryl, substituted or unsubstituted $C_1$-$C_6$alkoxy-heterocycloalkyl, substituted or unsubstituted $C_1$-$C_6$alkoxy-heteroaryl, and $C_1$-$C_6$alkoxy substituted with hydroxy, $C_1$-$C_6$alkoxy, amino, mono-$C_1$-$C_6$alkylamino and di-$C_1$-$C_6$alkylamino; and n is 0, 1, 2, or 3.

In some embodiments,

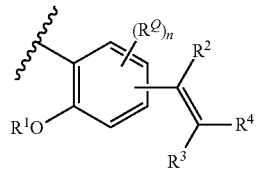

is

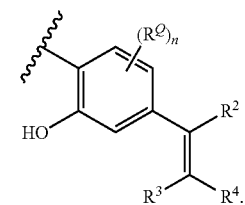

In some embodiments,

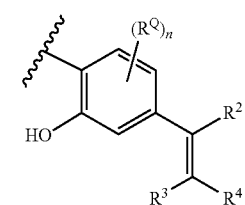

is

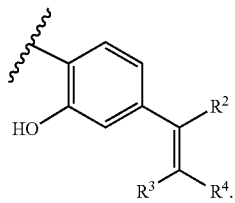

In some embodiments, ring Q is substituted monocyclic heteroaryl.

In some embodiments, ring Q is substituted 5 or 6 membered monocyclic heteroaryl.

In some embodiments, ring Q is substituted 6 membered monocyclic heteroaryl selected from the group consisting of:

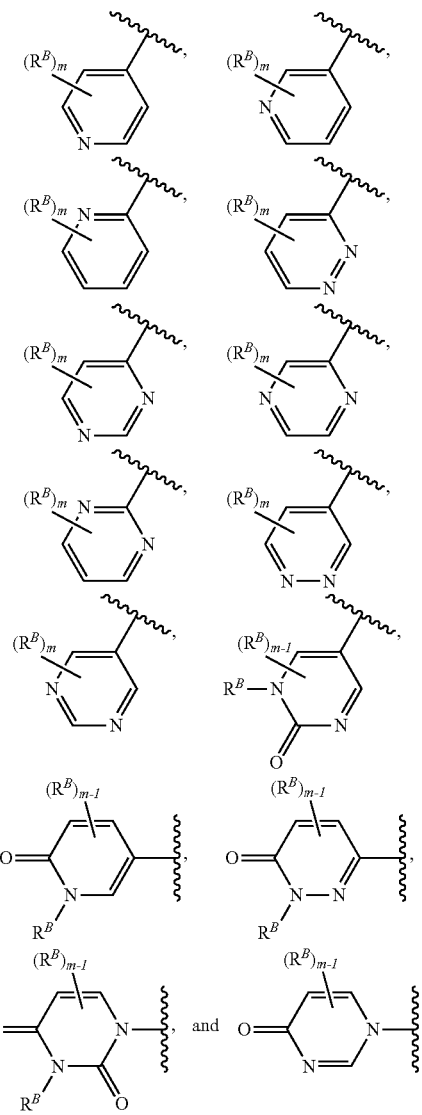

wherein each $R^B$ is independently selected from hydrogen, cyano, halogen, hydroxy, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$alkoxy, substituted or unsubstituted $C_3$-$C_7$cycloalkyl, substituted or unsubstituted $C_2$-$C_8$heterocycloalkyl, heteroaryl, substituted or unsubstituted heterocycloalkyl-$C_1$-$C_6$alkyl, substituted or unsubstituted $C_1$-$C_6$alkyl-aryl, substituted or unsubstituted $C_1$-$C_6$alkyl-heterocycloalkyl, substituted or unsubstituted $C_1$-$C_6$alkyl-heteroaryl, substituted or unsubstituted $C_1$-$C_6$alkoxy-aryl, substituted or unsubstituted $C_1$-$C_6$alkoxy-heterocycloalkyl, substituted or unsubstituted $C_1$-$C_6$alkoxy-heteroaryl, and $C_1$-$C_6$alkoxy substituted with hydroxy, $C_1$-$C_6$alkoxy, amino, mono-$C_1$-$C_6$alkylamino and di-$C_1$-$C_6$alkylamino; and m is 1, 2, 3, or 4; provided that at least one $R^B$ is substituted or unsubstituted $C_2$-$C_6$alkenyl.

In some embodiments, X is —$NR^7$—.

In some embodiments, $R^7$ is —$OR^5$, substituted or unsubstituted $C_1$-$C_6$alkyl, substituted or unsubstituted $C_1$-$C_6$haloalkyl, substituted or unsubstituted $C_1$-$C_6$heteroalkyl, or substituted or unsubstituted $C_3$-$C_8$cycloalkyl. In some embodiments, $R^7$ is —$OR^5$. In some embodiments, $R^7$ is substituted or unsubstituted $C_1$-$C_6$alkyl. In some embodiments, $R^7$ is substituted or unsubstituted $C_1$-$C_6$haloalkyl. In some embodiments, $R^7$ is substituted or unsubstituted $C_1$-$C_6$heteroalkyl. In some embodiments, $R^7$ is substituted or unsubstituted $C_3$-$C_8$cycloalkyl.

In some embodiments, $R^7$ is $C_3$-$C_8$cycloalkyl that is selected from cyclopropyl, cyclobutyl, cyclopentyl, cyclohexyl, cycloheptyl, and cyclooctyl. In some embodiments, $R^7$ is cyclopropyl. In some embodiments, $R^7$ is cyclobutyl. In some embodiments, $R^7$ is cyclopentyl. In some embodiments, $R^7$ is cyclohexyl.

In some embodiments, $R^7$ is $C_3$-$C_8$cycloalkyl that is selected from cyclopentenyl, cyclohexenyl, cycloheptenyl, and cyclooctenyl. In some embodiments, $R^7$ is cyclopentenyl. In some embodiments, $R^7$ is cyclohexenyl.

In some embodiments, $R^7$ is —$CH_3$, —$CH_2CH_2F$, or —$CF_3$. In some embodiments, $R^7$ is —$CH_3$. In some embodiments, $R^7$ is —$CH_2CH_2F$. In some embodiments, $R^7$ is —$CF_3$.

In some embodiments, $R^7$ is —$OCH_3$, —$OCH_2CH_3$, —$OCH_2CH_2OH$, or —$OCH_2CH_2OCH_3$. In some embodiments, $R^7$ is —$OCH_3OCH_2CH_2OCH_3$. In some embodiments, $R^7$ is —$OCH_2CH_3OCH_2CH_2OCH_3$. In some embodiments, $R^7$ is —$OCH_2CH_2OH$. In some embodiments, $R^7$ is —$OCH_2CH_2OCH_3$.

In some embodiments, a is 0. In some embodiments, a is 1. In some embodiments, b is 0. In some embodiments, b is 1. In some embodiments, a is 0 and b is 0. In some embodiments, a is 0 and b is 1. In some embodiments, a is 1 and b is 0. In some embodiments, a is 1 and b is 1.

In some embodiments, e is 0. In some embodiments, e is 1. In some embodiments, f is 0. In some embodiments, f is 1. In some embodiments, e is 0 and f is 0. In some embodiments, e is 0 and f is 1. In some embodiments, e is 1 and f is 0. In some embodiments, e is 1 and f is 1.

In some embodiments,

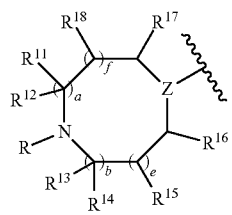

is

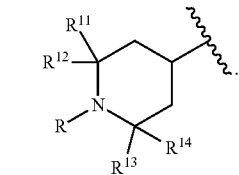

In some embodiments,

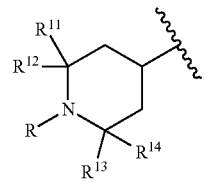

is

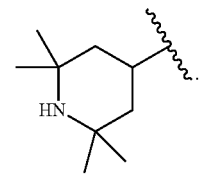

In some embodiments,

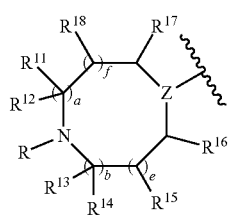

is

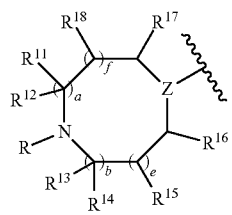

In some embodiments,

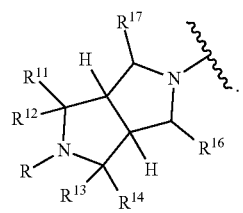

In some embodiments,

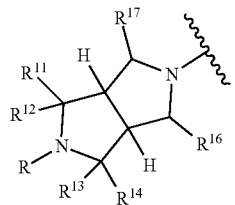

is

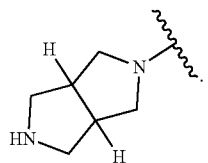

In some embodiments,

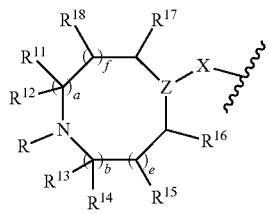

is

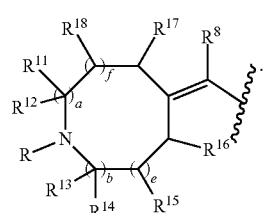

In some embodiments,

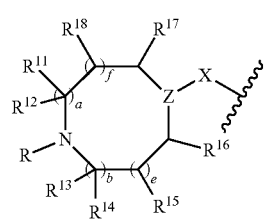

is

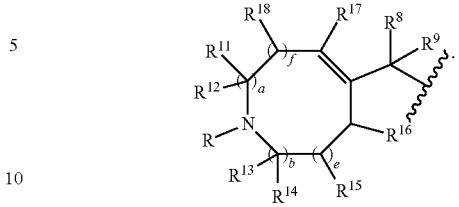

In some embodiments, the compound has the structure of Formula (IIa):

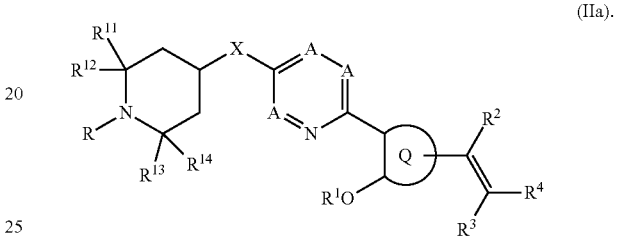

(IIa).

In some embodiments, each A is independently N or CH.

In some embodiments, ring Q is monocyclic aryl.

In some embodiments, X is —O—, —$NR^7$—, —$CR^8R^9$—, —C(=O)—, or —S—.

In some embodiments, R is selected from the group consisting of H, substituted or unsubstituted $C_1$-$C_6$alkyl, substituted or unsubstituted $C_1$-$C_6$fluoroalkyl, and substituted or unsubstituted $C_1$-$C_6$heteroalkyl.

In some embodiments, each $R^{11}$, $R^{12}$, $R^{13}$, and $R^{14}$ is independently selected from the group consisting of H, F, $OR^9$, substituted or unsubstituted $C_1$-$C_6$alkyl, substituted or unsubstituted $C_1$-$C_6$fluoroalkyl.

In some embodiments, each $R^{11}$, $R^{12}$, $R^{13}$, and $R^{14}$ is methyl.

In some embodiments, $R^1$ is H, D, substituted or unsubstituted substituted or unsubstituted $C_1$-$C_6$heteroalkyl, or substituted or unsubstituted $C_2$-$C_7$heterocycloalkyl.

In some embodiments, each $R^2$ and $R^3$ is independently H, D, halogen, or substituted or unsubstituted $C_1$-$C_6$alkyl. In some embodiments, each $R^2$ and $R^3$ is hydrogen. In some embodiments, $R^2$ is hydrogen and $R^3$ is $CH_3$. In some embodiments, $R^2$ is $CH_3$ and $R^3$ is hydrogen.

In some embodiments, $R^4$ is —C(=O)$R^5$, —C(=O)$OR^5$, —C(=O)N($R^6$)$_2$, —C=(O)N($OR^5$)($R^5$), —P(=O)($R^6$)$_2$, —P(=O)($R^6$)N($R^6$)$_2$, —S(=O)$R^6$, —S(=O)$_2R^6$, —S(=O)(=N$R^5$)$R^5$, —N($R^6$)C(=O)$R^6$, N($R^6$)S(=O)$R^6$, N($R^6$)S(=O)$_2R^6$, —C(=O)N($R^6$)S(=O)$_2R^6$, —N($R^6$)C(=O)N($R^6$)$_2$, substituted or unsubstituted cycloalkyl, substituted or unsubstituted heterocycloalkyl, substituted or unsubstituted aryl, or substituted or unsubstituted heteroaryl.

In some embodiments, two $R^6$ groups on the same nitrogen atom are taken together with the nitrogen atom to which they are attached to form substituted or unsubstituted $C_2$-$C_{10}$heterocycloalkyl.

In some embodiments, $R^4$ is —C(=O)OH, —C(=O)NH$_2$, —C(=O)NHCH$_3$, —C(=O)N(CH$_3$)$_2$, —C(=O)NH(OH), —C(=O)NH(OCH$_3$), —C(=O)N(CH$_3$)OH, C(=O)N(CH$_3$)OCH$_3$, —N(C(=O)CH$_3$)OH, —O—NHC(=O)CH$_3$), —P(=O)(OH)$_2$, —PH(=O)(OH), —S(=O)$_2$OH, —S(=O)OH, —S(=O)$_2$CH$_3$, —S(=O)CH$_3$, —S(=O)$_2$NH$_2$, —S(=O)NH$_2$, —S(=O)$_2$NH(CH$_3$), —S(=O)NH(CH$_3$), —S(=O)$_2$N(CH$_3$)$_2$, —S(=O)N(CH$_3$)$_2$, —S(=O)

(=NH)CH₃, —S(=O)(=NCH₃)CH₃, —NH(S(=O)₂ CH₃), —C(=O)NH(S(=O)₂CH₃), —C(=O)NH(S(=O)₂ N(CH₃)₂), —NHC(=O)NH(S(=O)₂CH₃), or —NHC (=O)NH(C(=O)CH₃).
In some embodiments, R⁴ is
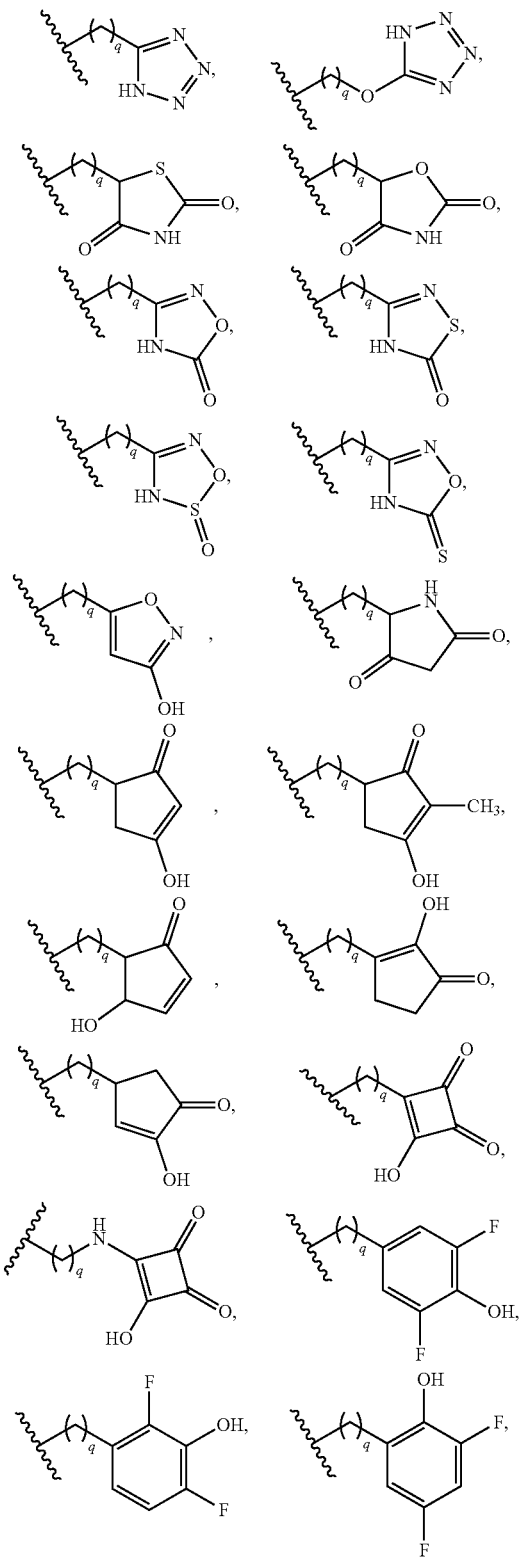
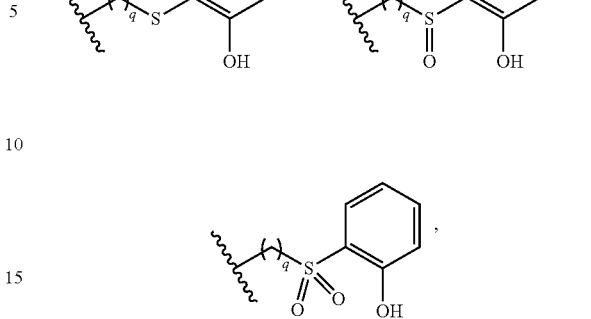
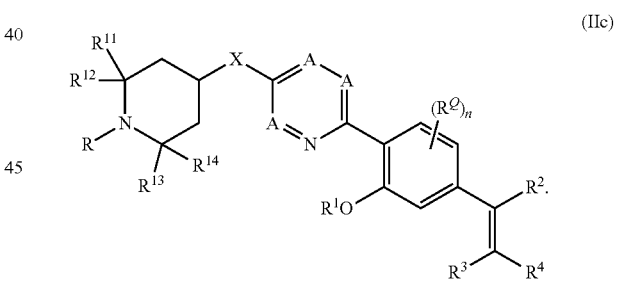
wherein q is 0, 1, or 2.
In some embodiments, the compound has the structure of Formula (IIb):
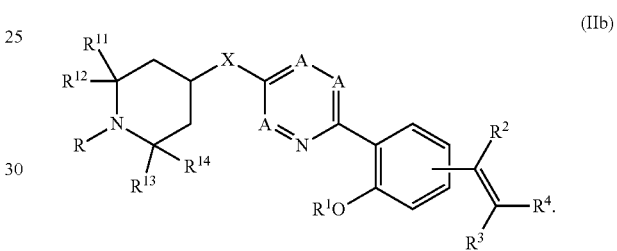
In some embodiments, the compound has the structure of Formula (IIc):
In some embodiments, the compound has the structure of Formula (IId):
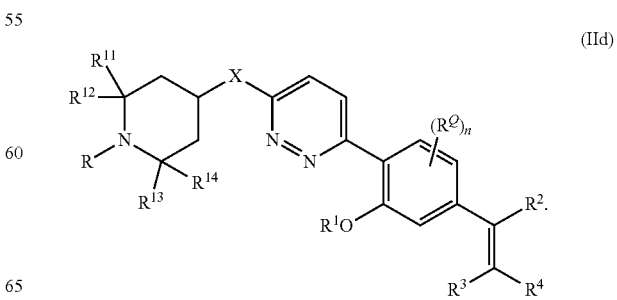

In some embodiments, the compound has the structure of Formula IIe):

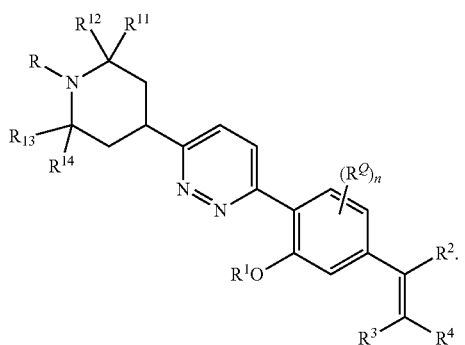

(IIe)

Any combination of the groups described above for the various variables is contemplated herein. Throughout the specification, groups and substituents thereof are chosen by one skilled in the field to provide stable moieties and compounds.

In one aspect, described herein is a compound of Formula (III), or a pharmaceutically acceptable salt or solvate thereof:

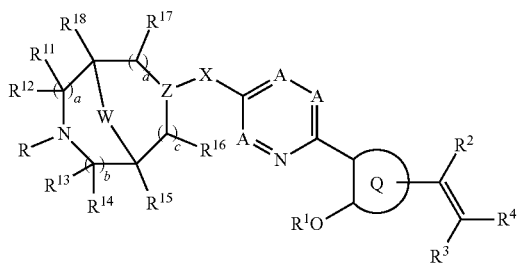

Formula (III)

wherein,
each A is independently N or $CR^4$;
each $R^4$ is independently selected from hydrogen, deuterium, halogen, —CN, —OH, —$OR^5$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, and substituted or unsubstituted $C_2$-$C_7$heterocycloalkyl;
ring Q is substituted monocyclic aryl or substituted monocyclic heteroaryl;
X is absent, —O—, —S—, or —$NR^7$—;
each $R^1$ and $R^5$ is independently hydrogen, deuterium, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, or substituted or unsubstituted $C_2$-$C_7$heterocycloalkyl;
each $R^2$ and $R^3$ is independently hydrogen, deuterium, substituted or unsubstituted $C_1$-$C_4$alkyl, substituted or unsubstituted $C_1$-$C_6$haloalkyl, or substituted or unsubstituted $C_3$-$C_8$cycloalkyl;
$R^4$ is —C(=O)$R^5$, —C(=O)$OR^5$, —C(=O)N($R^6$)$_2$, —S(=O)$R^6$, or —S(=O)$_2R^6$;

each $R^6$ is independently hydrogen, deuterium, substituted or unsubstituted $C_1$-$C_6$alkyl, substituted or unsubstituted $C_1$-$C_6$haloalkyl, substituted or unsubstituted aryl, substituted or unsubstituted monocyclic heteroaryl, —$OR^5$, —N($R^5$)$_2$, or —$CH_2OR^5$; or
two $R^6$ groups on the same nitrogen atom are taken together with the nitrogen atom to which they are attached to form substituted or unsubstituted $C_2$-$C_8$heterocycloalkyl;
$R^7$ is hydrogen, —$OR^5$, —N($R^5$)$_2$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, or substituted or unsubstituted heteroaryl;
Z is $CR^8$;
$R^8$ is hydrogen, deuterium, substituted or unsubstituted $C_1$-$C_6$alkyl, substituted or unsubstituted $C_1$-$C_6$haloalkyl, or substituted or unsubstituted $C_1$-$C_6$heteroalkyl;
W is substituted or unsubstituted $C_1$-$C_4$alkylene, substituted or unsubstituted $C_2$-$C_4$alkenylene, substituted or unsubstituted $C_1$-$C_4$heteroalkylene, or substituted or unsubstituted $C_3$-$C_6$cycloalkylene;
R is selected from the group consisting of hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, substituted or unsubstituted $C_2$-$C_7$heterocycloalkyl, substituted or unsubstituted aryl, and substituted or unsubstituted heteroaryl;
$R^{11}$, $R^{12}$, $R^{13}$, $R^{14}$, $R^{15}$, $R^{16}$, $R^{17}$, and $R^{18}$ are each independently selected from the group consisting of hydrogen, F, —$OR^5$, substituted or unsubstituted $C_1$-$C_6$alkyl, substituted or unsubstituted $C_1$-$C_6$fluoroalkyl, and substituted or unsubstituted $C_1$-$C_6$heteroalkyl;
a and b are each independently 0 or 1; and
c and d are each independently 0 or 1.

In some embodiments, the compound of Formula (III) has the structure of Formula (IIIa):

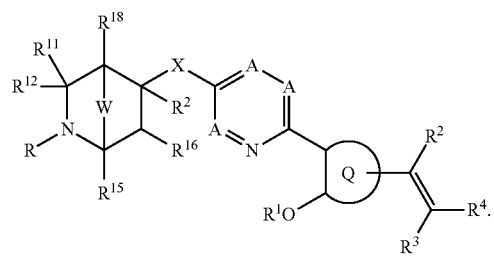

Formula (IIIa)

In some embodiments, the compound of Formula (III) has the structure of Formula (IIIb):

Formula (IIIb)

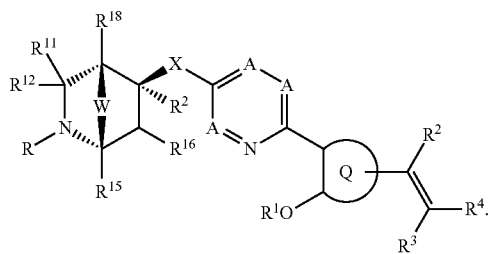

Formula (IIIf)

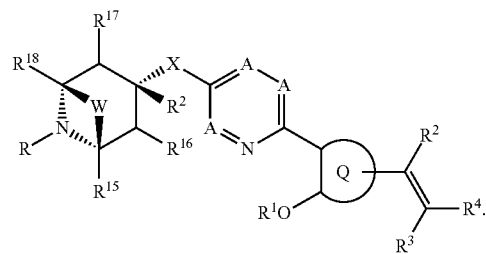

In some embodiments, the compound of Formula (III) has the structure of Formula (IIIc):

Formula (IIIc)

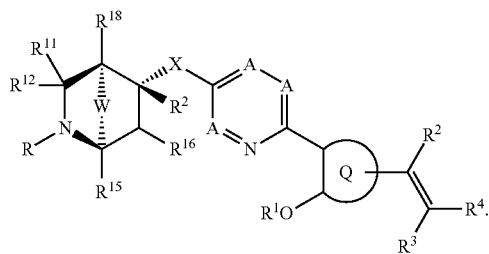

In some embodiments, the compound of Formula (III) has the structure of Formula (IIId):

Formula (IIId)

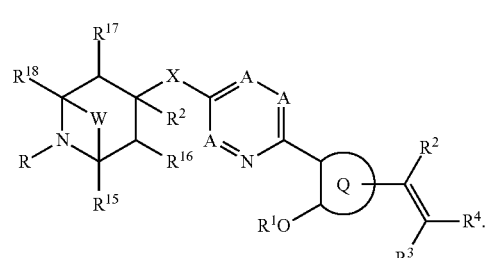

In some embodiments, the compound of Formula (III) has the structure of Formula (IIIe):

Formula (IIIe)

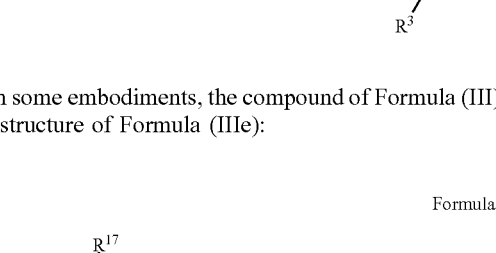

In some embodiments, the compound of Formula (III) has the structure of Formula (IIIf):

In some embodiments, the compound of Formula (III) is a single isomer substantially free of other isomers.

In some embodiments,

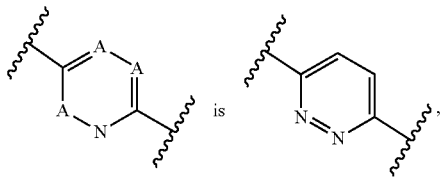

is

In some embodiments,

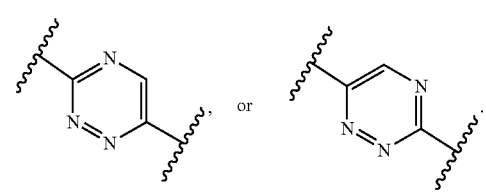

is

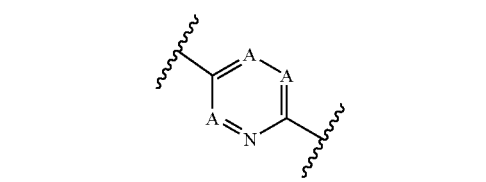

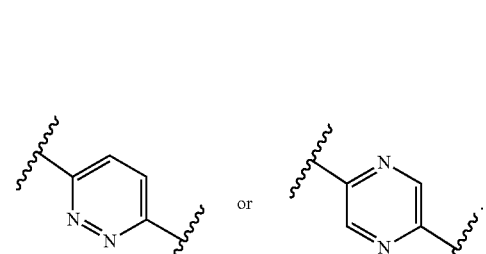

In some embodiments,

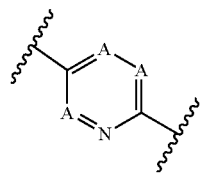

is

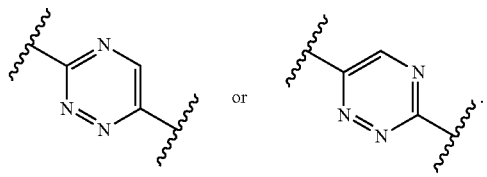 [SMILES: *c1cnc(*)nn1 ; *c1cnc(*)nn1]

In some embodiments,

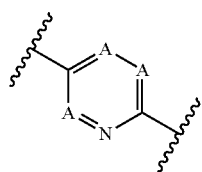

is

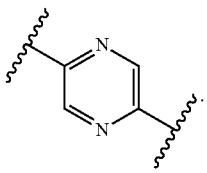 [SMILES: *c1cnc(*)cn1]

In some embodiments,

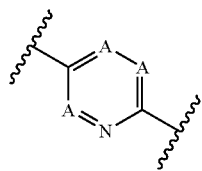

is

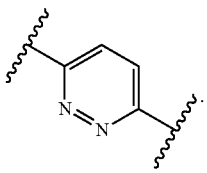 [SMILES: *c1ccc(*)nn1]

In some embodiments, ring Q is substituted aryl.

In some embodiments, ring Q is

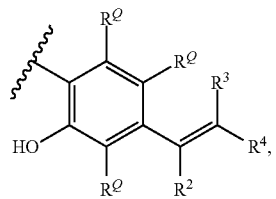

wherein each $R^Q$ is independently selected from hydrogen, deuterium, —F, —CN, —OH, —CH₃, —CH₂CH₃, —CH₂CH₂CH₃, —CH(CH₃)₂, —CF₃, —OCH₃, —OCH₂CH₃, —CH₂OCH₃, —OCH₂CH₂CH₃, and —OCH(CH₃)₂.

In some embodiments, ring Q is substituted heteroaryl. In some embodiments, ring Q is substituted 5- or 6-membered monocyclic heteroaryl. In some embodiments, ring Q is substituted 6-membered monocyclic heteroaryl.

In some embodiments, ring Q is 6-membered monocyclic heteroaryl selected from:

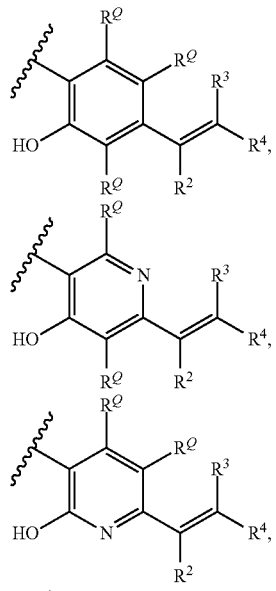

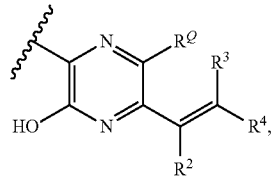

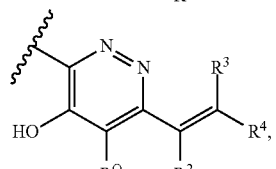

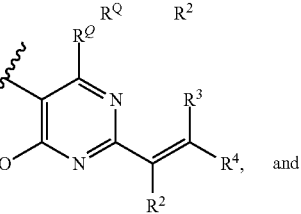

and

-continued

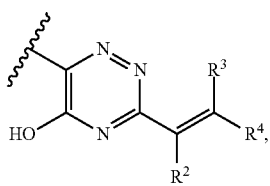

-continued

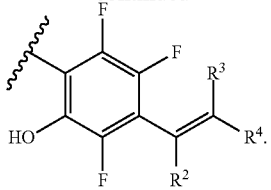

wherein each $R^Q$ is independently selected from hydrogen, deuterium, —F, —Cl, —CN, —OH, —CH$_3$, —CH$_2$CH$_3$, —CH$_2$CH$_2$CH$_3$, —CH(CH$_3$)$_2$, —CF$_3$, —OCH$_3$, —OCH$_2$CH$_3$, —CH$_2$OCH$_3$, —OCH$_2$CH$_2$CH$_3$, and —OCH(CH$_3$)$_2$.

In some embodiments, each $R^Q$ is independently hydrogen, —F, —Cl, —CN, —OH, —CH$_3$, —CF$_3$, or —OCH$_3$. In some embodiments, each $R^Q$ is independently hydrogen, —F, —Cl, —CN, —CF$_3$, or —OCF$_3$. In some embodiments, each $R^Q$ is independently hydrogen, —F, —CF$_3$, or —OCF$_3$. In some embodiments, each $R^Q$ is independently hydrogen, or —F.

In some embodiments, ring Q is selected from:

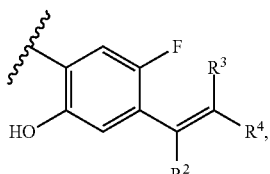

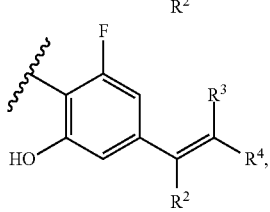

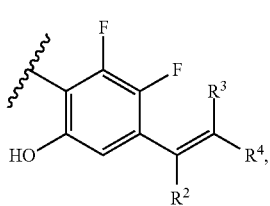

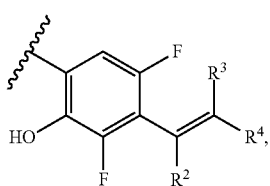

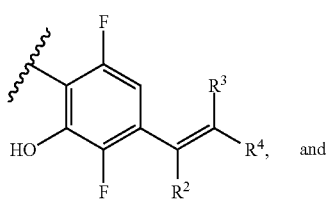

In some embodiments, each $R^2$ and $R^3$ is independently hydrogen, deuterium, or C$_1$-C$_4$alkyl. In some embodiments, each $R^2$ and $R^3$ is independently hydrogen, —CH$_3$, —CH$_2$CH$_3$, —CH(CH$_3$)$_2$, —CF$_3$, or cyclopropyl. In some embodiments, each $R^2$ and $R^3$ is independently hydrogen, —CH$_3$, —CH(CH$_3$)$_2$, —CF$_3$, or cyclopropyl. In some embodiments, each $R^2$ and $R^3$ is independently hydrogen, —CH$_3$, or —CF$_3$. In some embodiments, each $R^2$ and $R^3$ is hydrogen.

In some embodiments, $R^4$ is —C(=O)R$^5$, —C(=O)OR$^5$, or —C(=O)N(R$^6$)$_2$. In some embodiments, $R^4$ is —C(=O)CH$_3$, —C(=O)CH$_2$CH$_3$, —C(=O)OCH$_3$, —C(=O)OCH$_2$CH$_3$, —C(=O)NH$_2$, —C(=O)NHCH$_3$, or —C(=O)N(CH$_3$)$_2$. In some embodiments, $R^4$ is —C(=O)NHCH$_3$ or —C(=O)N(CH$_3$)$_2$. In some embodiments, $R^4$ is —C(=O)NHCH$_3$.

In some embodiments, $R^1$ is hydrogen.

In some embodiments, W is substituted or unsubstituted C$_1$-C$_3$ alkylene. In some embodiments, W is —CH$_2$—. In some embodiments, W is —CH$_2$CH$_2$—. In some embodiments, W is —CH$_2$CH$_2$CH$_2$—.

In some embodiments, W is substituted or unsubstituted C$_1$-C$_2$ heteroalkylene. In some embodiments, W is —CH$_2$OCH$_2$—. In some embodiments, W is —CH$_2$O—, wherein oxygen atom in —CH$_2$O— is attached to a carbon atom having $R^{18}$ group.

In some embodiments, W is substituted or unsubstituted C$_3$-C$_8$ cycloalkylene or substituted or unsubstituted C$_2$-C$_3$ alkenylene. In some embodiments, W is substituted or unsubstituted C$_3$-C$_8$ cycloalkylene. In some embodiments, W is cyclopropylene. In some embodiments, W is substituted or unsubstituted C$_2$-C$_3$ alkenylene. In some embodiments, W is —CH=CH—.

In some embodiments, R is hydrogen, substituted or unsubstituted C$_1$-C$_4$ alkyl, substituted or unsubstituted C$_1$-C$_4$ fluoroalkyl, substituted or unsubstituted C$_1$-C$_4$ heteroalkyl, substituted or unsubstituted C$_3$-C$_5$ cycloalkyl, or substituted or unsubstituted C$_2$-C$_4$ heterocycloalkyl. In some embodiments, R is hydrogen, —CH$_3$, —CH$_2$CH$_3$, —CH$_2$CH$_2$CH$_3$, —CH(CH$_3$)$_2$, —CH$_2$OH, —CH$_2$CH$_2$OH, —CH$_2$CH$_2$CH$_2$OH, —C(OH)(CH$_3$)$_2$, —CH$_2$CN, —CH$_2$C(=O)OCH$_3$, —CH$_2$C(=O)OCH$_2$CH$_3$, —CH$_2$C(=O)NHCH$_3$, —CH$_2$C(=O)N(CH$_3$)$_2$, —CH$_2$NH$_2$, —CH$_2$NHCH$_3$, —CH$_2$N(CH$_3$)$_2$, —CH$_2$F, —CHF$_2$, —CF$_3$, cyclopropyl, cyclobutyl, oxetanyl, aziridinyl, or azetidinyl. In some embodiments, R is hydrogen, —CH$_3$, —CH$_2$CH$_3$, —CH$_2$OH, —CH$_2$CH$_2$OH, —CH$_2$CN, —CH$_2$F, —CHF$_2$, —CF$_3$, cyclopropyl, or oxetanyl. In some embodiments, R is —CH$_3$, —CH$_2$CH$_3$, —CH$_2$F, —CHF$_2$, or —CF$_3$. In some embodiments, R is hydrogen.

In some embodiments, $R^{11}$, $R^{12}$, and $R^{16}$ are hydrogen.
In some embodiments, $R^{16}$ and $R^{17}$ are hydrogen.
In some embodiments, $R^8$ is hydrogen, —CH$_3$, or —OCH$_3$. In some embodiments, $R^8$ is hydrogen.
In some embodiments, X is —O—. In some embodiments, X is —S—. In some embodiments, X is —NR$^7$—.

In some embodiments, R⁷ is hydrogen, —CH₃, —CH₂CH₃, —CH(CH₃)₂, —CH₂F, —CHF₂, —CF₃, cyclopropyl, or oxetanyl. In some embodiments, R⁷ is hydrogen, —CH₃, —CH₂CH₃, —CH(CH₃)₂, —CF₃, cyclopropyl, or oxetanyl. In some embodiments, R⁷ is hydrogen, —CH₃, —CH(CH₃)₂, cyclopropyl, or oxetanyl. In some embodiments, R⁷ is hydrogen, —CH₃, or cyclopropyl.

In some embodiments, each R⁴ is independently hydrogen, F, Cl, —CN, —CH₃, —CH₂CH₃, —CH₂CH₂CH₃, —CH(CH₃)₂, —OH, —OCH₃, —OCH₂CH₃, —OCF₃, —CH₂F, —CHF₂, or —CF₃. In some embodiments, each R⁴ is independently hydrogen, F, Cl, —CN, —CH₃, —OH, —OCH₃, —OCF₃, —CH₂F, —CHF₂, or —CF₃. In some embodiments, each R⁴ is independently hydrogen, F, Cl, —CN, —CH₃, or —OCH₃. In some embodiments, each R⁴ is independently hydrogen, F, Cl, or —CH₃. In some embodiments, each R⁴ is hydrogen.

In some embodiments, each R¹⁵ and R¹⁸ is independently selected from hydrogen, deuterium, F, —OR¹, substituted or unsubstituted C₁-C₃ alkyl, substituted or unsubstituted C₁-C₃ fluoroalkyl, and substituted or unsubstituted C₁-C₃ heteroalkyl. In some embodiments, each R¹⁵ and R¹⁸ is independently selected from hydrogen, deuterium, F, —CH₃, —CH₂OH, —OCH₂CN, —OH, —OCH₃, —OCH₂CN, —OCF₃, —CH₂F, —CHF₂, and —CF₃. In some embodiments, each R¹⁵ and R¹⁸ is independently selected from hydrogen, deuterium, —CH₃, —OCH₃, —OCF₃, —CH₂F, —CHF₂, and —CF₃. In some embodiments, each R¹⁵ and R¹⁸ is independently selected from hydrogen, deuterium, —CH₃, and —OCH₃. In some embodiments, R¹⁵ and R¹⁸ are both —CH₃. In some embodiments, R¹⁵ and R¹⁸ are both —OCH₃. In some embodiments, R¹⁵ is hydrogen and R¹⁸ is —CH₃. In some embodiments, R¹⁵ is —CH₃ and R¹⁸ is hydrogen. In some embodiments, R¹⁵ and R¹⁸ are both hydrogen. In some embodiments, R¹⁵ and R¹⁸ are both deuterium.

In some embodiments, exemplary SMSM compounds are selected from Table 1-Table 5 below.

TABLE 1

Exemplary SMSM compounds

| Structure | Name | NMR | MS |
| --- | --- | --- | --- |
| 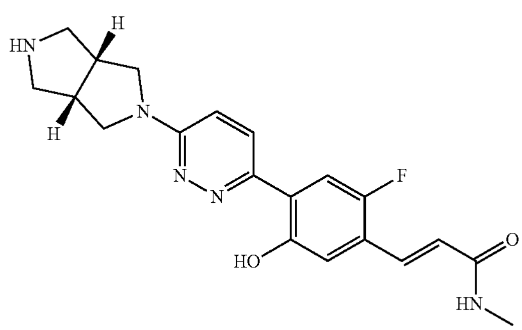 [SMILES: CNC(=O)/C=C/c1cc(O)c(-c2ccc(N3C[C@H]4CNC[C@H]4C3)nn2)cc1F] | (E)-3-(2-fluoro-4-(6-((3aR,6aS)-hexahydropyrrolo[3,4-c]pyrrol-2(1H)-yl)pyridazin-3-yl)-5-hydroxyphenyl)-N-methylacrylamide | ¹H NMR (500 MHz, DMSO-d₆) δ 8.25 (d, J = 9.8 Hz, 1H), 8.17 (d, J = 4.7 Hz, 1H), 7.85 (d, J = 12.3 Hz, 1H), 7.42 (d, J = 15.9 Hz, 1H), 7.19 (d, J = 9.8 Hz, 1H), 7.14 (d, J = 0 6.7 Hz, 1H), 6.71 (d, J = 15.9 Hz, 1H), 3.80-3.76 (m, 2H), 3.43-3.38 (m, 2H), 2.99-2.81 (m, 4H), 2.75-2.69 (m, 3H), 2.69-0 2.63 (m, 2H). | 384.1 |
| 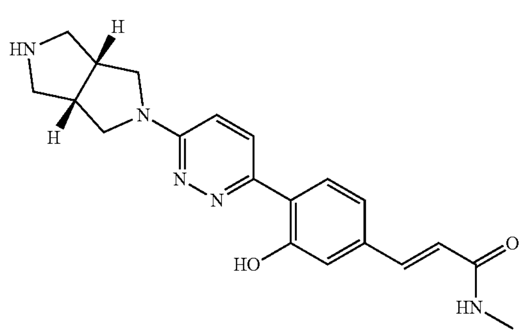 [SMILES: CNC(=O)/C=C/c1ccc(-c2ccc(N3C[C@H]4CNC[C@H]4C3)nn2)c(O)c1] | (E)-3-(4-(6-((3aR,6aS)-hexahydropyrrolo[3,4-c]pyrrol-2(1H)-yl)pyridazin-3-yl)-3-hydroxyphenyl)-N-methylacrylamide | ¹H NMR (500 MHz, DMSO-d₆) δ 8.23 (d, J = 9.8 Hz, 1H), 8.06 (d, J = 4.8 Hz, 1H), 7.90 (d, J = 8.2 Hz, 1H), 7.36 (d, J = 15.7 Hz, 1H), 7.20 (d, J = 9.8 Hz, 1H), 7.14-7.03 (m, 2H), 6.63 (d, J = 15.8 Hz, 1H), 3.80-3.75 (m, 2H), 3.41-3.35 (m, 4H), 3.01-2.83 (m, 4H), 2.75-2.62 (m, 5H). | 366.1 |
| 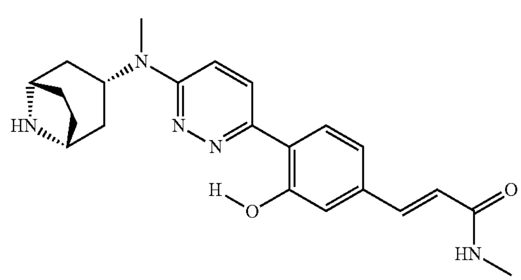 | (E)-3-(4-(6-(((1R,3s,5S)-8-azabicyclo[3.2.1]octan-3-yl)(methyl)amino)pyridazin-3-yl)-3-hydroxyphenyl)-N-methylacrylamide | ¹H NMR (400 MHz, DMSO-d₆) δ 8.20 (d, J = 10.0 Hz, 1H), 8.08 (d, J = 4.8 Hz, 1H), 7.91 (d, J = 8.1 Hz, 1H), 7.42-7.31 (m, 2H), 7.12 (d, J = 8.3 Hz, 2H), 6.63 (d, J = 15.8 Hz, 1H), 5.04-4.77 (m, 1H), 3.52 (s, 2H), 2.94 (s, 3H), 2.71 (d, J = 4.6 Hz, 3H), 1.80 (s, 6H), 1.60-1.46 (m, 2H). | 394.3 |

TABLE 1-continued

Exemplary SMSM compounds

| Structure | Name | NMR | MS |
|---|---|---|---|
| 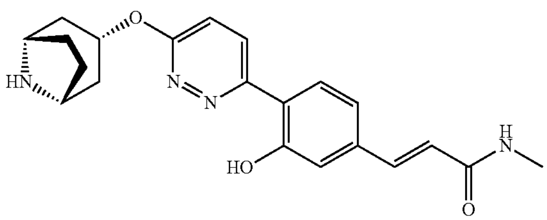 | (E)-3-(4-(6-(((1R,3s,5S)-8-azabicyclo[3.2.1]octan-3-yl)oxy)pyridazin-3-yl)-3-hydroxyphenyl)-N-methylacrylamide | $^1$H NMR (400 MHz, DMSO-d$_6$) δ 12.87 (br, 1H), 8.40 (d, J = 10.0 Hz, 1H), 8.13-8.09 (m, 1H), 7.97 (d, J = 8.8 Hz, 1H), 7.39 (d, J = 5.2 Hz, 1H), 7.36 (s, 1H), 7.18-7.14 (m, 2H), 6.65 (d, J = 15.6 Hz, 1H), 5.55-05.45 (m, 1H), 3.52 (s, 2H), 2.71 (d, J = 4.4 Hz, 3H), 2.18-2.14 (m, 2H), 1.73-1.70 (m, 4H), 1.59 (t, J = 10.4 Hz, 2H). | 381.2 |
| 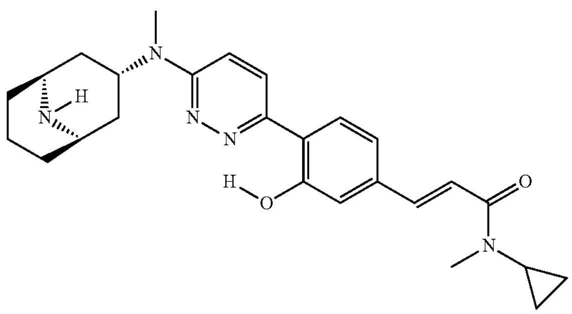 [SMILES: CN(C(=O)/C=C/c1ccc(-c2ccc(N(C)[C@@H]3C[C@H]4CCC[C@@H](C3)N4)nn2)c(O)c1)C1CC1] | (E)-3-(4-(6-(((1R,3s,5S)-9-azabicyclo[3.3.1]nonan-3-yl)(methyl)amino)pyridazin-3-yl)-3-hydroxyphenyl)-N-cyclopropyl-N-methylacrylamide | $^1$H NMR (500 MHz, DMSO-d$_6$) δ 13.63 (s, 1H), 8.84-8.68 (m, 1H), 8.28 (d, J = 10.0 Hz, 1H), 7.93 (d, J = 8.3 Hz 1H), 7.54-7.32 (m, 3H), 7.30-7.11 (m, 2H), 5.87-5.65 (m, 1H), 3.75 (s, 2H), 2.94 (d, J = 25.1 Hz, 7H), 2.39-2.21 (m, 2H), 2.09-1.83 (m, 7H), 1.75 (s, 1H), 0.95 (s, 2H), 0.75 (s, 2H). | 448.3 |
| 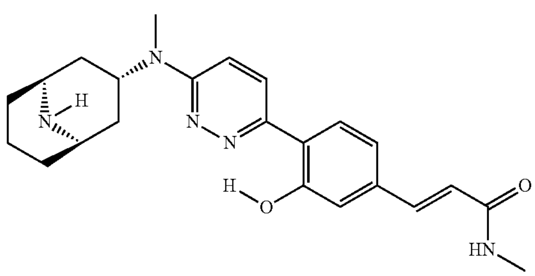 [SMILES: CNC(=O)/C=C/c1ccc(-c2ccc(N(C)[C@@H]3C[C@H]4CCC[C@@H](C3)N4)nn2)c(O)c1] | (E)-3-(4-(6-(((1R,3s,5S)-9-azabicyclo[3.3.1]nonan-3-yl)(methyl)amino)pyridazin-3-yl)-3-hydroxyphenyl)-N-methylacrylamide | $^1$H NMR (500 MHz, DMSO-d$_6$) δ 8.22 (d, J = 10.0 Hz, 1H), 8.06 (d, J = 4.7 Hz, 1H), 7.90 (d, J = 8.1 Hz, 1H), 7.39-7.31 (m, 2H), 7.12 (d, J = 9.2 Hz, 2H), 6.63 (d, J = 15.7 Hz, 1H), 5.89-5.41 (m, 1H), 3.19 (s, 2H), 2.93 (s, 3H), 2.71 (d, J = 4.7 Hz, 3H), 2.07-1.88 (m, 3H), 1.88-1.76 (m, 2H), 1.74-1.58 (m, 5H). | 408.3 |
| 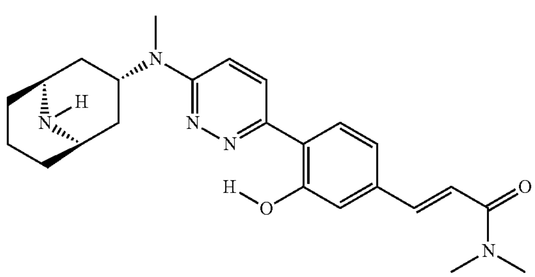 [SMILES: CN(C)C(=O)/C=C/c1ccc(-c2ccc(N(C)[C@@H]3C[C@H]4CCC[C@@H](C3)N4)nn2)c(O)c1] | (E)-3-(4-(6-(((1R,3s,5S)-9-azabicyclo[3.3.1]nonan-3-yl)(methyl)amino)pyridazin-3-yl)-3-hydroxyphenyl)-N,N-dimethylacrylamide | $^1$H NMR (500 MHz, DMSO-d$_6$) δ 13.68 (s, 1H), 8.86-8.66 (m, 1H), 8.29 (d, J = 10.0 Hz, 1H), 7.92 (d, J = 8.3 Hz, 1H), 7.45-7.35 (m, 2H), 7.32 (s, 1H), 7.28-7.20 (m, 2H), 5.84-5.68 (m, 1H), 3.73 (s, 2H), 3.17 (s, 3H), 2.95 (d, J = 15.2 Hz, 6H), 2.38-2.29 (m, 2H), 2.10-1.84 (m, 7H), 1.82-1.71 (m, 1H). | 422.2 |
| 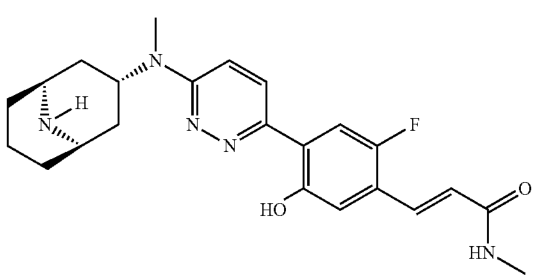 [SMILES: CNC(=O)/C=C/c1cc(O)c(-c2ccc(N(C)[C@@H]3C[C@H]4CCC[C@@H](C3)N4)nn2)cc1F] | (E)-3-(4-(6-(((1R,3s,5S)-9-azabicyclo[3.3.1]nonan-3-yl)(methyl)amino)pyridazin-3-yl)-2-fluoro-5-hydroxyphenyl)-N-methylacrylamide | $^1$H NMR (500 MHz, DMSO-d$_6$) δ 13.44 (s, 1H), 8.24 (d, J = 9.8 Hz, 1H), 8.21-8.13 (m, 1H), 7.85 (d, J = 12.1 Hz, 1H), 7.43 (d, J = 15.9 Hz, 1H), 7.30 (d, J = 9.9 Hz, 1H), 7.15 (d, J = 6.6 Hz, 1H), 6.72 (d, J = 15.9 Hz, 1H), 5.73-5.60 (m, 1H), 3.19 (s, 2H), 2.93 (s, 3H), 2.72 (d, J = 4.7 Hz, 3H), 2.03-1.92 (m, 3H), 1.87 ? 1.76 (m, 2H), 1.73-1.61 (m, 5H). | 426.2 |

TABLE 1-continued

Exemplary SMSM compounds

| Structure | Name | NMR | MS |
|---|---|---|---|
| 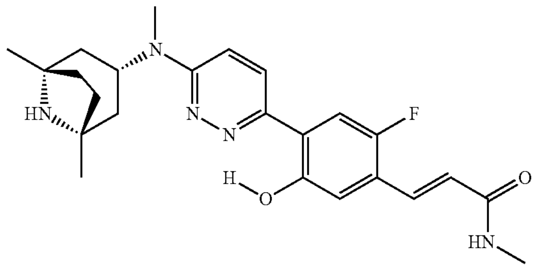 | (E)-3-(4-(6-(((1R,3s,5S)-1,5-dimethyl-8-azabicyclo[3.2.1]octan-3-yl)methyl)amino)pyridazin-3-yl)-2-fluoro-5-hydroxyphenyl)-N-methylacrylamide | $^1$H NMR (500 MHz, DMSO-d$_6$) δ 13.46 (s, 1H), 8.23 (d, J = 10.0 Hz, 1H), 8.17 (d, J = 4.8 Hz, 1H), 7.85 (d, J = 12.3 Hz, 1H), 7.43 (d, J = 15.9 Hz, 1H), 7.36 (d, J = 10.0 Hz, 1H), 7.15 (d, J = 6.7 Hz, 1H), 6.72 (d, J = 15.9 Hz, 1H), 5.01-4.88 (m, 1H), 2.94 (s, 3H), 2.72 (d, J = 4.7 Hz, 3H), 1.83-1.76 (m, 2H), 1.57-1.41 (m, 6H), 1.17 (s, 6H). | 440.3 |
| 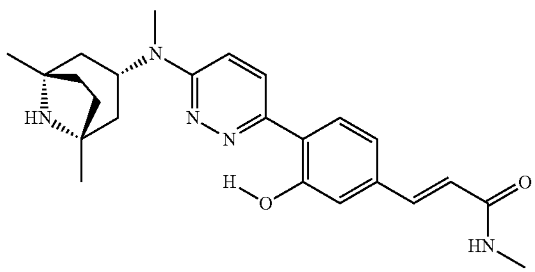 | (E)-3-(4-(6-(((1R,3s,5S)-1,5-dimethyl-8-azabicyclo[3.2.1]octan-3-yl)(methyl)amino)pyridazin-3-yl)-3-hydroxyphenyl)-N-methylacrylamide | $^1$H NMR (500 MHz, DMSO-d$_6$) δ 8.26-8.16 (m, 1H), 8.07 (d, J = 4.9 Hz, 1H), 7.90 (d, J = 8.2 Hz, 1H), 7.42-7.30 (m, 2H), 7.16-7.02 (m, 2H), 6.62 (d, J = 15.8 Hz, 1H), 5.00-4.83 (m, 1H), 2.93 (s, 3H), 2.71 (d, J = 4.7 Hz, 3H), 1.87-1.72 (m, 2H), 1.56-1.40 (m, 6H), 1.17 (s, 6H). | 422.3 |
| 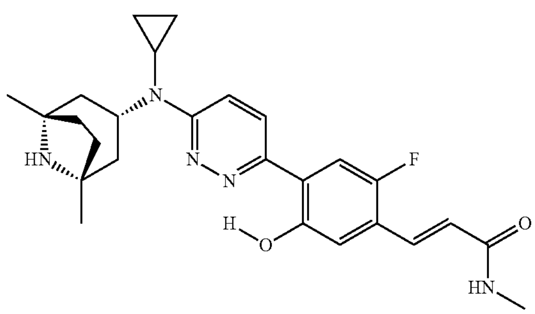 | (E)-3-(4-(6-(cyclopropyl((1R,3s,5S)-1,5-dimethyl-8-azabicyclo[3.2.1]octan-3-yl)amino)pyridazin-3-yl)-2-fluoro-5-hydroxyphenyl)-N-methylacrylamide | $^1$H NMR (500 MHz, DMSO-d$_6$) δ 13.37 (s, 1H), 8.27 (d, J = 9.8 Hz, 1H), 8.18-8.15 (m, 1H), 7.85 (d, J = 12.3 Hz, 1H), 7.55 (d, J = 9.8 Hz, 1H), 7.43 (d, J = 15.9 Hz, 1H), 7.16 (d, J = 6.7 Hz, 1H), 6.73 (d, J = 15.9 Hz, 1H), 4.81-4.67 (m, 1H), 2.72 (d, J = 4.7 Hz, 3H), 1.85-1.68 (m, 6H), 1.51-1.43 (m, 2H), 1.17 (s, 6H), 1.01-0.96 (m, 2H), 0.70-0.62 (m, 2H). | 466.0 |
| 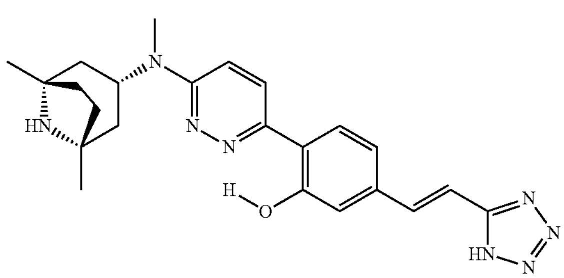 [SMILES: CN(c1ccc(-c2ccc(/C=C/c3nnn[nH]3)cc2O)nn1)[C@H]1C[C@]2(C)CC[C@](C)(C1)N2] | 5-((E)-2-(1H-tetrazol-5-yl)vinyl)-2-(6-(((1R,3s,5S)-1,5-dimethyl-8-azabicyclo[3.2.1]octan-3-yl)(methyl)amino)pyridazin-3-yl)phenol | $^1$H NMR (500 MHz, DMSO-d$_6$) δ 13.65 (s, 1H), 8.19 (d, J = 9.9 Hz, 1H), 7.83 (d, J = 8.3 Hz, 1H), 7.35 (d, J = 10.0 Hz, 1H), 7.30-7.21 (m, 2H), 7.18-7.14 (m, 1H), 7.08 (d, J = 1.8 Hz, 1H), 4.99-4.82 (m, 1H), 2.93 (s, 3H), 1.90-1.77 (m, 2H), 1.54-1.48 (m, 6H), 1.17 (s, 6H). | 433.1 |
| | (E)-3-(4-(6-(cyclopropyl((1R,3s,5S)-1,5-dimethyl-9-azabicyclo[3.3.1]nonan-3-yl)amino)pyridazin-3-yl)-2-fluoro-5-hydroxyphenyl)-N-methylacrylamide | $^1$H NMR (500 MHz, DMSO-d$_6$) δ 13.12 (s, 1H), 8.85 (d, J = 108.5 Hz, 1H), 8.31 (d, J = 9.9 Hz, 1H), 8.24-8.15 (m, 1H), 7.86 (d, J = 12.2 Hz, 1H), 7.60 (d, J = 9.8 Hz, 1H), 7.43 (d, J = 15.9 Hz, 1H), 7.17 (d, J = 6.6 Hz, 1H), 6.73 (d, J = 15.9 Hz, 1H), 5.60-5.45 (m, 1H), 2.72 (d, J = 4.6 Hz, 3H), 2.23 (t, J = 13.1 Hz, 2H), 2.18-2.06 (m, 3H), 1.92 (d, J = 13.4 Hz, 2H), 1.80-1.63 (m, 3H), 1.38 (s, 6H), 1.03 (d, J = 5.9 Hz, 2H), 0.73 (s, 2H). | 480.1 |

TABLE 1-continued

Exemplary SMSM compounds

| Structure | Name | NMR | MS |
|---|---|---|---|
| 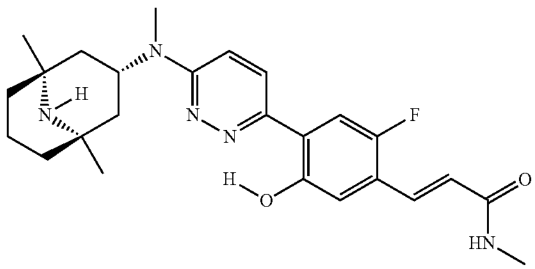 [SMILES: CNC(=O)/C=C/c1cc(O)c(-c2ccc(N(C)[C@H]3C[C@]4(C)CCC[C@](C)(C3)N4)nn2)cc1F] | (E)-3-(4-(6-(((1R,3s,5S)-1,5-dimethyl-9-azabicyclo[3.3.1]nonan-3-yl)(methyl)amino)pyridazin-3-yl)-3-hydroxyphenyl)-N-methylacrylamide | $^1$H NMR (500 MHz, DMSO-d$_6$) δ 13.57 (s, 1H), 8.26 (d, J = 9.9 Hz, 1H), 7.92 (d, J = 8.2 Hz, 1H), 7.43-7.29 (m, 2H), 7.17-7.06 (m, 2H), 6.63 (d, J = 15.8 Hz, 1H), 5.95-5.78 (m, 1H), 2.94 (s, 3H), 2.71 (d, J=4.7 Hz, 3H), 2.21-2.06 (m, 1H), 2.05-1.84 (m, 6H), 1.82-1.65 (m, 3H), 1.32 (s, 6H). | 436.3 |
| 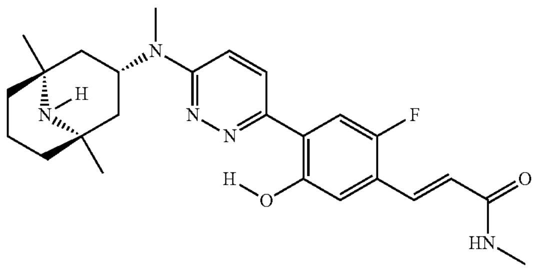 [SMILES: CNC(=O)/C=C/c1cc(O)c(-c2ccc(N(C)[C@H]3C[C@]4(C)CCC[C@](C)(C3)N4)nn2)cc1F] | (E)-3-(4-(6-(((1R,3s,5S)-1,5-dimethyl-9-azabicyclo[3.3.1]nonan-3-yl)(methyl)amino)pyridazin-3-yl)-2-fluoro-5-hydroxyphenyl)-N-methylacrylamide | (d, J = 9.8 Hz, 1H), 7.79 (d, J = 12.4 Hz, 1H), 7.46 (d, J = 15.8 Hz, 1H), 7.27 (d, J = 10.0 Hz, 1H), 7.20 (d, J = 6.7 Hz, 1H), 6.73 (d, J = 15.9 Hz, 1H), 5.86-5.68 (m, 1H), 2.89 (s, 3H), 2.70 (s, 3H), 2.11-2.03 (m, 1H), 1.69-1.58 (m, 4H), 1.58-1.46 (m, 2H), 1.44-1.33 (m, 2H), 1.27-1.21 (m, 1H), 1.07 (s, 6H). | 454.1 |
| 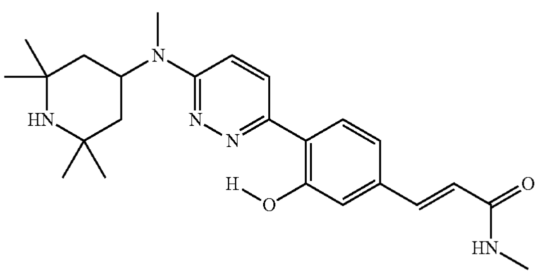 | (E)-3-(3-hydroxy-4-(6-(methyl(2,2,6,6-tetramethylpiperidin-4-yl)amino)pyridazin-3-yl)phenyl)-N-methylacrylamide | $^1$H NMR (500 MHz, DMSO-d$_6$) δ 13.59 (s, 1H), 9.02-8.91 (m, 1H), 8.27 (d, J = 10.1 Hz, 1H), 8.09 (d, J = 4.8 Hz, 1H), 7.94 (d, J = 8.2 Hz, 1H), 7.48 (d, J = 9.9 Hz, 1H), 7.37 (d, J = 15.7 Hz, 1H), 7.16-7.09 (m, 2H), 6.64 (d, J = 15.8 Hz, 1H), 5.20-5.03 (m, 1H), 2.99 (s, 3H), 2.71 (d, J = 4.6 Hz, 3H), 2.01-1.88 (m, 2H), 1.83-1.74 (m, 2H), 1.53 (s, 6H), 1.45 (s, 6H). | 424.3 |
| 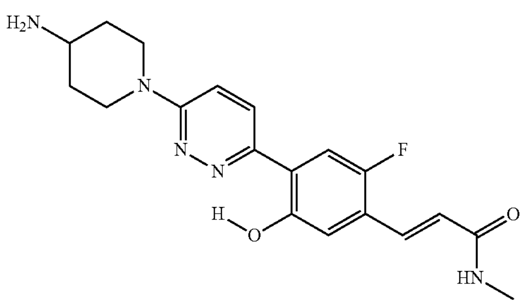 [SMILES: CNC(=O)/C=C/c1cc(O)c(-c2ccc(N3CCC(N)CC3)nn2)cc1F] | (E)-3-(4-(6-(4-aminopiperidin-1-yl)pyridazin-3-yl)-2-fluoro-5-hydroxyphenyl)-N-methylacrylamide | $^1$H NMR (500 MHz, DMSO-d$_6$) δ 8.28 (d, J = 10.0 Hz, 1H), 8.17 (d, J = 4.9 Hz, 1H), 7.88 (d, J = 12.3 Hz, 1H), 7.59 (d, J = 9.9 Hz, 1H), 7.43 (d, J = 15.8 Hz, 1H), 7.15 (d, J = 6.6 Hz, 1H), 6.72 (d, J = 15.9 Hz, 1H), 4.46-4.39 (m, 1H), 3.20-3.15 (m, 2H), 3.14-3.06 (m, 2H), 2.72 (d, J = 4.7 Hz, 3H), 1.94-1.88 (m, 2H), 1.46-1.35 (m, 2H). | 372.1 |
| 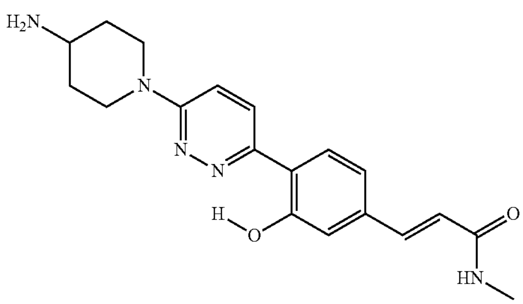 [SMILES: CNC(=O)/C=C/c1ccc(-c2ccc(N3CCC(N)CC3)nn2)c(O)c1] | (E)-3-(4-(6-(4-aminopiperidin-1-yl)pyridazin-3-yl)-3-hydroxyphenyl)-N-methylacrylamide | $^1$H NMR (500 MHz, DMSO-d$_6$) δ 8.22 (d, J = 9.9 Hz, 1H), 8.06 (d, J = 5.6 Hz, 1H), 7.92 (d, J = 8.2 Hz, 1H), 7.56 (d, J = 10.0 Hz, 1H), 7.36 (d, J = 15.6 Hz, 1H), 7.12 (d, J = 9.9 Hz, 2H), 6.63 (d, J = 15.8 Hz, 1H), 4.37-4.24 (m, 2H), 3.14-3.03 (m, 2H), 2.92-2.83 (m, 1H), 2.71 (s, 3H), 1.85-1.75 (m, 2H), 1.29-1.17 (m, 2H). | 354.1 |

TABLE 2

Exemplary SMSM compounds

| Structure | Name | NMR | MS |
|---|---|---|---|
| 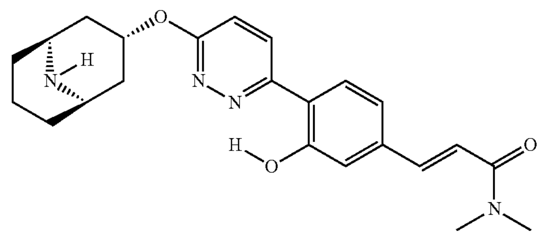 [SMILES: CN(C)C(=O)/C=C/c1ccc(-c2ccc(O[C@@H]3C[C@H]4CCC[C@@H](C3)N4)nn2)c(O)c1] | (E)-3-(4-(6-(41R,3s,5S)-9-azabicyclo[3.3.1]nonan-3-yl)oxy)pyridazin-3-yl)-3-hydroxyphenyl)-N,N-dimethylacrylamide | $^1$H NMR (500 MHz, DMSO-d$_6$) δ 13.04 (br, 1H), 8.45 (d, J = 9.6 Hz, 1H), 7.97 (d, J = 8.3 Hz, 1H), 7.41 (t, J = 12.4 Hz, 2H), 7.37-7.22 (m, 3H), 6.12-6.01 (m, 1H), 3.26-3.21 (m, 2H), 3.17 (s, 3H), 2.94 (s, 3H), 2.30-2.22 (m, 2H), 1.87-1.71 (m, 6H), 1.70-1.59 (m, 2H). | 409.3 |
| 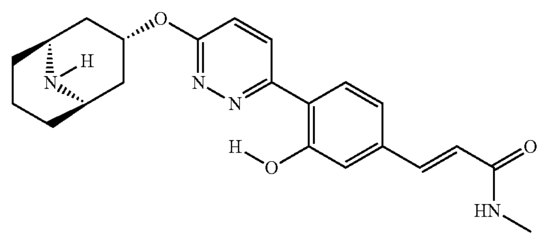 [SMILES: CNC(=O)/C=C/c1ccc(-c2ccc(O[C@@H]3C[C@H]4CCC[C@@H](C3)N4)nn2)c(O)c1] | (E)-3-(4-(6-(((1R,3s,5S)-9-azabicyclo[3.3.1]nonan-3-yl)ypoxy)pyridazin-3-yl)-3-hydroxyphenyl)-N-methylacrylamide | $^1$H NMR (500 MHz, DMSO-d$_6$) δ 12.63 (s, 1H), 8.92 (br, 1H), 8.43 (d, J = 9.5 Hz, 1H), 8.10 (d, J = 4.4 Hz, 1H), 7.97 (d, J = 8.5 Hz, 1H), 7.41 (dd, J = 28.5, 12.6 Hz, 2H), 7.17 (s, 2H), 6.66 (d, J = 15.9 Hz, 1H), 6.11-5.97 (m, 1H), 3.78 (s, 2H), 2.72 (d, J = 4.5 Hz, 3H), 2.48-2.44 (m, 2H), 2.21-2.07 (m, 2H), 2.07-1.94 (m, 2H), 1.94-1.66 (m, 4H). | 395.0 |
| 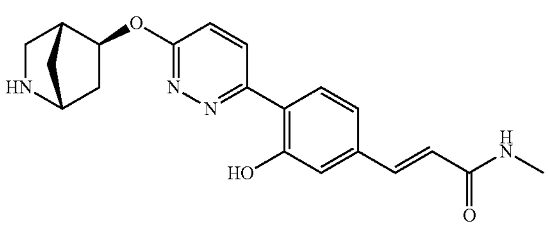 [SMILES: CNC(=O)/C=C/c1ccc(-c2ccc(O[C@H]3C[C@H]4C[C@@H]3CN4)nn2)c(O)c1] | (E)-3-(4-(6-(((1R,4R,5S)-2-azabicyclo[2.2.1]heptan-5-ypoxy)pyridazin-3-yl)-3-hydroxyphenyl)-N-methylacrylamide | 1H NMR (400 MHz, DMSO-d$_6$) δ 8.42 (d, J = 9.6 Hz, 1H), 8.10 (q, J = 4.8 Hz, 1H), 7.98 (d, J = 8.8 Hz, 1H), 7.46-7.34 (m, 2H), 7.19-7.14 (m 2H), 6.65 (d J = 15.8 Hz, 1H), 5.13 (d, J = 6.5 Hz, 1H), 3.43 (br, 1H), 2.80 (dd, J = 10.0, 4.2 Hz, 1H), 2.72 (d, J = 4.8 Hz, 3H), 2.68-2.64 (m, 1H), 2.55-2.51 (m, 1H), 2.13-2.06 (m, 1H), 1.73-1.68 (m, 1H), 1.63-1.56 (m, 1H), 1.43-1.38 (m, 1H). | 367.2 |
| 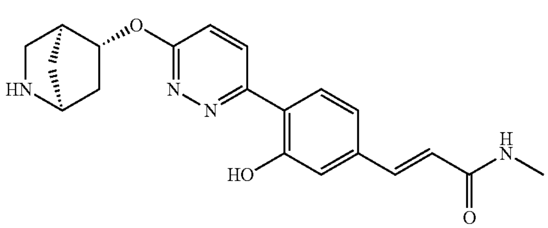 [SMILES: CNC(=O)/C=C/c1ccc(-c2ccc(O[C@@H]3C[C@@H]4C[C@H]3CN4)nn2)c(O)c1] | (E)-3-(4-(6-(((1S,4S,5R)-2-azabicyclo[2.2.1]heptan-5-yl)oxy)pyridazin-3-yl)-3-hydroxyphenyl)-N-methylacrylamide | $^1$H NMR (400 MHz, DMSO-d$_6$) δ 8.42 (d, J = 9.6 Hz, 1H), 8.10 (q, J = 4.8 Hz, 1H), 7.98 (d, J = 8.8 Hz, 1H), 7.46-7.34 (m, 2H), 7.19-7.14 (m, 2H), 6.65 (d, J = 15.8 Hz, 1H), 5.13 (d, J = 6.5 Hz, 1H), 3.43 (br, 1H), 2.80 (dd, J = 10.0, 4.2 Hz, 1H), 2.72 (d, J = 4.8 Hz, 3H), 2.68-2.64 (m, 1H), 2.55-2.51 (m, 1H), 2.13-2.06 (m, 1H), 1.73-1.68 (m, 1H), 1.63-1.56 (m, 1H), 1.43-1.38 (m, 1H). | 367.1 |
| 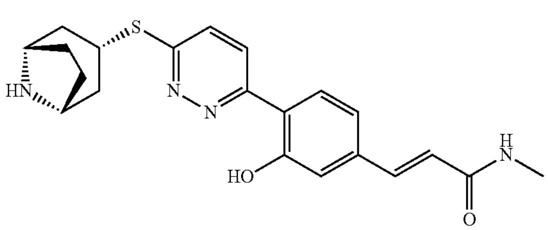 [SMILES: CNC(=O)/C=C/c1ccc(-c2ccc(S[C@@H]3C[C@H]4CC[C@@H](C3)N4)nn2)c(O)c1] | (E)-3-(4-(6-(((1R,3s,5S)-8-azabicyclo[3.2.1]octan-3-yl)thio)pyridazin-3-yl)-3-hydroxyphenyl)-N-methylacrylamide | (d, J = 9.5 Hz, 1H), 8.13 (d, J = 4.9 Hz, 1H) 7.99 (d J = 8.5 Hz, 1H) 7.75 (d, J = 9.3 Hz, 1H), 7.38 (d, J = 15.8 Hz, 1H), 7.17-7.15 (m, 2H), 6.65 (d, J = 15.8 Hz, 1H), 4.30-4.27 (m, 1H), 3.45 (s, 2H), 2.72 (d, J = 4.5 Hz, 3H), 2.01-1.97 (m, 2H), 1.86-1.55 (m, 6H). | 397.2 |

TABLE 3

Exemplary SMSM compounds

| Structure | Name |
|---|---|
| 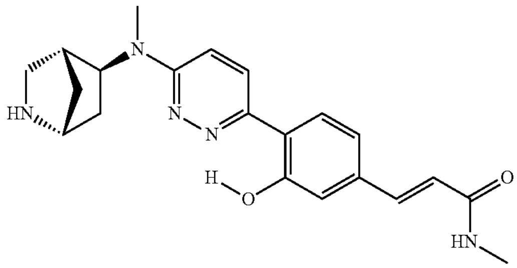 [SMILES: CNC(=O)/C=C/c1ccc(-c2ccc(N(C)[C@H]3C[C@H]4C[C@@H]3CN4)nn2)c(O)c1] | (E)-3-(4-(6-(((1R,4R,5S)-2-azabicyclo[2.2.1]heptan-5-yl)(methyl)amino)pyridazin-3-yl)-3-hydroxyphenyl)-N-methylacrylamide |
| 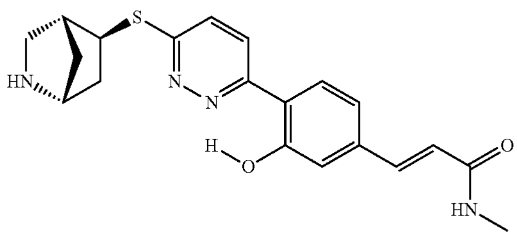 [SMILES: CNC(=O)/C=C/c1ccc(-c2ccc(S[C@H]3C[C@H]4C[C@@H]3CN4)nn2)c(O)c1] | (E)-3-(4-(6-(((1R,4R,5S)-2-azabicyclo[2.2.1]heptan-5-yl)thio)pyridazin-3-yl)-3-hydroxyphenyl)-N-methylacrylamide |
| 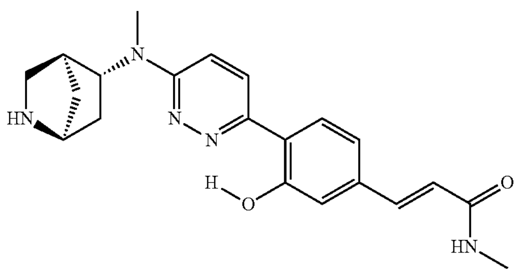 [SMILES: CNC(=O)/C=C/c1ccc(-c2ccc(N(C)[C@@H]3C[C@@H]4C[C@H]3CN4)nn2)c(O)c1] | (E)-3-(4-(6-(((1S,4S,5R)-2-azabicyclo[2.2.1]heptan-5-yl)(methyl)amino)pyridazin-3-yl)-3-hydroxyphenyl)-N-methylacrylamide |
| 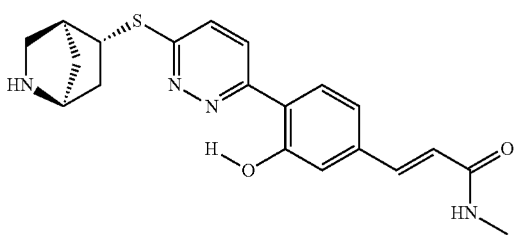 [SMILES: CNC(=O)/C=C/c1ccc(-c2ccc(S[C@@H]3C[C@@H]4C[C@H]3CN4)nn2)c(O)c1] | (E)-3-(4-(6-(((1S,4S,5R)-2-azabicyclo[2.2.1]heptan-5-yl)thio)pyridazin-3-yl)-3-hydroxyphenyl)-N-methylacrylamide |
| 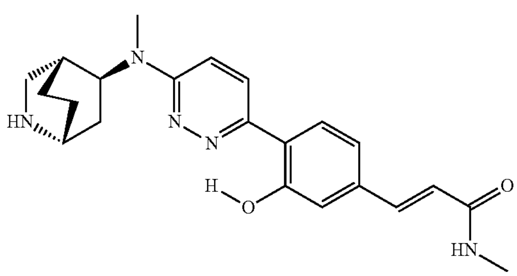 [SMILES: CNC(=O)/C=C/c1ccc(-c2ccc(N(C)[C@H]3C[C@H]4CC[C@@H]3CN4)nn2)c(O)c1] | (E)-3-(4-(6-(((1R,4R,5, S)-2-azabicyclo[2.2.2]octan-5-yl)(methyl)amino)pyridazin-3-yl)-3-hydroxyphenyl)-N-methylacrylamide |
| 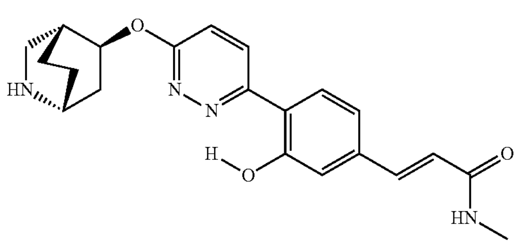 [SMILES: CNC(=O)/C=C/c1ccc(-c2ccc(O[C@H]3C[C@H]4CC[C@@H]3CN4)nn2)c(O)c1] | (E)-3-(4-(6-(((1R,4R,5S)-2-azabicyclo[2.2.2]octan-5-yl)oxy)pyridazin-3-yl)-3-hydroxyphenyl)-N-methylacrylamide |

TABLE 3-continued

Exemplary SMSM compounds

| Structure | Name |
|---|---|
| 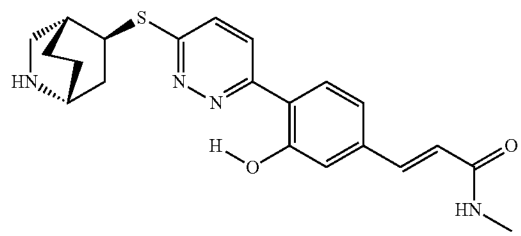 | (E)-3-(4-(6-(((1R,4R,5S)-2-azabicyclo[2.2.2]octan-5-yl)thio)pyridazin-3-yl)-3-hydroxyphenyl)-N-methylacrylamide |
| 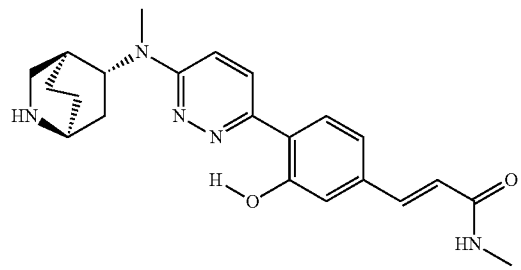 [SMILES: CNC(=O)/C=C/c1ccc(-c2ccc(N(C)[C@@H]3C[C@@H]4CC[C@H]3CN4)nn2)c(O)c1] | (E)-3-(4-(6-(((1S,4S,5R)-2-azabicyclo[2.2.2]octan-5-yl)(methyl)amino)pyridazin-3-yl)-3-hydroxyphenyl)-N-methylacrylamide |
| 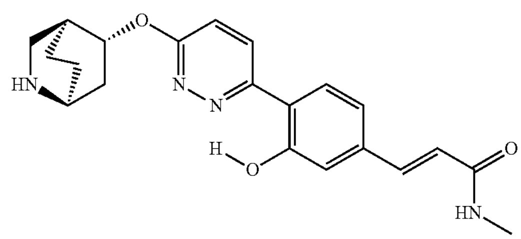 | (E)-3-(4-(6-(((1S,4S,5R)-2-azabicyclo[2.2.2]octan-5-y)oxy)pyridazin-3-yl)-3-hydroxyphenyl)-N-methylacrylamide |
| 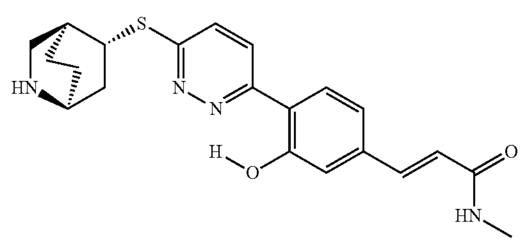 [SMILES: CNC(=O)/C=C/c1ccc(-c2ccc(S[C@@H]3C[C@@H]4CC[C@H]3CN4)nn2)c(O)c1] | (E)-3-(4-(6-(((1S,4S,5R)-2-azabicyclo[2.2.2]octan-5-yl)thio)pyridazin-3-yl)-3-hydroxyphenyl)-N-methylacrylamide |
| 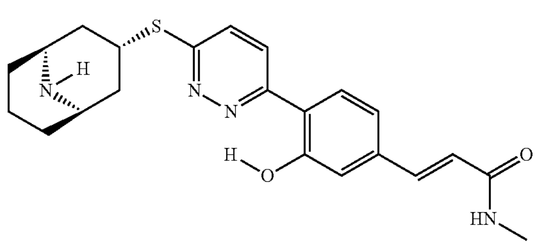 [SMILES: CNC(=O)/C=C/c1ccc(-c2ccc(S[C@@H]3C[C@H]4CCC[C@@H](C3)N4)nn2)c(O)c1] | (E)-3-(4-(6-(((1R,3s,5S)-9-azabicyclo[3.3.1]nonan-3-yl)thio)pyridazin-3-yl)-3-hydro xyphenyl)-N-methylacrylamide |
| 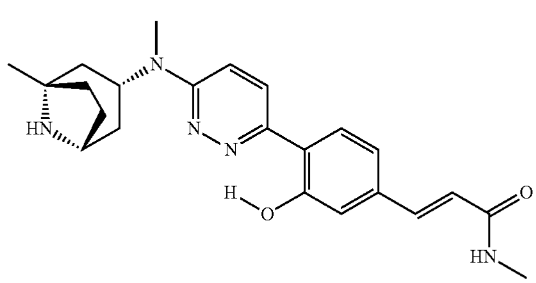 [SMILES: CNC(=O)/C=C/c1ccc(-c2ccc(N(C)[C@@H]3C[C@H]4CC[C@@](C)(C3)N4)nn2)c(O)c1] | (E)-3-(3-hydroxy-4-(6-(methyl((1S,3R,5R)-1-methyl-8-azabicyclo[3.2.1]octan-3-yl)amino)pyridazin-3-yl)phenyl)-N-methylacrylamide |

TABLE 3-continued

Exemplary SMSM compounds

| Structure | Name |
|---|---|
| 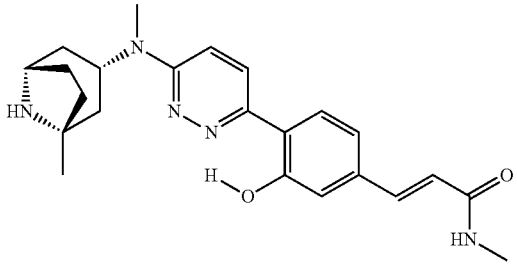 [SMILES: CNC(=O)/C=C/c1ccc(-c2ccc(N(C)[C@H]3C[C@@H]4CC[C@](C)(C3)N4)nn2)c(O)c1] | (E)-3-(3-hydroxy-4-(6-(methyl((1R,3S,5S)-1-methyl-8-azabicyclo[3.2.1]octan-3-yl)amino)pyridazin-3-yl)phenyl)-N-methylacrylamide |
| 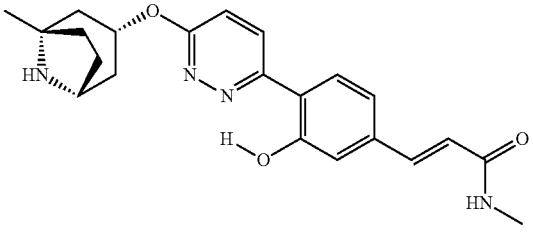 | (E)-3-(3-hydroxy-4-(6-(((1S,3R,5R)-1-methyl-8-azabicyclo[3.2.1]octan-3-yl)oxy)pyridazin-3-yl)phenyl)-N-methylacrylamide |
| 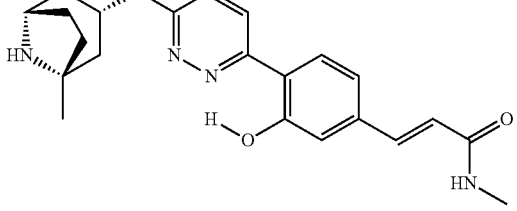 | (E)-3-(3-hydroxy-4-(6-(((1R,3S,5S)-1-methyl-8-azabicyclo[3.2.1]octan-3-yl)oxy)pyridazin-3-yl)phenyl)-N-methylacrylamide |
| 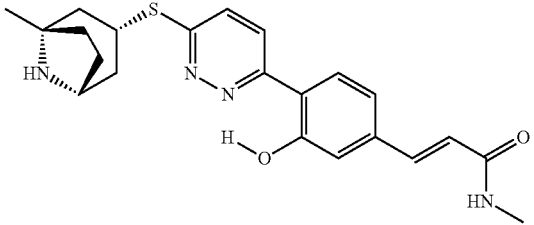 [SMILES: CNC(=O)/C=C/c1ccc(-c2ccc(O[C@@H]3C[C@H]4CC[C@@](C)(C3)N4)nn2)c(O)c1] | (E)-3-(3-hydroxy-4-(6-(((1S,3R,5R)-1-methyl-8-azabicyclo[3.2.1]octan-3-yl)thio)pyridazin-3-yl)phenyl)-N-methylacrylamide |
| 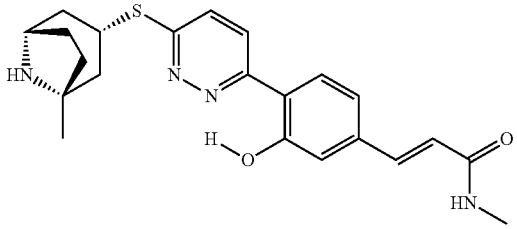 [SMILES: CNC(=O)/C=C/c1ccc(-c2ccc(O[C@H]3C[C@@H]4CC[C@](C)(C3)N4)nn2)c(O)c1] | (E)-3-(3-hydroxy-4-(6-(((1R,3S,5S)-1-methyl-8-azabicyclo[3.2.1]octan-3-yl)thio)pyridazin-3-yl)phenyl)-N-methylacrylamide |

TABLE 4

Exemplary SMSM compounds

| Name | Structure |
|---|---|
| (E)-3-(4-(6-(((1R,3s,5S)-8-azabicyclo[3.2.1]octan-3-yl)(methyl)amino)pyridazin-3-yl)-3-hydroxyphenyl)-N-methylacrylamide | |
| (E)-3-(4-(6-(((1R,3s,5S)-1,5-dimethyl-8-azabicyclo[3.2.1]octan-3-yl)(methyl)amino)pyridazin-3-yl)-3-hydroxyphenyl)-N-methylacrylamide | |
| (E)-3-(4-(6-(((1R,3 s,5 S)-1,5-dimethyl-8-azabicyclo[3.2.1]octan-3-yl)(methypamino)pyridazin-3-yl)-2-fluoro-5-hydroxyphenyl)-N-methylacrylamide | |
| (E)-3-(4-(6-(((1R,3s,5S)-1,5-dimethyl-8-azabicyclo[3.2.1]octan-3-yl)(methyl)amino)pyridazin-3-yl)-3-hydroxyphenyl)-N,N-dimethylacrylamide | |
| (E)-3-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-N,N-dimethylacrylamide | |

TABLE 4-continued

Exemplary SMSM compounds

| Name | Structure |
|---|---|
| 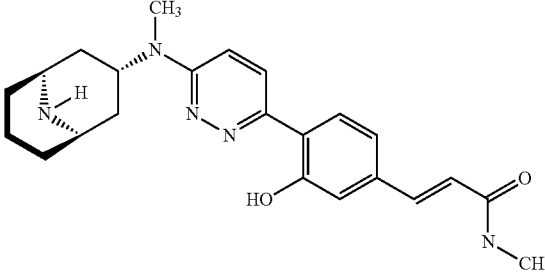 | (E)-3-(4-(6-(((1R,3s,5 S)-9-azabicyclo[3.3.1]nonan-3-yl)(methyl)amino)pyridazin-3-yl)-3-hydroxyphenyl)-N-methylacrylamide |
| 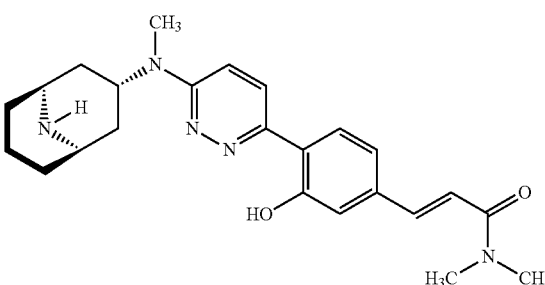 | (E)-3-(4-(6-(((1R,3s,5 S)-9-azabicyclo[3.3.1]nonan-3-yl)(methyl)amino)pyridazin-3-yl)-3-hydroxyphenyl)-N,N-dimethylacrylamide |
| 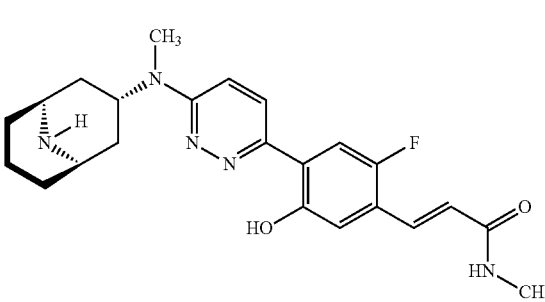 | (E)-3-(4-(6-(((1R,3s,5S)-9-azabicyclo[3.3.1]nonan-3-yl)(methyl)amino)pyridazin-3-yl)-2-fluoro-5-hydroxyphenyl)-N-methylacrylamide |
| 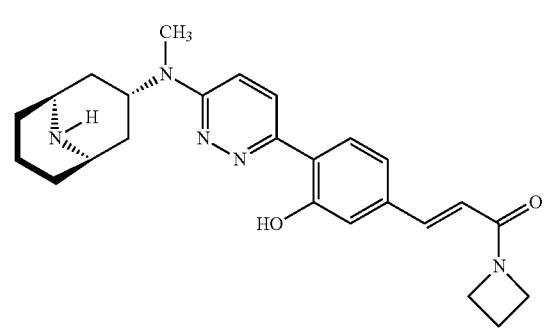 | (E)-3-(4-(6-(((1R,3s,5S)-9-azabicyclo-[3.3.1]-nonan-3-yl)(methyl)amino)pyridazin-3-yl)-3-hydroxyphenyl)-1-(azetidin-1-yl)prop-2-en-1-one |
| 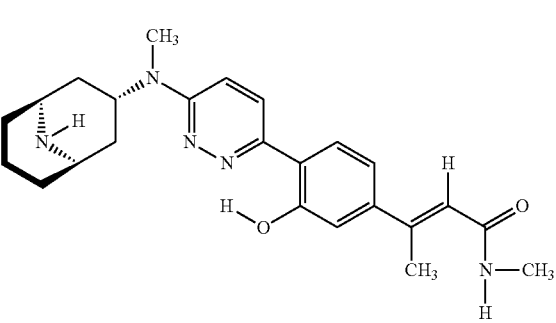 | (E)-3-(4-(6-(((1R,3s,5S)-9-azabicyclo[3.3.1]nonan-3-yl)(methyl)amino)pyridazin-3-yl)-3-hydroxyphenyl)-N-methylbut-2-enamide |

TABLE 4-continued

Exemplary SMSM compounds

| Name | Structure |
|---|---|
| (E)-3-(4-(6-(((1R,3s,5S)-9-azabicyclo[3.3.1]nonan-3-yl)(methyl)amino)pyridazin-3-yl)-3-hydroxyphenyl)-N,N-dimethylbut-2-enamide | 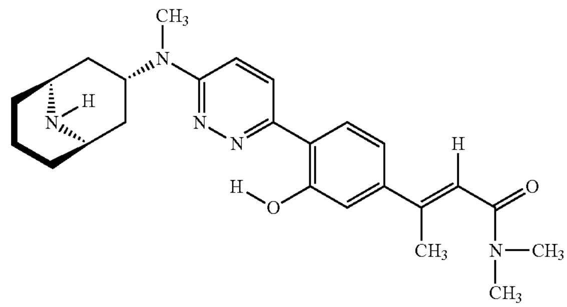 |
| (E)-3-(4-(6-(((1R,3 s,5S)-9-azabicyclo[3.3.1]nonan-3-yl)(methyl)amino)pyridazin-3-yl)-3-hydroxyphenyl)-1-morpholinoprop-2-en-1-one | 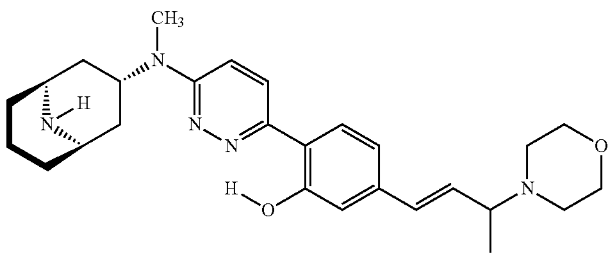 |
| (E)-3-(4-(6-(((1R,3s,5S)-9-azabicyclo[3.3.1]nonan-3-yl)(methyl)amino)pyridazin-3-yl)-3-hydroxyphenyl)-N-methoxy-N-methylacrylamide | 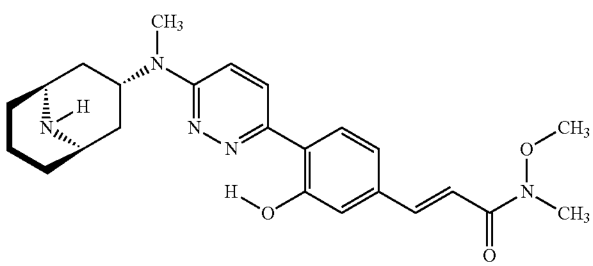 |
| (E)-3-(4-(6-(((1R,3s,5S)-9-azabicyclo[3.3.1]nonan-3-yl)(methyl)amino)pyridazin-3-yl)-3-hydroxyphenyl)-N-cyclopropylacrylamide | 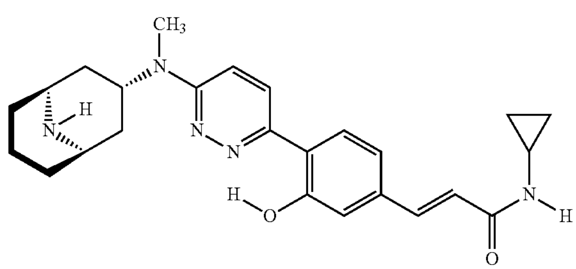 |
| (E)-3-(4-(6-(((1R,3s,5S)-9-azabicyclo[3.3.1]nonan-3-yl)(methyl)amino)pyridazin-3-yl)-3-hydroxyphenyl)-N-cyclopropyl-N-methylacrylamide | 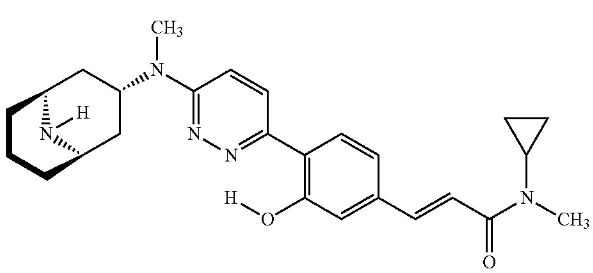 |

TABLE 4-continued

Exemplary SMSM compounds

| Name | Structure |
|---|---|
| | (E)-N-cyclopropyl-3-(4-(6-(((1R,3s,5S)-1,5-dimethyl-9-azabicyclo yl)(methyl)amino)pyridazin-3-yl)-3-hydroxyphenyl)acrylamide |
| | (E)-N-cyclopropyl-3-(4-(6-(((1R,3s,5S)-1,5-dimethyl-9-azabicyclo[3.3.1]nonan-3-yl)(methyl)amino)pyridazin-3-yl)-3-hydroxyphenyl)-N-methylacrylamide |
| | (E)-3-(4-(6-(((1R,3s,5S)-1,5-dimethyl-9-azabicyclo[3.3.1]nonan-3-yl)(methyl)amino)pyridazin-3-yl)-3-hydroxyphenyl)-N-methylacrylamide |
| | (E)-3-(4-(6-(((1R,5S,7r)-3-oxa-9-azabicyclo[3.3.1]nonan-7-yl)(methyl)amino)pyridazin-3-yl)-3-hydroxyphenyl)-N-methylacrylamide |
| | (E)-3-(4-(6-(((1R,5S,7r)-1,5-dimethyl-3-yl)(methyl)amino)pyridazin-3-yl)-3-hydroxyphenyl)-N-methylacrylamide |

TABLE 4-continued

Exemplary SMSM compounds

| Name | Structure |
|---|---|
| (E)-3-(4-(6-(((1R,5 S,7r)-3-oxa-9-azabicyclo[3.3.1]nonan-7-yl)(methyl)amino)pyridazin-3-yl)-3-hydroxyphenyl)-N-methylacrylamide | |
| (E)-3-(4-(6-(((1R,5S,7r)-1,5-dimethyl-3-oxa-9-azabicyclo[3.3.1]nonan-7-yl)(methyl)amino)pyridazin-3-yl)-3-hydroxyphenyl)-N-methylacrylamide | |
| 2-(6-(((1R,3s,5S)-9-azabicyclo[3.3.1]nonan-3-yl)(methypamino)pyridazin-3-yl)-5-((E)-2-(methylsulfonyl)vinyl)phenol | |
| (E)-2-(4-(64((1R,3s,5S)-9-azabicyclo[3.3.1]nonan-3-yl)(methypamino)pyridazin-3-yl)-3-hydroxyphenyl)ethene-1-sulfonamide | |
| ((E)-4-(6-(((1R,3s,5S)-9-azabicyclo[3.3.1]nonan-3-yl)(methyl)amino)pyridazin-3-yl)-3-hydroxystyryl)(imino)(methyl)-16-sulfanone | |

TABLE 4-continued

Exemplary SMSM compounds

| Name | Structure |
|---|---|
| ((E)-4-(6-(((1R,3s,5S)-9-azabicyclo[3.3.1]nonan-3-yl)(methyl)amino)pyridazin-3-yl)-3-hydroxystyryl)(methyl)(methylimino)-16-sulfanone | |

TABLE 5

Exemplary SMSM compounds

| Structure | Name |
|---|---|
| 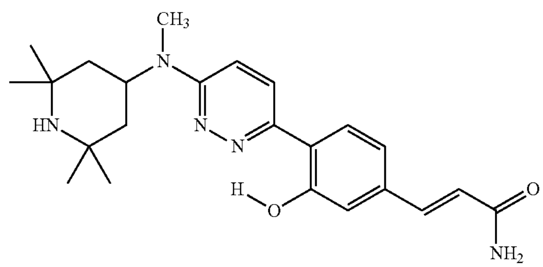 [SMILES: CN(c1ccc(-c2ccc(/C=C/C(N)=O)cc2O)nn1)C1CC(C)(C)NC(C)(C)C1] | (E)-3-(3-hydroxy-4-(6-(methyl(2,2,6,6-tetramethylpiperidin-4-yl)amino)pyridazin-3-yl)phenypacrylamide |
| 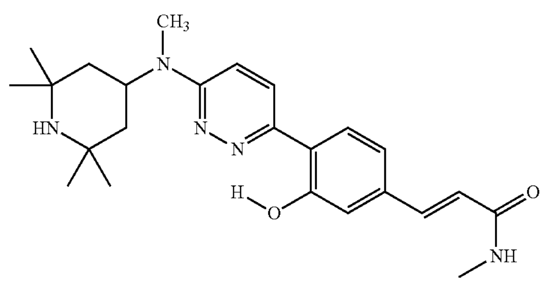 [SMILES: CNC(=O)/C=C/c1ccc(-c2ccc(N(C)C3CC(C)(C)NC(C)(C)C3)nn2)c(O)c1] | (E)-3-(3-hydroxy-4-(6-(methyl(2,2,6,6-tetramethylpiperidin-4-yl)amino)pyridazin-3-yl)phenyl)-N-methylacrylamide |
| 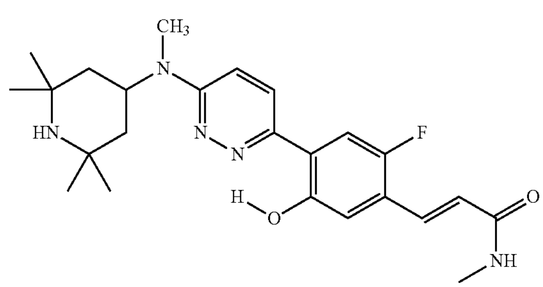 [SMILES: CNC(=O)/C=C/c1cc(O)c(-c2ccc(N(C)C3CC(C)(C)NC(C)(C)C3)nn2)cc1F] | (E)-3-(2-fluoro-5-hydroxy-4-(6-(methyl(2,2,6,6-tetramethylpiperidin-4-yl)amino)pyridazin-3-yl)phenyl)-N-methylacrylamide |

TABLE 5-continued

Exemplary SMSM compounds

| Structure | Name |
|---|---|
| 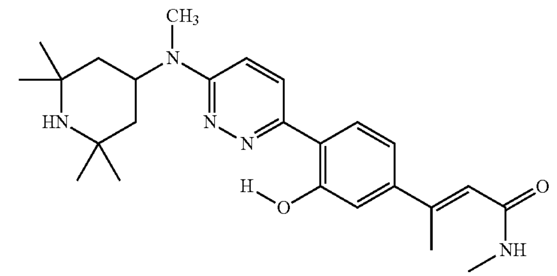 [SMILES: CNC(=O)/C=C(\C)c1ccc(-c2ccc(N(C)C3CC(C)(C)NC(C)(C)C3)nn2)c(O)c1] | (E)-3-(3-hydroxy-4-(6-(methyl(2,2,6,6-tetramethylpiperidin-4-yl)amino)pyridazin-3-yl)phenyl)-N-methylbut-2-enamide |
| 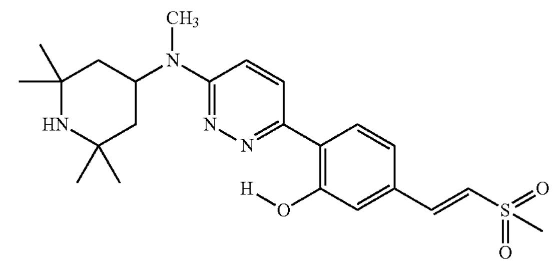 | (E)-2-(6-(methyl(2,2,6,6-tetramethylpiperidin-4-yl)amino)pyridazin-3-yl)-5-(2-(methylsulfonyl)vinyl)phenol |
| 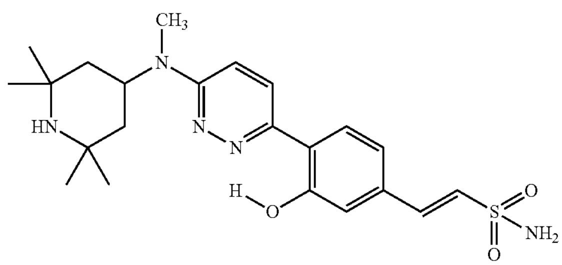 [SMILES: CN(c1ccc(-c2ccc(/C=C/S(N)(=O)=O)cc2O)nn1)C1CC(C)(C)NC(C)(C)C1] | (E)-2-(3-hydroxy-4-(6-(methyl(2,2,6,6-tetramethylpiperidin-4-yl)amino)pyridazin-3-yl)phenyl)ethene-1-sulfonamide |
| 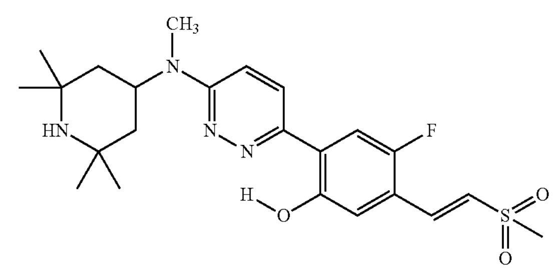 | (E)-4-fluoro-2-(6-(methyl(2,2,6,6-tetramethylpiperidin-4-yl)amino)pyridazin-3-yl)-5-(2-(methylsulfonyl)vinyl)phenol |
| 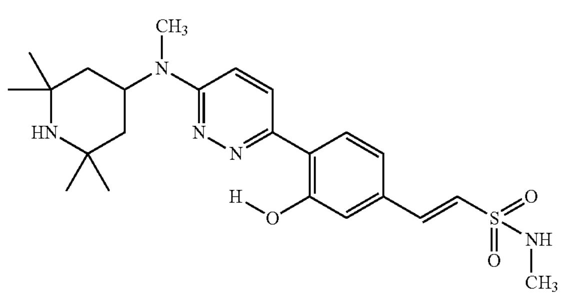 | (E)-2-(3-hydroxy-4-(6-(methyl(2,2,6,6-tetramethylpiperidin-4-yl)amino)pyridazin-3-yl)phenyl)-N-methylethene-1-sulfonamide |

TABLE 5-continued

Exemplary SMSM compounds

| Structure | Name |
|---|---|
| 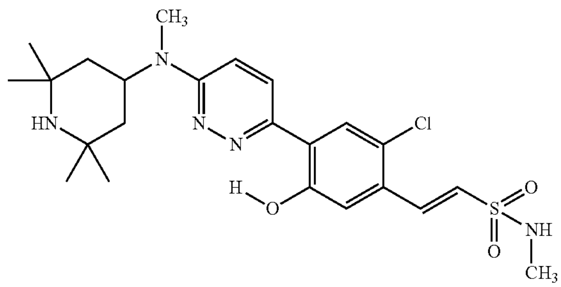 | (E)-2-(2-chloro-5-hydroxy-4-(6-(methyl(2,2,6,6-tetramethylpiperidin-4-yl)amino)pyridazin-3-yl)phenyl)-N-methylethene-1-sulfonamide |
| 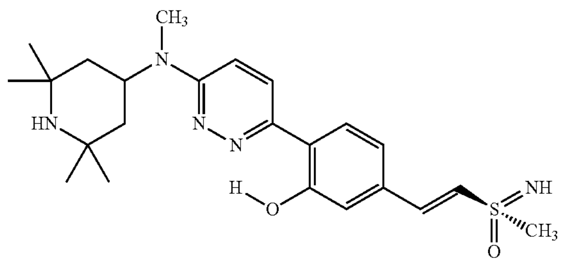 | (S,E)-(3-hydroxy-4-(6-(methyl(2,2,6,6-tetramethylpiperidin-4-yl)amino)pyridazin-3-yl)styryl)(imino)(methyl)-16-sulfanone |
| 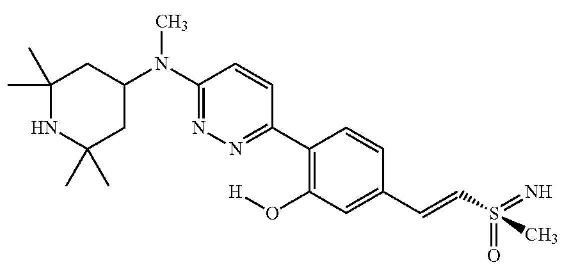 | (R,E)-(3-hydroxy-4-(6-(methyl(2,2,6,6-tetramethylpiperidin-4-yl)amino)pyridazin-3-yl)styryl)(imino)(methyl)-16-sulfanone |
| 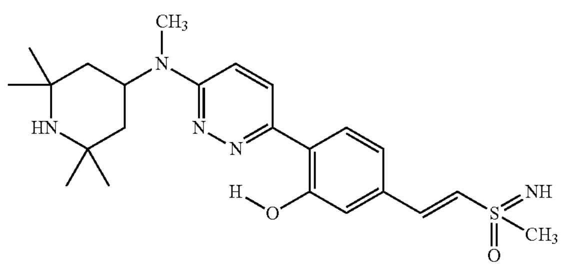 | (E)-(3-hydroxy-4-(6-(methyl(2,2,6,6-tetramethylpiperidin-4-yl)amino)pyridazin-3-yl)styryl)(imino)(methyl)-16-sulfanone |

Further Forms of Compounds

In one aspect, the splice modifying compound described herein possesses one or more stereocenters and each stereocenter exists independently in either the R or S configuration. The compounds presented herein include suitable diastereomeric, enantiomeric, and epimeric forms as well as the appropriate mixtures thereof. The compounds and methods provided herein include suitable cis, trans, syn, anti, exo, endo, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a splice modifying compound described herein with acids. Pharmaceutically acceptable salts are also obtained by reacting a splice modifying compound described herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, such as water, ethanol, and the like. Hydrates are formed when the solvent is water, or alcoholates are formed when the solvent is alcohol. In some embodiments, solvates of compounds described herein are conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3 527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds are synthesized as described in the Examples section.

Definitions

In the current description, certain specific details are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The terms "compound(s) of this disclosure", "compound(s) of the present disclosure", "FOXM1 gene splicing modifier", "FOXM1 splicing modifier", "splice modifying compounds", and "compounds modifying splicing of the FOXM1 gene" are interchangeably used herein and refer to compounds as disclosed herein and stereoisomers, tautomers, solvates, and salts (e.g., pharmaceutically acceptable salts) thereof.

The term "pharmaceutically acceptable salts" denotes salts which are not biologically or otherwise undesirable. Pharmaceutically acceptable salts include both acid and base addition salts.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

The term "amino" refers to the —$NH_2$ substituent.
The term "hydroxy" refers to the —OH substituent.
The term "methoxy" refers to the —$OCH_3$ substituent.
The term "oxo" refers to the =O substituent.
The term "thioxo" refers to the =S substituent.
The term "halo", "halogen", and "halide" are used interchangeably herein and denote fluoro, chloro, bromo, or iodo. In some embodiments, the halogen is fluoro or chloro.

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —$CH(CH_3)_2$ or —C(CH$_3$)$_3$. Unless stated otherwise specifically in the specification, an alkyl group may be optionally substituted as described below.

The term "alkylene" or "alkylene chain" refers to a straight or branched divalent hydrocarbon chain linking the rest of the molecule to a radical group. In some embodiments, the alkylene is —CH$_2$—, —CH$_2$CH$_2$—, —CH$_2$CH$_2$CH$_2$—, or —CH$_2$CH(CH$_3$)CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

The term "alkoxy" refers to a radical of the formula —OR$^x$ where R$^x$ is an alkyl radical as defined above. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

The term "alkylamino" refers to a radical of the formula —NHR$^x$ or —NR$^x$R$^x$ where each R$^x$ is, independently, an alkyl radical as defined above. Unless stated otherwise specifically in the specification, an alkylamino group may be optionally substituted as described below.

The term "alkenyl" refers to a type of alkyl group in which at least one carbon-carbon double bond is present. In one embodiment, an alkenyl group has the formula —C(R$^x$)=CR$^x_2$, wherein R$^x$ refers to the remaining portions of the alkenyl group, which may be the same or different. In some embodiments, R$^x$ is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkenylene" or "alkenylene chain" refers to a straight or branched divalent hydrocarbon chain in which at least one carbon-carbon double bond is present linking the rest of the molecule to a radical group. In some embodiments, the alkenylene is —CH=CH—, —CH$_2$CH=CH—, or —CH=CHCH$_2$—. In some embodiments, the alkenylene is —CH=CH—. In some embodiments, the alkenylene is —CH$_2$CH=CH—. In some embodiments, the alkenylene is —CH=CHCH$_2$—.

The term "alkynyl" refers to a type of alkyl group in which at least one carbon-carbon triple bond is present. In one embodiment, an alkenyl group has the formula —C≡C—R$^x$, wherein R$^x$ refers to the remaining portions of the alkynyl group. In some embodiments, R$^x$ is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$, —C≡CCH$_2$CH$_3$, and —CH$_2$C≡CH.

The term "aromatic" refers to a planar ring having a delocalized π-electron system containing 4n+2π electrons, where n is an integer. Aromatics can be optionally substituted. The term "aromatic" includes both aryl groups (e.g., phenyl, naphthalenyl) and heteroaryl groups (e.g., pyridinyl, quinolinyl).

The term "aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted. In some embodiments, an aryl group is partially reduced to form a cycloalkyl group defined herein. In some embodiments, an aryl group is fully reduced to form a cycloalkyl group defined herein.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbocyclic" or "carbocycle" refer to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopentyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted.

The term "bridged" refers to any ring structure with two or more rings that contains a bridge connecting two bridgehead atoms. The bridgehead atoms are defined as atoms that are the part of the skeletal framework of the molecule and which are bonded to three or more other skeletal atoms. In some embodiments, the bridgehead atoms are C, N, or P. In some embodiments, the bridge is a single atom or a chain of atoms that connects two bridgehead atoms. In some embodiments, the bridge is a valence bond that connects two bridgehead atoms. In some embodiments, the bridged ring system is cycloalkyl. In some embodiments, the bridged ring system is heterocycloalkyl.

The term "fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with one or more N, S, and O atoms. The non-limiting examples of fused heterocyclyl or heteroaryl ring structures include 6-5 fused heterocycle, 6-6 fused heterocycle, 5-6 fused heterocycle, 5-5 fused heterocycle, 7-5 fused heterocycle, and 5-7 fused heterocycle.

The term "fluoroalkyl" refers to an alkyl in which one or more hydrogen atoms are replaced by a fluorine atom. In one aspect, a fluoralkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, or —N(aryl)-), sulfur (e.g. —S—, —S(=O)—, or —S(=O)$_2$—), or combinations thereof. In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_6$heteroalkyl. Representative heteroalkyl groups include, but are not limited to —OCH$_2$OMe, —OCH$_2$CH$_2$OH, —OCH$_2$CH$_2$OMe, or —OCH$_2$CH$_2$OCH$_2$CH$_2$NH$_2$.

The term "heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —CH$_2$—O—CH$_2$—, —CH$_2$—N(alkyl)-CH$_2$—, —CH$_2$—N(aryl)-CH$_2$—, —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heterocycle" or "heterocyclic" refers to heteroaromatic rings (also known as heteroaryls) and heterocycloalkyl rings (also known as heteroalicyclic groups) that includes at least one heteroatom selected from nitrogen, oxygen and sulfur, wherein each heterocyclic group has from 3 to 12 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 12 atoms in its ring system and aromatic heterocyclic groups include rings having 5 to 12 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The term "heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl. In some embodiments, a heteroaryl group is partially reduced to form a heterocycloalkyl group defined herein. In some embodiments, a heteroaryl group is fully reduced to form a heterocycloalkyl group defined herein.

The term "alkyl-aryl" refers to a radical of the formula —$R^y$—$R^x$, wherein $R^x$ is an alkyl radical as described herein and $R^y$ is an aryl radical as described herein.

The term "alkyl-heterocycloalkyl" refers to a radical of the formula —$R^y$—$R^x$, wherein $R^x$ is an alkyl radical as described herein and $R^y$ is a heterocycloalkyl radical as described herein.

The term "alkyl-heteroaryl" refers to a radical of the formula —$R^y$—$R^x$, wherein $R^x$ is an alkyl radical as described herein and $R^y$ is a heteroaryl radical as described herein.

The term "alkoxy-aryl" refers to a radical of the formula —$R^y$—$R^x$, wherein $R^x$ is an alkoxy radical as described herein and $R^y$ is an aryl radical as described herein.

The term "alkoxy-heterocycloalkyl" refers to a radical of the formula —$R^y$—$R^x$, wherein $R^x$ is an alkoxy radical as described herein and $R^y$ is a heterocycloalkyl radical as described herein.

The term "alkoxy-heteroaryl" refers to a radical of the formula —$R^y$—$R^x$, wherein $R^x$ is an alkoxy radical as described herein and $R^y$ is an heteroaryl radical as described herein.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —NH(cyclopropyl), —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

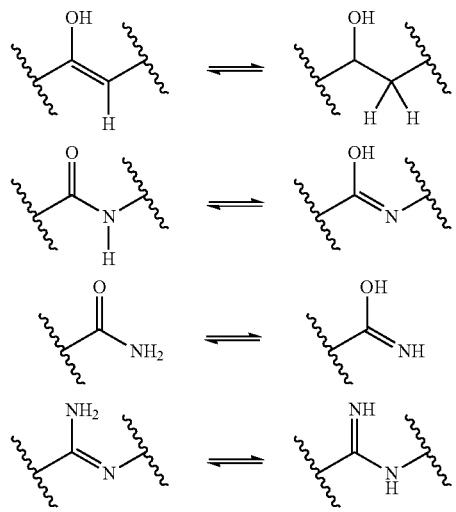

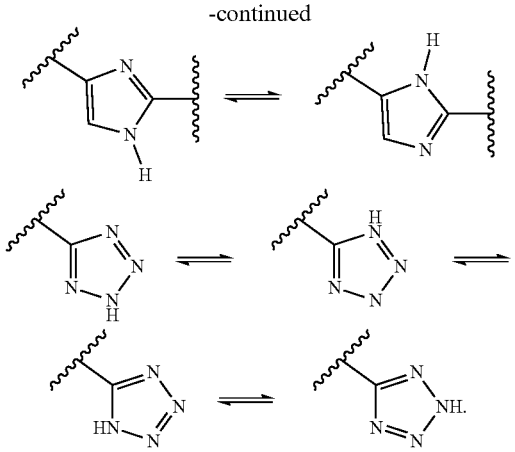

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), Formula (II), or Formula (III) and a co-agent, are both administered to a patient simultaneously in the form of a single entity or dosage. The term "non-fixed combination" means that the active ingredients, e.g. a compound of Formula (I), Formula (II), or Formula (III) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating," or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with one or more pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being nontoxic to the subject administered, such as disintegrators, binders, fillers, solvents, buffers, tonicity agents, stabilizers, antioxidants, surfactants, carriers, diluents or lubricants used in formulating pharmaceutical products.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "animal" as used herein comprises human beings and non-human animals. In one embodiment, a "non-human animal" is a mammal, for example a rodent such as rat or a mouse. In one embodiment, a non-human animal is a mouse.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "FOXM1 polypeptide" is used herein to refer to native FOXM1 polypeptide from any animal, e.g. mammalian, species, including humans, and FOXM1 variants.

The term "compound modifying splicing of the FOXM1 gene" is used herein to refer to compounds which lead to the production of transcriptionally inactive forms of the FOXM1 polypeptide, in particular to the production of FOXM1 A variant, by modifying the FOXM1 splicing such that transcriptionally inactive forms are generated, in particular FOXM1A, and by suppressing the production of transcriptionally active FOXM1 variants, in particular FOXM1B and FOXM1C.

Methods for detection and/or measurement of polypeptides in biological material are well known in the art and include, but are not limited to, Western-blotting, Flow cytometry, ELISAs or RIAs, or various proteomics techniques. An example for a method to measure a polypeptide is an ELISA. This type of protein quantitation is based on an antibody capable of capturing a specific antigen, and a second antibody capable of detecting the captured antigen. The assays mentioned hereinbefore are described in Harlow, E. and Lane, D. Antibodies: A Laboratory Manual, (1988), Cold Spring Harbor Laboratory Press.

Methods for detection and/or measurement of RNA in biological material are well known in the art and include, but are not limited to, Northern-blotting, RNA protection assay, RT PCR. Suitable methods are described in Molecular Cloning: A Laboratory Manual(Fourth Edition) By Michael R. Green, Joseph Sambrook, Peter MacCallum 2012, 2,028 pp, ISBN 978-1-936113-42-2.

Pharmaceutical Compositions and Routes of Administration

In certain embodiments, also described herein are pharmaceutical compositions or medicaments containing the compounds of the present disclosure and a therapeutically inert carrier, diluent or excipient, as well as methods of using the compounds of the present disclosure to prepare such compositions and medicaments. In one example, compounds of Formula (I), Formula (II), or Formula (III) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a splice modifying compound described herein is formulated in an acetate buffer, at pH 5. In another embodiment, the splice modifying compounds described herein are sterile. The compound may be stored, for example, as a solid or amorphous composition, as a lyophilized composition or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to modify FOXM1 gene splicing. For example, such amount may be below the amount that is toxic to normal cells, or the mammal as a whole.

The compounds of the current disclosure may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In some embodiments, the compounds of the present disclosure are formulated for administration to a mammal by intravenous administration, subcutaneous administration, oral administration, inhalation, nasal administration, dermal administration, or ophthalmic administration The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. In some embodiments, the compounds of the present disclosure are administered in a form of a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

A typical composition is prepared by mixing a compound of the present disclosure and a carrier or excipient. Suitable carriers and excipients are well known to those skilled in the art and are described in detail in, e.g., Ansel, Howard C, et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The compositions may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aiding the manufacturing of the pharmaceutical product (i.e., medicament).

An example of a suitable oral dosage form is a tablet containing about 25 mg, 50 mg, 100 mg, 250 mg, or 500 mg of the compound of the present disclosure compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol composition can be prepared by dissolving the compound, for example 5-400 mg, of the present disclosure in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In a particular embodiment, the present disclosure relates to a pharmaceutical composition comprising a FOXM1 gene splicing modifier as described herein or pharmaceutically acceptable salt thereof.

In a particular embodiment, the present disclosure relates to a pharmaceutical composition comprising a FOXM1 gene splicing modifier as described herein or pharmaceutically acceptable salt thereof together with one or more pharmaceutically acceptable excipients.

In a particular embodiment, the present disclosure relates to a pharmaceutical composition comprising a therapeutically effective amount of a FOXM1 gene splicing modifier as described herein or pharmaceutically acceptable salt thereof together with one or more pharmaceutically acceptable excipients.

In a particular embodiment, the present disclosure relates to a combination comprising a therapeutically effective amount of a FOXM1 gene splicing modifier as described herein or pharmaceutically acceptable salt thereof and one or more other therapeutically active pharmaceutical ingredients.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition can be a mixture of an SMSM described herein with one or more other chemical components (i.e. pharmaceutically acceptable ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to an organism.

The compositions described herein can be administered to the subject in a variety of ways, including parenterally, intravenously, intradermally, intramuscularly, colonically, rectally or intraperitoneally. In some embodiments, the small molecule splicing modulator or a pharmaceutically acceptable salt thereof is administered by intraperitoneal injection, intramuscular injection, subcutaneous injection, or intravenous injection of the subject. In some embodiments, the pharmaceutical compositions can be administered parenterally, intravenously, intramuscularly or orally. The oral agents comprising a small molecule splicing modulator can be in any suitable form for oral administration, such as liquid, tablets, capsules, or the like. The oral formulations can be further coated or treated to prevent or reduce dissolution in stomach. The compositions of the present invention can be administered to a subject using any suitable methods known in the art. Suitable formulations for use in the present invention and methods of delivery are generally well known in the art. For example, the small molecule splicing modulators described herein can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

Pharmaceutical formulations described herein can be administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical formulation is in the form of a tablet. In other embodiments, pharmaceutical formulations containing an SMSM described herein are in the form of a capsule. In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, an SMSM described herein can be formulated for use as an aerosol, a mist or a powder. For buccal or sublingual administration, the compositions may take the form of tablets, lozenges, or gels formulated in a conventional manner. In some embodiments, an SMSM described herein can be prepared as transdermal dosage forms. In some embodiments, an SMSM described herein can be formulated into a pharmaceutical composition suitable for intramuscular, subcutaneous, or intravenous injection. In some embodiments, an SMSM described herein can be administered topically and can be formulated into a variety of topically administrable compositions, such as solutions, suspensions, lotions, gels, pastes, medicated sticks, balms, creams or ointments. In some embodiments, an SMSM described herein can be formulated in rectal compositions such as enemas, rectal gels, rectal foams, rectal aerosols, suppositories, jelly suppositories, or retention enemas.

Splicing

Extensive posttranscriptional processing occurs before eukaryotic pre-mRNA matures and exits from the nucleus to the cytoplasm, including the addition of a 7-methylguanosine cap at the 5' end, the cleavage and addition of a poly-A tail at the 3' end as well as the removal of intervening sequences or introns by the spliceosome. The vast majority of higher eukaryotic genes contain multiple introns that are spliced out with high precision and fidelity in order to maintain the reading frame of the exons. Splicing of pre-mRNA can utilize the recognition of short consensus sequences at the boundaries and within introns and exons by an array of small nuclear ribonucleoprotein (snRNP) complexes (e.g., snRNPs U1, U2, U4, U5, U6, U11, U12m U4atc and U6 atc) and a large number of proteins, including spliceosomal proteins and positively as well as negatively acting splicing modulators.

Serine-arginine-rich (SR)-domain-containing proteins generally serve to promote constitutive splicing. They can also modulate alternative splicing by binding to intronic or exonic splicing enhancer (ISE) or ESE, respectively) sequences. Other pre-mRNA binding proteins, such as hnRNPs, regulate splicing by binding to intronic or exonic splicing suppressor (ISS or ESS, respectively) sequences and can also act as general splicing modulators. The SR protein family is a class of at least 10 proteins that have a characteristic serine/arginine rich domain in addition to an RNA-binding. SR proteins are generally thought to enhance splicing by simultaneously binding to U170K, a core component of the U1 snRNP, at the 5' splice site, and the U2AF35 at the 3' splice site, thus bridging the two ends of the intron. While this particular function of SR proteins seems to be redundant, as any individual SR protein can commit a pre-mRNA for constitutive splicing, the role of the various SR proteins in alternative splicing of specific pre-mRNAs is distinct due in part to their ability to recognize and bind to unique consensus sequences. Phosphorylation of the RS domain of SR proteins can lead to the regulation of their protein interactions, RNA binding, localization, trafficking, and role in alternative splicing. Several cellular kinases that phosphorylate SR proteins have been identified, including SR protein Kinase (SRPKs), Cdc2-like kinases (Clks), pre-mRNA processing mutant 4 (PRP4), and topoisomerase I. Optimal phosphorylation of SR proteins may be required for proper functioning as both hypo- and hyper-phosphorylation of the RS domains may be detrimental to their role in constitutive and alternative splicing.

In higher eukaryotes, the vast majority of genes contain one or more introns, which creates a situation in which the exons are spliced together to generate mature mRNA and microRNA (miRNA). In the host nucleus, pre-mRNA splicing is the mechanism by which introns are removed from a pre-mRNA and the exons are ligated together to generate mature mRNAs and pre-miRNA that is then exported to the cytoplasm for translation into the polypeptide gene product. Splicing of pre-mRNA can occur in cis, where two exons derive from two adjacent cotranscribed sequences, or in trans, when the two exons come from different pre-mRNA transcripts. The ratio of the different protein products (isoforms) may be due to the frequency of alternative splicing events within a pre-mRNA that leads to different amounts of distinct splice variants. In some embodiments, alternative splicing of a pre-mRNA may lead to 2, 3, 4, 5, 6, 7, 8, 9, 10, 11, 12, 13, 14, 15, 16, 17, 18, 19 or 20 protein isoforms being expressed.

Aberrations in splicing are thought to be the cause of roughly half of all inherited diseases. Aberrant splicing due to mutations in consensus sequences involved in exon-intron boundary recognition is responsible for up to 15% of inherited diseases. In addition, defects in the splicing machinery itself due to the loss or gain of function of splicing factors and modulators are causes of a wide range of human ailments from cancer to neurodegenerative diseases. Both constitutive and alternative splicing are subject to regulation by upstream signaling pathways. This regulation can be essential during development, in tissue specific expression of certain isoforms, during the cell cycle and in response to extrinsic signaling molecules.

Alternative splicing allows for a single gene to express different isoforms of mRNA, thus playing a major role in contributing to the cellular complexity in higher eukaryotes without the need to expand the genome. Splicing can also be subject to regulation by upstream signaling pathways. For example, an upstream signaling pathway may modulate alternative splicing and increase or decrease expression levels of different isoforms of mRNA.

Alternative splicing events are highly regulated by numerous splicing factors in a tissue type-, developmental stage-, and signal-dependent manner. Furthermore, non-mutation based causes of splicing defects and defects in the splicing machinery itself, e.g., due to the loss/gain of function of splicing factors or their relative stoichiometry, cause of a wide range of human ailments, ranging from cancer to neurodegenerative diseases. In many diseases the disease state is caused by an alteration of the ratio of different isoforms of two or more proteins expressed from a gene. In some embodiments, the alteration in the ratio of the protein products is due to changes in the frequency of alternative splicing events within a pre-mRNA, leading to changes in the ratio of splice variants produced. In some embodiments, alternative splicing of a pre-mRNA may lead to 2, 3, 4, 5, 6, 7, 8, 9, 10, 11, 12, 13, 14, 15, 16, 17, 18, 19 or 20 protein isoforms being expressed. In some embodiments, a change in the splice variant ratio is caused by genetic mutation.

In eukaryotes, the vast majority of splicing processes are catalyzed by the spliceosome, an RNA-protein complex that occurs in unique steps and may comprise a subset of several hundred different proteins, in addition to five spliceosomal snRNAs. These factors are responsible for the accurate positioning of the spliceosome on the 5' and 3' splice site sequences. The reason why so many factors are needed reflects the observation that exon recognition can be affected by many pre-mRNA features such as exon length, sequence recognition, the presence of enhancer and silencer elements, the strength of upstream splicing signals, the promoter architecture, and the rate of RNA processivity, secondary and tertiary RNA structure.

All mammalian diseases are ultimately mediated by the transcriptome. Insofar as messenger mRNA (mRNA) is part of the transcriptome, and all protein expression derives from mRNAs, there is the potential to intervene in protein-mediated diseases by modulating the expression of the relevant protein and by, in turn, modulating the translation of the corresponding upstream mRNA. But mRNA is only a small portion of the transcriptome: other transcribed RNAs also regulate cellular biology either directly by the structure and function of RNA structures (e.g., ribonucleoproteins) as well as via protein expression and action, including (but not limited to) microRNA (miRNA), long noncoding RNA (lncRNA), long intergenic noncoding RNA (lincRNA), small nucleolar RNA (snoRNA), small nuclear RNA (snRNA), small Cajal body-specific RNA (scaRNA), piwi-interacting RNA (piRNA), competing endogenous (ceRNA), and pseudo-genes. Drugs that intervene at this level have the potential of modulating any and all cellular processes. Existing therapeutic modalities such as antisense RNA or siRNA, in most cases, have yet to overcome significant challenges such as drug delivery, absorption, distribution to target organs, pharmacokinetics, and cell penetration. In contrast, small molecules have a long history of successfully surmounting these barriers and these qualities, which make them suitable as drugs, are readily optimized through a series of analogues to overcome such challenges. In sharp contrast, the application of small molecules as ligands for RNA that yield therapeutic benefit has received little to no attention from the drug discovery community.

DNA sequences in the chromosome are transcribed into pre-mRNAs which contain coding regions (exons) and generally also contain intervening non-coding regions (introns). Introns are removed from pre-mRNAs through splicing. Pre-mRNA splicing proceeds by a two-step mechanism. In the first step, the 5' splice site is cleaved, resulting in a "free" 5' exon and a lariat intermediate. In the second step, the 5' exon is ligated to the 3' exon with release of the intron as the lariat product. These steps are catalyzed in a complex of small nuclear ribonucleoproteins and proteins called the spliceosome.

In most cases, the splicing reaction occurs within the same pre-mRNA molecule, which is termed cis-splicing. Splicing between two independently transcribed pre-mRNAs is termed trans-splicing.

Introns are portions of eukaryotic DNA, which intervene between the coding portions, or "exons," of that DNA. Introns and exons are transcribed into RNA termed "primary transcript, precursor to mRNA" (or "pre-mRNA"). Introns can be removed from the pre-mRNA so that the native protein encoded by the exons can be produced (the term "native protein" as used herein refers to naturally occurring, wild type, or functional protein). The removal of introns from pre-mRNA and subsequent joining of the exons is carried out in the splicing process.

The splicing process is a series of reactions, which are carried out on RNA after transcription but before translation and which are mediated by splicing factors. Thus, a "pre-mRNA" can be an RNA that contains both exons and intron(s), and a mature mRNA ("mRNA") can be an RNA in which the intron(s) have been removed and the exons joined together sequentially so that the protein may be translated therefrom by the ribosomes.

Introns can be defined by a set of "splice elements" that are part of the splicing machinery and may be required for splicing and which are relatively short, conserved RNA segments that bind the various splicing factors, which carry out the splicing reactions. Thus, each intron is defined by a 5' splice site, a 3' splice site, and a branch point situated there between. Splice elements also comprise exon splicing enhancers and silencers, situated in exons, and intron splicing enhancers and silencers situated in introns at a distance from the splice sites and branch points. In addition to splice site and branch points these elements control alternative aberrant and constitutive splicing.

Initial RNA transcripts (pre-mRNA) of most eukaryotic genes are retained in the nucleus until non-coding intron sequences are removed by the spliceosome to produce mature messenger RNA (mRNA). The splicing that occurs can vary, so the synthesis of alternative protein products from the same primary transcript can be affected by tissue-specific or developmental signals. A significant fraction of human genetic diseases, including a number of cancers, are believed to result from deviations in the normal pattern of pre-mRNA splicing. The spliceosome is a complex comprising ribonucleoprotein (snRNP) particles composed of small nuclear RNAs and proteins. snRNA components of the spliceosome can promote the two transesterification reactions of splicing.

Two unique spliceosomes coexist in most eukaryotes: the U2-dependent spliceosome, which catalyzes the removal of U2-type introns, and the less abundant U12-dependent spliceosome, which is present in only a subset of eukaryotes and splices the rare U12-type class of introns. The U2-dependent spliceosome is assembled from the U1, U2, U5, and U4/U6 snRNPs and numerous non-snRNP proteins. The U2 snRNP is recruited with two weakly bound protein subunits, SF3a and SF3b, during the first ATP-dependent step in spliceosome assembly. SF3b is composed of seven conserved proteins, including PHF5a, SF3b155, SF3b145, SF3b130, SF3b49, SF3b14a, and SF3b10.

Splicing or RNA splicing typically refers to the editing of the nascent precursor messenger RNA (pre-mRNA) transcript into a mature messenger RNA (mRNA). Splicing is a biochemical process which includes the removal of introns followed by exon ligation. Sequential transesterification reactions are initiated by a nucleophilic attack of the 5' splice site (5'ss) by the branch adenosine (branch point; BP) in the downstream intron resulting in the formation of an intron lariat intermediate with a 2', 5'-phosphodiester linkage. This is followed by a 5'ss-mediated attack on the 3' splice site (3' ss), leading to the removal of the intron lariat and the formation of the spliced RNA product.

Splicing can be regulated by various cis-acting elements and trans-acting factors. Cis-acting elements are sequences of the mRNA and can include core consensus sequences and other regulatory elements. Core consensus sequences typically can refer to conserved RNA sequence motifs, including the 5'ss, 3'ss, polypyrimidine tract and BP region, which can function for spliceosome recruitment. BP refers to a partially conserved sequence of pre-mRNA, generally less than 50 nucleotides upstream of the 3'ss. BP reacts with the 5'ss during the first step of the splicing reaction. Other regulatory cis-acting elements can include exonic splicing enhancer (ESE), exonic splicing silencer (ESS), intronic splicing enhancer (ISE), and intronic splicing silencer (ISS). Trans-acting factors can be proteins or ribonucleoproteins which bind to cis-acting elements.

Splice site identification and regulated splicing can be accomplished principally by two dynamic macromolecular machines, the major (U2-dependent) and minor (U12-dependent) spliceosomes. Each spliceosome contains five snRNPs: U1, U2, U4, U5 and U6 snRNPs for the major spliceosome (which processes ~95.5% of all introns); and U11, U12, U4atac, U5 and $U_6$ atac snRNPs for the minor spliceosome. Spliceosome recognition of consensus sequence elements at the 5'ss, 3'ss and BP sites is one of the steps in the splicing pathway, and can be modulated by ESEs, ISEs, ESSs, and ISSs, which can be recognized by auxiliary splicing factors, including SR proteins and hnRNPs. Polypyrimidine tract-binding protein (PTBP) can bind to the polypyrimidine tract of introns and may promote RNA looping.

Alternative splicing is a mechanism by which a single gene may eventually give rise to several different proteins. Alternative splicing can be accomplished by the concerted action of a variety of different proteins, termed "alternative splicing regulatory proteins," that associate with the pre-mRNA, and cause distinct alternative exons to be included in the mature mRNA. These alternative forms of the gene's transcript can give rise to distinct isoforms of the specified protein. Sequences in pre-mRNA molecules that can bind to alternative splicing regulatory proteins can be found in introns or exons, including, but not limited to, ISS, ISE, ESS, ESE, and polypyrimidine tract. Many mutations can alter splicing patterns. For example, mutations can be cis-acting elements, and can be located in core consensus sequences (e.g. 5'ss, 3'ss and BP) or the regulatory elements that modulate spliceosome recruitment, including ESE, ESS, ISE, and ISS.

A cryptic splice site, for example, a cryptic 5'ss and a cryptic 3'ss, can refer to a splice site that is not normally recognized by the spliceosome and therefore are in the dormant state. Cryptic splice site can be recognized or activated, for example, by mutations in cis-acting elements or trans-acting factors, or structural configurations, such as bulges.

Splicing Modulation

The present invention contemplates use of small molecules with favorable drug properties that modulate the activity of splicing of a target RNA. Provided herein are small molecule splicing modulators (SMSMs) that modulate splicing of a target polynucleotide. In some embodiments, the SMSMs bind and modulate target RNA. In some embodiments, provided herein is a library of SMSMs that bind and modulate one or more target RNAs. In some embodiments, the target RNA is mRNA. In some embodiments, the target RNA is mRNA a noncoding RNA. In some embodiments, the target RNA is a pre-mRNA. In some embodiments, the target RNA is hnRNA. In some embodiments, the small molecules modulate splicing of the target RNA. In some embodiments, a small molecule provided herein modulates splicing at a sequence of the target RNA. In some embodiments, a small molecule provided herein modulates splicing at a cryptic splice site sequence of the target RNA. In some embodiments, a small molecule provided herein binds to a target RNA. In some embodiments, a small molecule provided herein binds to a splicing complex component. In some embodiments, a small molecule provided herein binds to a target RNA and a splicing complex component.

Thus, provided herein are methods of preventing or inducing a splicing event in a pre-mRNA molecule, comprising contacting the pre-mRNA molecule and/or other elements of the splicing machinery (e.g., within a cell) with a compound provided herein to prevent or induce the splicing event in the pre-mRNA molecule. The splicing event that is prevented or induced can be, e.g., an aberrant splicing event, a constitutive splicing event or an alternate splicing event.

Further provided herein is a method of identifying a compound capable of preventing or inducing a splicing event in a pre-mRNA molecule, comprising contacting the compound with splicing elements and/or factors involved in alternative, aberrant and/or constitutive splicing as described herein (e.g., within cells) under conditions whereby a positive (prevention or induction of splicing) or negative (no prevention or induction of splicing) effect is produced and detected and identifying a compound that produces a positive effect as a compound capable of preventing or inducing a splicing event.

In some embodiments, a small molecule compound described herein in a pharmaceutically acceptable carrier prevents or induces an alternative or aberrant splicing event in a pre-mRNA molecule.

In some embodiments, provided herein is a method of upregulating expression of a native protein in a cell containing a DNA encoding the native protein, wherein the DNA contains a mutation or no mutation that causes down-regulation of the native protein by aberrant and/or alternate splicing thereof. For example, the DNA can encode a pre-mRNA that has a mutation or an aberrant secondary or tertiary structure that causes downregulation of one or more isoforms of a protein. The method can comprise introducing into the cell a small molecule provided herein that prevents an aberrant splicing event, whereby the native intron is removed by correct splicing and the native protein is produced by the cell. In some embodiments, a method comprises introducing into a cell a small molecule provided herein that modulates an alternate splicing event to produce a protein that has a different function than the protein that would be produced without modulation of alternate splicing.

In some embodiments, provided herein is a method of downregulating expression of a native protein in a cell containing a DNA encoding the native protein, wherein the DNA contains a mutation or no mutation that causes upregulation of the native protein by aberrant and/or alternate splicing thereof. For example, the DNA can encode a pre-mRNA that has a mutation or an aberrant secondary or tertiary structure that causes upregulation of one or more isoforms of a protein. The method can comprise introducing into the cell a small molecule provided herein that prevents an aberrant splicing event, whereby the native intron is removed by correct splicing and the native protein is produced by the cell. In some embodiments, a method comprises introducing into a cell a small molecule provided herein that modulates an alternate splicing event to produce a protein that has a different function than the protein that would be produced without modulation of alternate splicing. For example, a method can comprise preventing aberrant splicing in a pre-mRNA molecule containing a mutation or an aberrant secondary or tertiary structure and/or preventing an alternative splicing event. When present in the pre-mRNA, the mutation or aberrant secondary or tertiary structure can cause a pre-mRNA to splice incorrectly and produce an aberrant mRNA or mRNA fragment different from the mRNA ordinarily resulting from a pre-mRNA without the mutation or aberrant secondary or tertiary structure. For example, s pre-mRNA molecule can contain: (i) a first set of splice elements defining a native intron which can be removed by splicing when the mutation or aberrant secondary or tertiary structure is absent to produce a first mRNA molecule encoding a native protein, and (ii) a second set of splice elements induced by the mutation or aberrant secondary or tertiary structure which defines an aberrant intron different from the native intron, which aberrant intron is removed by splicing when the mutation or aberrant secondary or tertiary structure is present to produce an aberrant second mRNA molecule different from the first mRNA molecule. The method can comprise contacting the pre-mRNA molecule and/or other factors and/or elements of the splicing machinery as described herein (e.g., within a cell) with a compound described herein to prevent or promote an aberrant splicing event in a pre-mRNA molecule, whereby the native intron is removed by correct splicing and native protein production is increased in the cell.

Also provided herein is a method of upregulating expression of a RNA that would otherwise be downregulated by modulating an alternative splicing event in the RNA. The method can comprise contacting a pre-mRNA molecule and/or other elements and/or factors of the splicing machinery with a compound described herein to modulate alternate splicing events, whereby a native splicing event is inhibited and an alternate splicing event is promoted that upregulates expression of a RNA that is otherwise downregulated when under the control of the native splicing event.

Also provided herein is a method of downregulating expression of a RNA that would otherwise be upregulated by modulating an alternative splicing event in the RNA. The method can comprise contacting a pre-mRNA molecule and/or other elements and/or factors of the splicing machinery with a compound described herein to modulate alternate splicing events, whereby a native splicing event is inhibited and an alternate splicing event is promoted that downregulates expression of a RNA that is otherwise upregulated when under the control of the native splicing event.

The methods, compounds and compositions described herein have a variety of uses. For example, they are useful in any process where it is desired to have a means for downregulating expression of a RNA to be expressed until a certain time, after which it is desired to upregulate RNA expression. For such use, the RNA to be expressed may be any RNA encoding a protein to be produced so long as the gene contains a native intron. The RNA may be mutated by any suitable means, such as site-specific mutagenesis (see, T. Kunkel, U.S. Pat. No. 4,873,192) to deliberately create an aberrant second set of splice elements which define an aberrant intron which substantially downregulates expression of the gene. A sequence encoding the RNA may be inserted into a suitable expression vector and the expression vector inserted into a host cell (e.g., a eukaryotic cell such as a yeast, insect, or mammalian cell (e.g., human, rat)) by standard recombinant techniques. The host cell can then be grown in culture by standard techniques. When it is desired to upregulate expression of the mutated gene, a suitable compound of the present invention, in a suitable formulation, can be added to the culture medium so that expression of the gene is upregulated.

Also provided herein is a method of altering the ratio of splice variants produced from a gene. The method can comprise contacting a pre-mRNA molecule and/or other elements and/or factors of the splicing machinery with a compound or compounds described herein to modulate alternative splicing events. The compound or compounds of this invention can be used to act upon 1, 2, 3, 4, 5, 6, 7, 8, 9, 10, 11, 12, 13, 14, 15, 16, 17, 18, 19 or 20 alternative splicing events that may occur within a pre-mRNA. In some embodiments, a first splice variant may be downregulated or inhibited and/or a second splice variant may be upregulated, resulting in an altered ratio of splice variants of the two or more RNA. In some embodiments, a first splice variant may be upregulated while a second splice variant may be unaffected, thereby altering the ratio of the RNA. In some embodiments, a first splice variant may be downregulated while a second splicing event may be unaffected thereby altering the ratio of the RNA.

The methods, compounds and formulations described herein are also useful as in vitro or in vivo tools to examine and modulate splicing events in human or animal RNAs encoded by genes, e.g., those developmentally and/or tissue regulated (e.g., alternate splicing events).

The compounds and formulations described herein are also useful as therapeutic agents in the treatment of disease involving aberrant and/or alternate splicing. Thus, in some embodiments, a method of treating a subject having a condition or disorder associated with an alternative or aberrant splicing event in a pre-mRNA molecule, comprises administering to the subject a therapeutically effective amount of a compound described herein to modulate an alternative splicing event or prevent an aberrant splicing event, thereby treating the subject. The method can, e.g., restore a correct splicing event in a pre-mRNA molecule. The method can, e.g., utilize a small molecule compound described herein in a pharmaceutically acceptable carrier.

Formulations containing the small molecules described herein can comprise a physiologically or pharmaceutically acceptable carrier, such as an aqueous carrier. Thus, formulations for use in the methods described herein include, but are not limited to, those suitable for oral administration, parenteral administration, including subcutaneous, intradermal, intramuscular, intravenous and intra-arterial administration, as well as topical administration (e.g., administration of an aerosolized formulation of respirable particles to the lungs of a patient afflicted with cystic fibrosis or lung cancer or a cream or lotion formulation for transdermal administration of patients with psoriasis). The formulations may conveniently be presented in unit dosage form and may be prepared by any of the methods well known in the art. The most suitable route of administration in any given case may depend upon the subject, the nature and severity of the condition being treated, and the particular active compound, which is being used, as would be readily determined by one of skill in the art.

Also provided herein are methods for the use of a compound described herein having the characteristics set forth above for the preparation of a medicament for upregulating or downregulating RNA expression in a patient having a disorder associated with aberrant or alternate splicing of a pre-mRNA molecule, as discussed above. In some embodiments, the medicament upregulates gene expression. In other embodiments, the medicament downregulates gene expression. In the manufacture of at medicament according to the invention, the compound can be admixed with, inter alia, a pharmaceutically acceptable carrier. The carrier may be a solid or a liquid. One or more compounds may be incorporated in any combination in the formulations described herein, which may be prepared by any of the well-known techniques of pharmacy, such as admixing the components, and/or including one or more accessory therapeutic ingredients.

The present inventors identify herein low molecular weight compounds (sometimes referred to herein as small molecules, which block mRNA splicing and/or enhance (facilitate, augment) mRNA splicing. The splicing that can be regulated by the methods described herein include alternative splicing, e.g., exon skipping, intron retention, pseudo-exons skipping, exon exclusion, partial intron exclusion and others. Depending on factors such as the splicing sequence and the RNA (or gene encoding the RNA) or exon involved, modulation of splicing can be accomplished in the presence of, or in the absence of, antisense oligonucleotides (AOs) that are specific for splicing sequences of interest. In some embodiments, a small molecule and an AO act synergistically.

In some aspects, a method comprises contacting a splice modulating compound (e.g., a SMSM) to a pre-mRNA that modulates splicing of the pre-mRNA to favor expression of a transcript that promotes cell proliferation. For example, an SMSM described herein can increase one or more isoforms of a transcript that promotes cell proliferation. For example, an SMSM described herein can decrease expression one or more isoforms of a transcript that prevents or inhibits cell proliferation.

In some aspects, a method comprises contacting a splice modulating compound (e.g., a SMSM) to a pre-mRNA that modulates splicing of the pre-mRNA to favor expression of a transcript that prevents or inhibits cell proliferation. For example, an SMSM described herein can increase one or more isoforms of a transcript that prevents or inhibits cell proliferation. For example, an SMSM described herein can decrease expression one or more isoforms of a transcript that promotes cell proliferation.

In some embodiments, a method of modulating splicing of pre-mRNA comprises using an SMSM to decrease expression or functionality of one or more isoforms of a transcript in a subject. The method can comprise administering an SMSM, or a composition comprising an SMSM, to a subject, wherein the SMSM binds to a pre-mRNA or a splicing complex component and modulates splicing of the pre-mRNA to favor expression of one or more isoforms of a transcript. The method can comprise administering an SMSM, or a composition comprising an SMSM, to a subject, wherein the SMSM binds to a pre-mRNA or a splicing complex component and modulates splicing of the pre-mRNA to disfavor expression of one or more isoforms of a transcript.

In some embodiments, the present invention provides a method of treating a subject afflicted with a disease or condition associated with aberrant splicing of a pre-mRNA. The method can comprise administering an SMSM, or a composition comprising an SMSM, to a subject, wherein the SMSM binds to a pre-mRNA or a splicing complex component and modulates splicing of the pre-mRNA to inhibit expression of one or more isoforms of a transcript. The method can comprise administering an SMSM, or a composition comprising an SMSM, to a subject, wherein the SMSM binds to a pre-mRNA or a splicing complex component and modulates the splicing of the pre-mRNA to increase expression of one or more isoforms of a transcript.

A number of diseases are associated with expression of an aberrant gene product (e.g., an RNA transcript or protein) of a gene. For example, aberrant amounts of a RNA transcript may lead to disease due to corresponding changes in protein expression. Changes in the amount of a particular RNA transcript may be the result of several factors. First, changes in the amount of RNA transcripts may be due to an aberrant level of transcription of a particular gene, such as by the perturbation of a transcription factor or a portion of the transcription process, resulting in a change in the expression level of a particular RNA transcript. Second, changes in the splicing of particular RNA transcripts, such as by perturbation of a particular splicing process or mutations in the gene that lead to modified splicing can change the levels of a particular RNA transcript. Changes to the stability of a particular RNA transcript or to components that maintain RNA transcript stability, such as the process of poly-A tail incorporation or an effect on certain factors or proteins that bind to and stabilize RNA transcripts, may lead to changes in the levels of a particular RNA transcript. The level of translation of particular RNA transcripts can also affect the amount of those transcripts, affecting or upregulating RNA transcript decay processes. Finally, aberrant RNA transport or RNA sequestration may also lead to changes in functional levels of RNA transcripts, and may have an effect on the stability, further processing, or translation of the RNA transcripts.

In some embodiments, provided herein are methods for modulating the amount of one, two, three or more RNA transcripts encoded by a pre-mRNA, comprising contacting a cell with an SMSM compound or a pharmaceutically acceptable salt thereof. In some embodiments, the cell is contacted with an SMSM compound or a pharmaceutically acceptable salt thereof in a cell culture. In other embodiments, the cell is contacted with an SMSM compound or a pharmaceutically acceptable salt thereof in a subject (e.g., a non-human animal subject or a human subject).

In some embodiments, provided herein are methods for treatment, prevention and/or delay of progression of a disease or condition comprising administering an effective amount of a small molecule splicing modulator as described herein to a subject, in particular to a mammal.

In some embodiments, provided herein are compositions and methods for treating a disease or condition, including steric modulator compounds or pharmaceutically acceptable salts thereof that promote prevention or correction of exon skipping of a pre-mRNA. The invention further provides compositions and methods for increasing production of mature mRNA and, in turn, protein, in cells of a subject in need thereof, for example, a subject that can benefit from increased production of protein. The invention further provides compositions and methods for decreasing production of mature mRNA and, in turn, protein, in cells of a subject in need thereof, for example, a subject that can benefit from decreased production of protein. In one embodiment, the described methods may be used to treat subjects having a disease or condition caused by a mutation in a gene, including missense, splicing, frameshift and nonsense mutations, as well as whole gene deletions, which result in deficient protein production. In another embodiment, the described methods may be used to treat subjects having a disease or condition not caused by gene mutation. In some embodiments, the compositions and methods of the present invention are used to treat subjects having a disease or condition, who can benefit from increased production of protein. In some embodiments, the compositions and methods of the present invention are used to treat subjects having a disease or condition, who can benefit from increased production of protein. In some embodiments, the compositions and methods of the present invention are used to treat subjects having a disease or condition, who can benefit from decreased production of a protein.

In some embodiments, provided herein are methods of treating a disease or condition in a subject in need thereof by increasing the expression of a target protein or functional RNA by cells of the subject, wherein the cells have a mutation that causes, e.g., exon skipping or intron inclusion, or a portion thereof, of pre-mRNA, wherein the pre-mRNA encodes the target protein or functional RNA. The method can comprise contacting cells of a subject with an SMSM compound or a pharmaceutically acceptable salt thereof that targets the pre-mRNA encoding the target protein or functional RNA or splicing complex component, whereby splicing of an exon from a pre-mRNA encoding a target protein or functional RNA is prevented or inhibited, thereby increasing a level of mRNA encoding the target protein or functional RNA, and increasing the expression of the target protein or functional RNA in the cells of the subject. In some embodiments, also disclosed herein is a method of increasing expression of a target protein by cells having a mutation or aberrant secondary or tertiary RNA structure that causes exon skipping of pre-mRNA, the pre-mRNA comprising a mutation or aberrant secondary or tertiary RNA structure that causes exon skipping. The method can comprise contacting the cells with an SMSM compound or a pharmaceutically acceptable salt thereof that targets a pre-mRNA encoding a target protein or functional RNA, whereby splicing of an exon from a pre-mRNA encoding a target protein or functional RNA is prevented or inhibited, thereby increasing the level of mRNA encoding functional protein, and increasing the expression of protein in the cells. In some embodiments, the target protein is a tumor suppressor. In some embodiments, the target protein is a tumor promoter. In some embodiments, the target protein or the functional RNA is a compensating protein or a compensating functional RNA that functionally augments or replaces a target protein or functional RNA that is deficient in amount or activity in the subject. In some embodiments, the cells are in or from a subject having a condition caused by a deficient amount or activity of the protein. In some embodiments, the deficient amount of the target protein is caused by haploinsufficiency of the target protein, wherein the subject has a first allele encoding a functional target protein, and a second allele from which the target protein is not produced, or a second allele encoding a nonfunctional target protein, and wherein an SMSM compound or a pharmaceutically acceptable salt thereof binds to a targeted portion of a pre-mRNA transcribed from the first allele. In some embodiments, the target protein is produced in a form that is fully-functional compared to the equivalent protein produced from mRNA in which an exon has been skipped or is missing. In some embodiments, the pre-mRNA is encoded by a genetic sequence with at least about 80%, 85%, 90%, 95%, 96%, 97%, 98%, 99% or 100% sequence identity to a pre-mRNA. In some embodiments, an SMSM compound or a pharmaceutically acceptable salt thereof increases the amount of the target protein or the functional RNA by modulating alternative splicing of pre-mRNA transcribed from a gene encoding the functional RNA or target protein. In some embodiments, an SMSM compound or a pharmaceutically acceptable salt thereof increases the amount of the target protein or the functional RNA by modulating aberrant splicing resulting from mutation of the gene encoding the target protein or the functional RNA.

In some embodiments, the total amount of the mRNA encoding the target protein or functional RNA produced in the cell contacted with an SMSM compound or a pharmaceutically acceptable salt thereof is increased at least about 10%, at least about 20%, at least about 50%, at least about 60%, at least about 70%, at least about 80%, at least about 90%, at least about 100%, at least about 150%, at least about 200%, at least about 250%, at least about 300%, at least about 400%, or at least about 500%, compared to the total amount of the mRNA encoding the target protein or functional RNA produced in a control cell.

In some embodiments, the total amount of the mRNA encoding the target protein or functional RNA produced in the cell contacted with than SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, or about 200% to about 250%, compared to the total amount of the mRNA encoding the target protein or functional RNA produced in a control cell.

In some embodiments, the total amount of target protein produced by the cell contacted with an SMSMS compound or a pharmaceutically acceptable salt thereof is increased at least about 20%, at least about 50%, at least about 100%, at least about 150%, at least about 200%, at least about 250%, or at least about 300%, compared to the total amount of target protein produced by a control cell. In some embodiments, the total amount of target protein produced by the cell contacted with an SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, or about 200% to about 250%, compared to the total amount of target protein produced by a control cell.

In some embodiments, a total amount of the mRNA encoding the target protein or functional RNA produced in the cell contacted with an SMSM compound or a pharmaceutically acceptable salt thereof is increased at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the total amount of the mRNA encoding the target protein or functional RNA produced in a control cell. In some embodiments, a total amount of an mRNA encoding the target protein or functional RNA produced in a cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, or about 4 to about 9-fold, compared to a total amount of the mRNA encoding the target protein or functional RNA produced in a control cell.

In some embodiments, a total amount of target protein produced by a cell contacted with an SMSM compound or a pharmaceutically acceptable salt thereof is increased at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of target protein produced by a control cell. In some embodiments, the total amount of target protein produced by the cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, or about 4 to about 9-fold, compared to a total amount of target protein produced by a control cell.

In some embodiments, the total amount of the mRNA encoding the target protein or functional RNA produced in the cell contacted with an SMSM compound or a pharmaceutically acceptable salt thereof is decreased at least about 10%, at least about 20%, at least about 30%, at least about 40%, at least about 50%, at least about 60%, at least about 70%, at least about 80%, at least about 90%, or at least about 100%, compared to the total amount of the mRNA encoding the target protein or functional RNA produced in a control cell.

In some embodiments, the total amount of the mRNA encoding the target protein or functional RNA produced in the cell contacted with an SMSM compound or a pharmaceutically acceptable salt thereof is decreased about 10% to about 100%, about 20% to about 100%, about 30% to about 100%, about 40% to about 100%, about 50% to about 100%, about 60% to about 100%, about 70% to about 100%, about 80% to about 100% about 90% to about 100%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, 70% to about 80%, about 70% to about 90%, or about 80% to about 90%, compared to the total amount of the mRNA encoding the target protein or functional RNA produced in a control cell.

In some embodiments, the total amount of target protein produced by the cell contacted with an SMSM compound or a pharmaceutically acceptable salt thereof is decreased at least about 10%, at least about 20%, at least about 30%, at least about 40%, at least about 50%, at least about 60%, at least about 70%, at least about 80%, at least about 90%, or at least about 100%, compared to the total amount of target protein produced by a control cell. In some embodiments, the total amount of target protein produced by the cell contacted with an SMSM compound or a pharmaceutically acceptable salt thereof is decreased about 10% to about 100%, about 20% to about 100%, about 30% to about 100%, about 40% to about 100%, about 50% to about 100%, about 60% to about 100%, about 70% to about 100%, about 80% to about 100% about 90% to about 100%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, 70% to about 80%, about 70% to about 90%, or about 80% to about 90%, compared to the total amount of target protein produced by a control cell.

In some embodiments, the difference in amount between a first splice variant and a second splice variant encoding a target protein or functional RNA isoform produced in the cell contacted with an SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to the difference in amounts between the two splice variants produced by a control cell. In some embodiments, the difference in amount between a first protein isoform expressed from a first splice variant and a second protein isoform expressed from a second splice variant produced by the cell contacted with an SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200 to about 250%, at least about 20%, at least about 50%, at least about 100%, at least about 150%, at least about 200%, at least about 250%, or at least about 300%, compared to the difference in amounts between two protein isoforms produced from the splice variants produced by a control cell.

In some embodiments, the difference in amount between a first splice variant and a second splice variant encoding a target protein or functional RNA isoform produced in the cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between the two splice variants produced by a control cell. In some embodiments, the difference in amount between a first protein isoform expressed from a first splice variant and a second protein isoform expressed from a second splice variant produced by the cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between two protein isoforms expressed from the splice variants produced by a control cell.

In some embodiments, a difference in amount between a first splice variant and a second splice variant encoding a target protein or functional RNA isoform produced in a cell contacted with an SMSM compound or a pharmaceutically acceptable salt thereof is decreased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to the difference in amounts between the two splice variants produced by a control cell. In some embodiments, a difference in amount between a first protein isoform expressed from a first splice variant and a second protein isoform expressed from a second splice variant produced by a cell contacted with an SMSM compound or a pharmaceutically acceptable salt thereof is decreased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to a difference in amounts between two protein isoforms produced from the splice variants produced by a control cell.

In some embodiments, the difference in amount between a first splice variant and a second splice variant encoding a target protein or functional RNA isoform produced in the cell contacted with an SMSM compound or a pharmaceutically acceptable salt thereof is decreased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between the two splice variants produced by a control cell. In some embodiments, the difference in amount between a first protein isoform expressed from a first splice variant and a second protein isoform expressed from a second splice variant produced by the cell contacted with an SMSM compound or a pharmaceutically acceptable salt thereof is decreased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between two protein isoforms express from the splice variants produced by a control cell.

The ratio of a first isoform and a second isoform may contribute to a number of conditions or diseases. In some embodiments, a subject without a condition or disease has a first isoform to second isoform ratio of 1:1. In some embodiments, a subject with a condition or disease described herein has a first isoform to second isoform ratio of about 1:1.2, 1:1.4, 1:1.6, 1:1.8, 1:2, 1:2.5, 1:3, 1:3.5, 1:4, 1:4.5 or 1:5. In some embodiments, a subject with a condition or disease described herein has a first isoform to second isoform ratio from about 1:1 to about 1:1.1, about 1:1 to about 1:1.2, about 1:1 to about 1:1.3, about 1:1 to about 1:1.4, about 1:1 to about 1:1.5, about 1:1 to about 1:1.6, about 1:1 to about 1:1.8, about 1:1 to about 1:2, about 1:1 to about 1:3, about 1:1 to about 1:3.5, about 1:1 to about 1:4, about 1:1 to about 1:4.5, about 1:1 to about 1:5, 1:2 to about 1:3, about 1:2 to about 1:4, about 1:2 to about 1:5, about 1:3 to about 1:4, about 1:3 to about 1:5, or about 1:4 to about 1:5.

In some embodiments, binding of an SMSM compound or a pharmaceutically acceptable salt thereof to pre-mRNA prevents splicing out of one or more exons and/or introns and/or proteins thereof, from the population of pre-mRNAs to produce mRNA encoding the target protein or functional RNA. In some embodiments, the cell comprises a population of pre-mRNAs transcribed from the gene encoding the target protein or functional RNA, wherein the population of pre-mRNAs comprises a mutation that causes the splicing out of one or more exons, and wherein an SMSM compound or a pharmaceutically acceptable salt thereof binds to the mutation that causes the splicing out of the one or more exons in the population of pre-mRNAs. In some embodiments, the binding of an SMSM compound or a pharmaceutically acceptable salt thereof to the mutation that causes the splicing out of the one or more exons prevents splicing out of the one or more exons from the population of pre-mRNAs to produce mRNA encoding the target protein or functional RNA. In some embodiments, the condition is a disease or disorder. In some embodiments, the method further comprises assessing protein expression. In some embodiments, an SMSM compound or a pharmaceutically acceptable salt thereof binds to a targeted portion of a pre-mRNA.

In some embodiments, the binding of an SMSM compound or a pharmaceutically acceptable salt thereof catalyzes the inclusion of a missing exon or removal of an undesired retained intron or portions thereof, resulting in healthy mRNA and proteins. In some embodiments, the binding of an SMSM compound or a pharmaceutically acceptable salt thereof has minimal to no effect on non-diseased cells.

In some embodiments, an SMSM kills cells at an $IC_{50}$ of less than 50 nM. In some embodiments, the cells are primary cells. In some embodiments, an SMSM kills the cells at an IC$_{50}$ of less than 48 nM, 45 nM, 40 nM, 35 nM, 30 nM, 25 nM, 20 nM, 15 nM, 10 nM, 5 nM, 3 nM, or 1 nM.

In some embodiments, an SMSM modulates splicing at a splice site sequence of a polynucleotide of the primary cells. In some embodiments, an SMSM modulates proliferation or survival of the primary cells. In some embodiments, the primary cells are primary diseased cells. In some embodiments, the primary diseased cells are primary cancer cells. In some embodiments, the SMSM is present at a concentration of at least about 1 nM, 10 nM, 100 nM, 1 µM, 10 µM, 100 µM, 1 mM, 10 mM, 100 mM, or 1 M. In some embodiments, at least about 5%, 10%, 25%, 30%, 40%, 50%, 60%, 70%, 75%, 80%, 85%, 90%, 95%, 97%, 98%, 99% or 100% of the primary diseased cells are killed. In some embodiments, at least about 5%, 10%, 25%, 30%, 40%, 50%, 60%, 70%, 75%, 80%, 85%, 90%, 95%, 97%, 98%, 99% or 100% of the primary diseased cells undergo apoptosis. In some embodiments, at least about 5%, 10%, 25%, 30%, 40%, 50%, 60%, 70%, 75%, 80%, 85%, 90%, 95%, 97%, 98%, 99% or 100% of the primary diseased cells undergo necrosis. In some embodiments, proliferation is reduced or inhibited in at least about 5%, 10%, 25%, 30%, 40%, 50%, 60%, 70%, 75%, 80%, 85%, 90%, 95%, 97%, 98%, 99% or 100% of the primary diseased cells. In some embodiments, the primary diseased cells are non-transformed cells.

In some embodiments, an SMSM reduces a size of a tumor in a subject. In some embodiments, a size of a tumor in a subject administered an SMSM or a pharmaceutically acceptable salt thereof is reduced by at least about 1%, 5%, 10%, 15%, 20%, 25%, 30%, 35%, 40%, 45%, 50%, 55%, 60%, 70%, 75%, 80%, 85%, 90%, 95%, 96%, 97%, 98%, or 99% in the subject. In some embodiments, a diameter of a tumor in a subject administered an SMSM or a pharmaceutically acceptable salt thereof is reduced by at least about 1%, 5%, 10%, 15%, 20%, 25%, 30%, 35%, 40%, 45%, 50%, 55%, 60%, 70%, 75%, 80%, 85%, 90%, 95%, 96%, 97%, 98%, or 99%. In some embodiments, a volume of the tumor is reduced by at least about 1%, 5%, 10%, 15%, 20%, 25%, 30%, 35%, 40%, 45%, 50%, 55%, 60%, 70%, 75%, 80%, 85%, 90%, 95%, 96%, 97%, 98%, or 99% in the subject. In some embodiments, the tumor is malignant.

In some embodiments, a method comprises contacting an SMSM to primary non-diseased cells. In some embodiments, at most about 1%, 5%, 10%, 15%, 20%, 25%, or 50% of the primary non-diseased cells are killed. In some embodiments, at most about 1%, 5%, 10%, 15%, 20%, 25%, or 50% of the primary non-diseased cells undergo apoptosis. In some embodiments, at most about 1%, 5%, 10%, 15%, 20%, 25%, or 50% of the primary non-diseased cells undergo necrosis. In some embodiments, proliferation is reduced or inhibited in at most about 1%, 5%, 10%, 15%, 20%, 25%, or 50% of the primary non-diseased cells. In some embodiments, the primary non-diseased cells are of the same tissue as the primary diseased cells. In some embodiments, the primary non-diseased cells are differentiated cells.

An SMSM can modulate splicing at a splice site of a polynucleotide and does not exhibit significant toxicity. In some embodiments, an SMSM penetrates the blood brain barrier (BBB) when administered to a subject.

In some embodiments, an SMSM has a brain/blood AUC of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 40, or higher.

In some embodiments, an SMSM has a half-life of at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, or 1000 hours in a human.

In some embodiments, an SMSM is stable at room temperature for at least 1, 2, 3, 4, 5, 6, 7, 8, 9, 10, 11, 12, 13, 14, 15, 16, 17, 18, 19, 20, 21, 22, 23 or 24 hours; or at least 1, 2, 3, 4, 5, 6, 7, 8, 9, 10, 11, or 12 months; or at least 1, 2, 3, 4, or 5 years. In some embodiments, an SMSM is stable at 4° C. for at least 1, 2, 3, 4, 5, 6, 7, 8, 9, 10, 11, 12, 13, 14, 15, 16, 17, 18, 19, 20, 21, 22, 23 or 24 hours; or for at least 1, 2, 3, 4, 5, 6, 7, 8, 9, 10, 11, or 12 months; or at least 1, 2, 3, 4, or 5 years. In some embodiments, an SMSM is stable at room temperature in water or an organic solvent for at least 1, 2, 3, 4, 5, 6, 7, 8, 9, 10, 11, 12, 13, 14, 15, 16, 17, 18, 19, 20, 21, 22, 23 or 24 hours; or at least 1, 2, 3, 4, 5, 6, 7, 8, 9, 10, 11, or 12 months; or at least 1, 2, 3, 4, or 5 years. In some embodiments, an SMSM is stable at 4° C. in water or an organic solvent for at least 1, 2, 3, 4, 5, 6, 7, 8, 9, 10, 11, 12, 13, 14, 15, 16, 17, 18, 19, 20, 21, 22, 23 or 24 hours; or for at least 1, 2, 3, 4, 5, 6, 7, 8, 9, 10, 11, or 12 months; or at least 1, 2, 3, 4, or 5 years.

In some embodiments, an SMSM has an cell viability IC$_{50}$ of 0.01-10 nM, 0.01-5 nM, 0.01-2.5 nM, 0.01-1 nM, 0.01-0.75 nM, 0.01-0.5 nM, 0.01-0.25 nM, 0.01-0.1 nM, 0.1-100 nM, 0.1-50 nM, 0.1-25 nM, 0.1-10 nM, 0.1-7.5 nM, 0.1-5 nM, 0.1-2.5 nM, 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM.

In some embodiments, an SMSM has an cell viability IC$_{50}$ of at most 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, or 10 µM.

In some embodiments, an SMSM reduces cell proliferation of diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when the cells are treated with the SMSM at a concentration of 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces cell proliferation of diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when the cells are treated with the SMSM at a concentration of at least 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 μM, or 10 μM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces viability of diseased cells by more than 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. when the cells are treated with the SMSM at a concentration of 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces viability of diseased cells by more than 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when the cells are treated with the SMSM at a concentration of at least 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 μM, or 10 μM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM does not reduce viability of non-diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, or 50 when the cells are treated with the SMSM at a concentration of 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM does not reduce viability of non-diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, or 50% when the cells are treated with the SMSM at a concentration of at least 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 μM, or 10 μM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces a size of a tumor in a subject by at least 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, an SMSM inhibits tumor growth of a tumor in a subject by at least 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

SMSM Targets

Aberrant splicing of mRNA, such as pre-mRNA, can result in a defective protein and can cause a disease or a disorder in a subject. The compositions and methods described herein can reduce this aberrant splicing of mRNA, such as pre-mRNA, and treat a disease or a disorder caused by this aberrant splicing.

Diseases associated with changes to RNA transcript amount are often treated with a focus on the aberrant protein expression. However, if the processes responsible for the aberrant changes in RNA levels, such as components of the splicing process or associated transcription factors or associated stability factors, could be targeted by treatment with a small molecule, it would be possible to restore protein expression levels such that the unwanted effects of the expression of aberrant levels of RNA transcripts or associated proteins. Therefore, there is a need for methods of modulating the amount of RNA transcripts encoded by certain genes as a way to prevent or treat diseases associated with aberrant expression of the RNA transcripts or associated proteins.

Structural Targets

Mutations and/or aberrant secondary or tertiary RNA structures in cis-acting elements can induce three-dimensional structural change in pre-mRNA. Mutations and/or aberrant secondary RNA structures in cis-acting elements can induce three-dimensional structural change in pre-mRNA when the pre-mRNA is, for example, bound to at least one snRNA, or at least one snRNP, or at least one other auxiliary splicing factor. For example, non-canonical base pairing of a non-canonical splice site sequence to a snRNA can form a bulge. For example, a bulge can be formed when the 5'ss is bound to U1-U12 snRNA or a portion thereof. For example, a bulge can be induced to form when 5'ss containing at least one mutation is bound to U1-U12 snRNA or a portion thereof. For example, a bulge can be formed when the cryptic 5'ss is bound to U1-U12 snRNA or a portion thereof. For example, a bulge can be induced to form when cryptic 5'ss containing at least one mutation is bound to U1-U12 snRNA or a portion thereof. For example, a bulge can be formed when the 3'ss is bound to U2 snRNA or a portion thereof. For example, a bulge can be induced to form when the 3'ss is bound to U2 snRNA or a portion thereof. For example, a bulge can be formed when the cryptic 3'ss is bound to U2 snRNA or a portion thereof. For example, a bulge can be induced to form when the cryptic 3'ss is bound to U2 snRNA or a portion thereof. The protein components of U1 and U2 may or may not present to form the bulge.

In some embodiments, a small molecule can bind to a bulge. In some embodiments, a bulge is naturally occurring. In some embodiments, a bulge is formed by non-canonical base-pairing between the splice site and the small nuclear RNA. For example, a bulge can be formed by non-canonical base-pairing between the 5' ss and U1-U12 snRNA. The bulge can comprise 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, or 15 nucleotides. In some embodiments, 3-dimensional structural changes can be induced by a mutation without bulge formation. In some embodiments, a bulge may be formed without any mutation in a splice site. In some embodiments, a recognition portion can be formed by a mutation in any of the cis-acting elements. In some embodiments, a small molecule can bind to a recognition portion that is induced by a mutation. In some embodiments, a mutation and/or aberrant secondary or tertiary RNA structure at an authentic 5' splice site can result in splicing at a cryptic 5' splice site. In some embodiments, a mutation and/or aberrant secondary or tertiary RNA structure can be in one of the regulatory elements including ESEs, ESSs, ISEs, and ISSs.

In some embodiments, a target of an SMSM is a pre-mRNA comprising a splice site sequence with a bulged nucleotide in an exon. In some embodiments, a target of an SMSM is a pre-mRNA comprising a splice site sequence with a bulged nucleotide upstream (5') of the splice site of the splice site sequence. In some embodiments, a target of an SMSM is a pre-mRNA comprising a splice site sequence with a bulged nucleotide at the −1 position relative to the splice site of the splice site sequence. For example, a target of an SMSM can be a pre-mRNA comprising a splice site sequence of NNN*nnnnnn, wherein N* represents a bulged nucleotide. In some embodiments, a target of an SMSM is a pre-mRNA comprising a splice site sequence with a bulged nucleotide at the −2 position relative to the splice site of the splice site sequence. For example, a target of an SMSM can be a pre-mRNA comprising a splice site sequence of NN*Nnnnnnn, wherein N* represents a bulged nucleotide. In some embodiments, a target of an SMSM is a pre-mRNA comprising a splice site sequence with a bulged nucleotide at the −3 position relative to the splice site of the splice site sequence. For example, a target of an SMSM can be a pre-mRNA comprising a splice site sequence of N*NNnnnnnn, wherein N* represents a bulged nucleotide.

In some embodiments, a target of an SMSM is a pre-mRNA comprising a splice site sequence with a bulged nucleotide in an intron. In some embodiments, a target of an SMSM is a pre-mRNA comprising a splice site sequence with a bulged nucleotide downstream (3') of the splice site of the splice site sequence.

In some embodiments, a target of an SMSM is a pre-mRNA comprising a splice site sequence with a bulged nucleotide at the +1 position relative to the splice site of the splice site sequence. For example, a target of an SMSM can be a pre-mRNA comprising a splice site sequence of NNNn*nnnnn, wherein n* represents a bulged nucleotide. In some embodiments, a target of an SMSM is a pre-mRNA comprising a splice site sequence with a bulged nucleotide at the +2 position relative to the splice site of the splice site sequence. For example, a target of an SMSM can be a pre-mRNA comprising a splice site sequence of NNNnn*nnnn, wherein n* represents a bulged nucleotide. In some embodiments, a target of an SMSM is a pre-mRNA comprising a splice site sequence with a bulged nucleotide at the +3 position relative to the splice site of the splice site sequence. For example, a target of an SMSM can be a pre-mRNA comprising a splice site sequence of NNNnnn*nnn, wherein n* represents a bulged nucleotide. In some embodiments, a target of an SMSM is a pre-mRNA comprising a splice site sequence with a bulged nucleotide at the +4 position relative to the splice site of the splice site sequence. For example, a target of an SMSM can be a pre-mRNA comprising a splice site sequence of NNNnnnn*nn, wherein n* represents a bulged nucleotide. In some embodiments, a target of an SMSM is a pre-mRNA comprising a splice site sequence with a bulged nucleotide at the +5 position relative to the splice site of the splice site sequence. For example, a target of an SMSM can be a pre-mRNA comprising a splice site sequence of NNNnnnnn*n, wherein n* represents a bulged nucleotide. In some embodiments, a target of an SMSM is a pre-mRNA comprising a splice site sequence with a bulged nucleotide at the +6 position relative to the splice site of the splice site sequence. For example, a target of an SMSM can be a pre-mRNA comprising a splice site sequence of NNNnnnnnn*, wherein n* represents a bulged nucleotide. In some embodiments, a target of an SMSM is a pre-mRNA comprising a splice site sequence with a bulged nucleotide at the +7 position relative to the splice site of the splice site sequence. For example, a target of an SMSM can be a pre-mRNA comprising a splice site sequence of NNNnnnnnnn*, wherein n* represents a bulged nucleotide.

In some embodiments, a target of an SMSM is a pre-mRNA comprising a splice site sequence with one or more bulged nucleotides at the −1, −2, −3, +1, +2, +3, +4, +5, +6 and/or +7 position relative to the splice site of the splice site sequence. For example, a target of an SMSM can be a pre-mRNA comprising a splice site sequence of NNN*nnnnnn, NN*Nnnnnnn, N*NNnnnnnn, NNNn*nnnnn, NNNnn*nnnn, NNNnnn*nnn, NNNnnnn*nn, NNNnnnnn*n, NNNnnnnnn*, or NNNnnnnnnn*, wherein N* or n* represents a bulged nucleotide.

In some embodiments, a target of an SMSM is a pre-mRNA comprising a splice site sequence with one or more bulged nucleotides at the −1, −2, and/or −3 position relative to the splice site of the splice site sequence. For example, a target of an SMSM can be a pre-mRNA comprising a splice site sequence of NNN*nnnnnn, NN*Nnnnnnn, or N*NNnnnnnn, wherein N* represents a bulged nucleotide.

In some embodiments, a target of an SMSM is a pre-mRNA comprising a splice site sequence with one or more bulged nucleotides at the +1, +2, +3, +4, +5, +6 and/or +7 position relative to the splice site of the splice site sequence. For example, a target of an SMSM can be a pre-mRNA comprising a splice site sequence of NNNn*nnnnn, NNNnn*nnnn, NNNnnn*nnn, NNNnnnn*nn, NNNnnnnn*n, NNNnnnnnn*, or NNNnnnnnnn*, wherein n* represents a bulged nucleotide.

In some embodiments, a target of an SMSM is a pre-mRNA comprising a splice site sequence with a bulged nucleotide at the −1 position relative to the splice site of the splice site sequence and a bulged nucleotide at the −2 position relative to the splice site of the splice site sequence. For example, a target of an SMSM can be a pre-mRNA comprising a splice site sequence of NN*N*nnnnnn, wherein N* represents a bulged nucleotide. In some embodiments, a target of an SMSM is a pre-mRNA comprising a splice site sequence with a bulged nucleotide at the −2 position relative to the splice site of the splice site sequence and a bulged nucleotide at the −3 position relative to the splice site of the splice site sequence. For example, a target of an SMSM can be a pre-mRNA comprising a splice site sequence of N*N*Nnnnnnn, wherein N* represents a bulged nucleotide.

In some embodiments, an SMSM interacts with a bulged nucleotide of an RNA duplex comprising a splice site. In some embodiments, the RNA duplex comprises pre-mRNA. In some embodiments, an SMSM binds to an RNA duplex and interacts with an unpaired bulged nucleobase of an RNA duplex comprising a splice site. In some embodiments, a first portion of the SMSM interacts with the bulged nucleotide on a first RNA strand of the RNA duplex. In some embodiments, a second portion of the SMSM interacts with one or more nucleotides of a second RNA strand of the RNA duplex, wherein the first RNA strand is not the second RNA strand. In some embodiments, the SMSM forms one or more intermolecular interactions with the duplex RNA, for example, an ionic interaction, a hydrogen bond, a dipole-dipole interaction or a van der Waals interaction. In some embodiments, the SMSM forms one or more intermolecular interactions with the bulged nucleotide, for example, an ionic interaction, a hydrogen bond, a dipole-dipole interaction or a van der Waals interaction.

In some embodiments, the duplex RNA comprises an alpha helix. In some embodiments, the bulged nucleotide is located on an external portion of a helix of the duplex RNA. In some embodiments, the bulged nucleotide is located within an internal portion of the helix of the duplex RNA.

In some embodiments, a rate of exchange of the bulged nucleotide from within the interior of a helix of the duplex RNA to an exterior portion of the helix is reduced.

In some embodiments, the SMSM modulates a distance of the bulged nucleotide from a second nucleotide of the duplex RNA. In some embodiments, the SMSM reduces the distance of the bulged nucleotide from a second nucleotide of the duplex RNA. In some embodiments, the SMSM increases the distance of the bulged nucleotide from a second nucleotide of the duplex RNA.

In some embodiments, the bulged nucleotide is located within the interior of a helix of the duplex RNA of the complex. In some embodiments, the bulged nucleotide has modulated base stacking within an RNA strand of the RNA duplex. In some embodiments, the bulged nucleotide has increased base stacking within an RNA strand of the RNA duplex. In some embodiments, the bulged nucleotide has decreased base stacking within an RNA strand of the RNA duplex.

In some embodiments, the SMSM modulates splicing at the splice site of the RNA duplex. In some embodiments, the SMSM increases splicing at the splice site of the RNA duplex. In some embodiments, the SMSM reduces splicing at the splice site of the RNA duplex. In some embodiments, the SMSM reduces a size of a bulge of the RNA duplex. In some embodiments, the SMSM removes a bulge of the RNA duplex. In some embodiments, the SMSM stabilizes a bulge of the RNA duplex.

In some embodiments, the unpaired bulged nucleotide is free to rotate around a phosphate backbone of an RNA strand of the RNA duplex in the absence of the SMSM. In some embodiments, the SMSM reduces a rate of rotation of the unpaired bulged nucleotide. In some embodiments, the SMSM reduces a rate of rotation of the unpaired bulged nucleotide around a phosphate backbone of an RNA strand of the RNA duplex.

In some embodiments, the SMSM is not an aptamer.

Also, provided herein is a method of modulating splicing comprising contacting a small molecule splicing modulator compound (SMSM) to a cell; wherein the SMSM interacts with an unpaired bulged nucleotide of an RNA duplex in the cell; wherein the duplex RNA comprises a splice site; and wherein the SMSM modulates splicing of the RNA duplex.

Provided herein is a method for modulating the relative position of a first nucleotide relative to a second nucleotide, wherein the first nucleotide and the second nucleotide are within a duplex RNA, the method comprising contacting a small molecule splicing modulator compound (SMSM) to the duplex RNA, or a pharmaceutically acceptable salt thereof, wherein the first nucleotide is a bulged nucleotide of the RNA duplex; wherein the duplex RNA comprises a splice site.

In some embodiments, the duplex RNA comprises a helix.

In some embodiments, the bulged nucleotide is located on an external portion of a helix of the duplex RNA prior to contacting the SMSM.

In some embodiments, SMSM forms one or more intermolecular interactions with the duplex RNA.

In some embodiments, the SMSM forms one or more intermolecular interactions with an unpaired bulged nucleotide. In some embodiments, the intermolecular interaction is selected from the group comprising an ionic interaction, a hydrogen bond, a dipole-dipole interaction or a van der Waals interaction. In some embodiments, a rate of exchange of the unpaired bulged nucleotide from within the interior of a helix of the duplex RNA to an exterior portion of the helix is reduced. In some embodiments, a rate of rotation of the unpaired bulged nucleotide is reduced. In some embodiments, a rate of rotation of the unpaired bulged nucleotide around a phosphate backbone of an RNA strand of the RNA duplex is reduced. In some embodiments, a distance of the unpaired bulged nucleotide from a second nucleotide of the duplex RNA is modulated after contacting the SMSM. In some embodiments, the distance of the unpaired bulged nucleotide from a second nucleotide of the duplex RNA is reduced. In some embodiments, unpaired bulged nucleotide is located within the interior of the helix of the duplex RNA. In some embodiments, a size of a bulge of the RNA duplex is reduced. In some embodiments, a bulge of the RNA duplex is removed or maintained.

In some embodiments, splicing at the splice site of the RNA duplex is promoted. In some embodiments, base stacking of the unpaired bulged nucleotide within an RNA strand of the RNA duplex is increased after contacting the SMSM. In some embodiments, the distance of the unpaired bulged nucleotide from a second nucleotide of the duplex RNA is increased or maintained. In some embodiments, a bulge of the RNA duplex is stabilized after contacting the SMSM. In some embodiments, the unpaired bulged nucleotide is located on an exterior portion of a helix of the duplex RNA. In some embodiments, a size of a bulge of the RNA duplex is increased. In some embodiments, splicing at the splice site of the RNA duplex is inhibited. In some embodiments, splicing is inhibited at the splice site. In some embodiments, base stacking of the unpaired bulged nucleotide within an RNA strand of the RNA duplex is reduced after contacting the SMSM.

Exemplary sites targeted by the SMSMs described herein include 5' splice sites, 3' splice sites, polypyrimidine tracts, branch sites, splicing enhancers and silencer elements. Mutations or aberrant secondary or tertiary RNA structures at hot spots can create mRNA sites or scaffold sequences that can be targeted. For example, many exons are flanked by the intronic dinucleotides GT and AG at the 5' and 3' splice sites, respectively. For example, mutations or aberrant secondary or tertiary RNA structures at these sites can cause, e.g., exclusion of an adjacent exon or inclusion of an adjacent intron. Many factors influence the complex pre-mRNA splicing process, including several hundred different proteins, at least five spliceosomal snRNAs, sequences on the mRNA, sequence length, enhancer and silencer elements, and strength of splicing signals. Exemplary sites targeted by the SMSMs described herein include secondary and sometimes tertiary structures of RNA. For example, exemplary sites targeted by the SMSMs described herein include a stem loop, hairpin, branch point sequence (BPS), polypyrimidine tract (PPT), 5' splice site (5'ss) and 3' splice site (3'ss), duplex snRNA and splice sites and trans acting protein binding to RNA. The target pre-mRNA can comprise a defective sequence, such as a sequence that produces a deficient protein, such as a protein with altered function such as enzyme activity, or expression, such as lack of expression. In some embodiments, the defective sequence impacts the structure of the RNA. In some embodiments, the defect sequence impacts recognition by snRNP.

In addition to consensus splice site sequences, structural constraints, including those resulting from mutations, can affect cis-acting sequences such as exonic/intronic splicing enhancers (ESE/ISE) or silencer elements (ESS/ISS).

In some embodiments, a mutation in native DNA and/or pre-mRNA, or an aberrant secondary or tertiary structure of RNA, creates a new splice site sequence. For example, a mutation or aberrant RNA structure may cause native regions of the RNA that are normally dormant, or play no role as splicing elements, to become activated and serve as splice sites or splice elements. Such splice sites and elements can be referred to as "cryptic". For example, a native intron may become divided into two aberrant introns, with a new exon situated there between. For example, a mutation may create a new splice site between a native 5' splice site and a native branch point. For example, a mutation may activate a cryptic branch point sequence between a native splice site and a native branch point. For example, a mutation may create a new splice site between a native branch point and a native splice site and may further activate a cryptic splice site and a cryptic branch point sequentially upstream from the aberrant mutated splice site.

In some embodiments, a mutation or misexpression of trans-acting proteins that regulate splicing activity may cause native regions of the RNA that are normally dormant, or play no role as splicing elements, to become activated and serve as splice sites or splice elements. For example, a mutation or misexpression of an SR protein may cause native regions of the RNA that are normally dormant, or play no role as splicing elements, to become activated and serve as splice sites or splice elements.

In some embodiments, a mutation in native DNA and/or pre-mRNA inhibits splicing at a splice site. For example, a mutation may result in a new splice site upstream from (i.e., 5' to) a native splice site sequence and downstream from (i.e., 3' to) a native branch point sequence. The native splice site sequence and the native branch point sequence may serve as members of both the native set of splice site sequences and the aberrant set of splice site sequences.

In some embodiments, a native splice element (e.g., a branch point) is also a member of the set of aberrant splice elements. For example, SMSMs provided herein can block the native element and activate a cryptic element (e.g., a cryptic 5'ss, a cryptic 3' ss or a cryptic branch point), which may recruit remaining members of the native set of splice elements to promote correct splicing over incorrect splicing. In some embodiments, an activated cryptic splice element is in an intron. In some embodiments, an activated cryptic splice element is in an exon. The compounds and methods provided herein can be used to block or activate a variety of different splice elements, depending on the type of aberrant splice element (e.g., mutated splice element or non-mutated splice element) and/or depending on regulation of a splice element (e.g., regulation by upstream signaling pathways). For example, the compounds and methods provided herein can block a mutated element, a non-mutated element, a cryptic element, or a native element; it may block a 5' splice site, a 3' splice site, or a branch point.

In some embodiments, an alternate splicing event can be modulated by employing the compounds provided herein. For example, a compound provided herein can be introduced into a cell in which a gene is present that encodes a pre-mRNA that comprises alternate splice sites. In some embodiments, in the absence of the compound, a first splicing event occurs to produce a gene product having a particular function. For example, in the presence of the compound provided herein, the first splicing event can be inhibited. In some embodiments, in the presence of the compound provided herein, the first splicing event can be inhibited and a second or alternate splicing event occurs, resulting in expression of the same gene to produce a gene product having a different function.

In some embodiments, a first inhibited splicing event (e.g., a splicing event inhibited by a mutation, a mutation-induced bulge or a non-mutation induced bulge), is promoted or enhanced in the presence of a compound provided herein. In some embodiments, the first inhibited splicing event (e.g., a splicing event inhibited by a mutation, a mutation-induced bulge or a non-mutation induced bulge), is promoted or enhanced in the presence of a compound provided herein. For example, the inhibition of the first splicing event (e.g., a splicing event inhibited by a mutation, a mutation-induced bulge or a non-mutation induced bulge) can be restored to a corresponding first splicing event that is uninhibited, in the presence of a compound provided herein; or the inhibition of the first splicing event can be decreased, in the presence of a compound provided herein. In some embodiments, a second or alternate splicing event occurs, resulting in expression of the same gene to produce a gene product having a different function.

Methods of Treatment

In certain embodiments, also described herein is a method of treating cancer in a mammal in need thereof comprising administering a therapeutically effective amount of a splice modifying compound described herein or a pharmaceutically acceptable salt or solvate thereof, to the mammal in need thereof.

In some embodiments, described herein is a method of treating cancer in a subject in need thereof comprising administering to the subject in need thereof a therapeutically effective amount of a splice modifying compound described herein.

In a particular embodiment, the present disclosure relates to the use of a FOXM1 gene splicing modifier as described herein for the preparation of a medicament for the treatment, prevention and/or delay of progression of cancer. In some embodiments, a FOXM1 gene is a human FOXM1 gene In a particular embodiment, the present disclosure relates to the use of a FOXM1 gene splicing modifier as described herein for the treatment, prevention and/or delay of progression of cancer. In some embodiments, a FOXM1 gene splicing modifier described herein induces a transcriptionally inactive FOXM1 variant.

In a particular embodiment, the present disclosure relates to a method for the treatment, prevention and/or delay of progression of cancer comprising administering an effective amount of a FOXM1 gene splicing modifier as described herein to a subject, in particular to a mammal.

In a particular embodiment, the present disclosure relates to a pharmaceutical composition comprising a FOXM1 gene splicing modifier as described herein for use in the treatment, prevention and/or delay of progression of cancer.

In specific embodiments, the cancer treated by the compounds of the present disclosure is selected from the group consisting of cancer of the liver, prostate, brain, breast, lung, colon, pancreas, skin, cervix, ovary, mouth, blood and nervous system In specific embodiments, the cancer treated by the compounds of the present disclosure is leukemia, acute myeloid leukemia, colon cancer, gastric cancer, macular degeneration, acute monocytic leukemia, breast cancer, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Hodgkin's lymphoma, ovarian cancer, non-Hodgkin's lymphoma, multiple myeloma, chronic myeloid leukemia, acute lymphoblastic leukemia, renal cell carcinoma, transitional cell carcinoma, colorectal cancer, chronic lymphocytic leukemia, anaplastic large cell lymphoma, kidney cancer, breast cancer, cervical cancer.

In specific embodiments, the cancer prevented and/or treated in accordance with the present disclosure is basal cell carcinoma, goblet cell metaplasia, or a malignant glioma, cancer of the liver, breast, lung, prostate, cervix, uterus, colon, pancreas, kidney, stomach, bladder, ovary, or brain.

In specific embodiments, the cancer prevented and/or treated in accordance with the present disclosure include, but are not limited to, cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma ofbone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell(small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In certain embodiments cancers that can be prevented and/or treated in accordance with the present disclosure include, the following: pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, and multiple myeloma.

In certain embodiments, cancers and conditions associated therewith that are prevented and/or treated in accordance with the present disclosure are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer an astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor.

In specific embodiments, the cancer treated in accordance with the present disclosure is an acoustic neuroma, an anaplastic astrocytoma, a glioblastoma multiforme, or a meningioma.

In other specific embodiments, the cancer treated in accordance with the present disclosure is a brain stem glioma, a craniopharyngioma, an ependyoma, a juvenile pilocytic astrocytoma, a medulloblastoma, an optic nerve glioma, primitive neuroectodermal tumor, or a rhabdoid tumor.

Combination Treatments

In certain instances, it is appropriate to administer at least one splice modifying compound described herein in combination with another therapeutic agent.

In one specific embodiment, a splice modifying compound described herein is co-administered with a second therapeutic agent, wherein the splice modifying compound and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, a FOXM1 gene splicing modifier described herein is used in combination with an anti-cancer therapy. In some embodiments, a FOXM1 gene splicing modifier is used in combination with conventional chemotherapy, radiotherapy, hormonal therapy, and/or immunotherapy. In some embodiments, a FOXM1 gene splicing modifier is used in combination with conventional chemotherapeutic agents including alkylating agents (e.g., temozolomide, cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), EGFR inhibitors (e.g., gefitinib, erlotinib, etc.), and the like.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific. In some embodiments, the compounds of the present disclosure are synthesized using the procedures described in Example 1.

Anhydrous solvents and oven-dried glassware were used for synthetic transformations sensitive to moisture and/or oxygen. Yields were not optimized. Reaction times were approximate and were not optimized.

Example 1: (E)-3-(4-(6-(((1R,3s,5S)-8-azabicyclo[3.2.1]octan-3-yl)(methyl)amino)pyridazin-3-yl)-3-hydroxyphenyl)-N-methylacrylamide

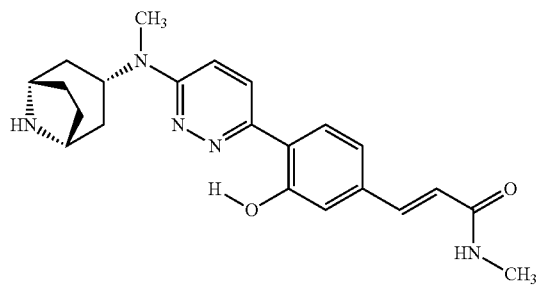 [SMILES: CNC(=O)/C=C/c1ccc(-c2ccc(N(C)[C@@H]3C[C@H]4CC[C@@H](C3)N4)nn2)c(O)c1]

Synthesis of (E)-3-(4-(6-(((1R,3s,5S)-8-azabicyclo[3.2.1]octan-3-yl)(methyl)amino)pyridazin-3-yl)-3-hydroxyphenyl)-N-methylacrylamide

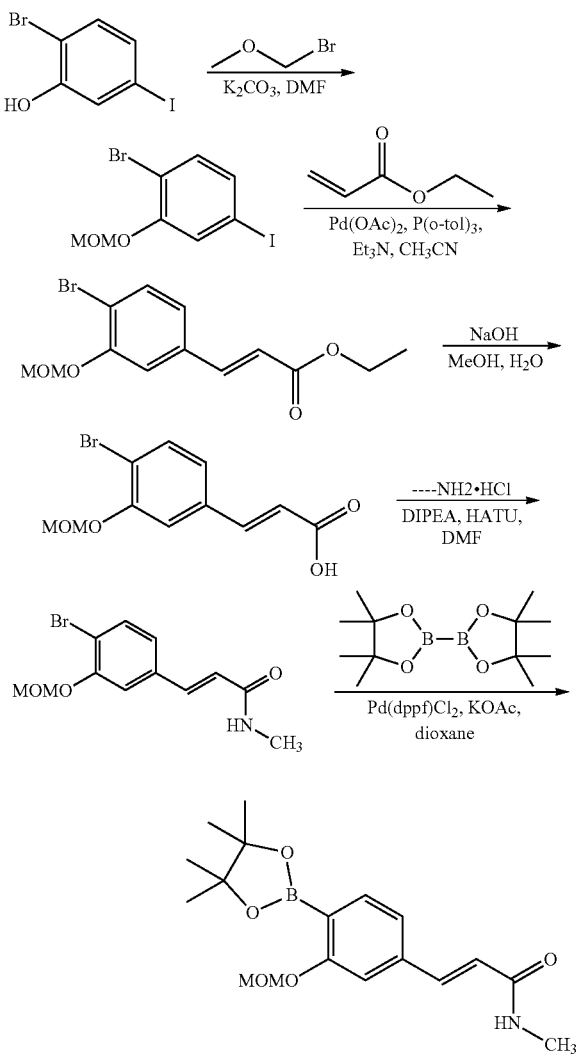

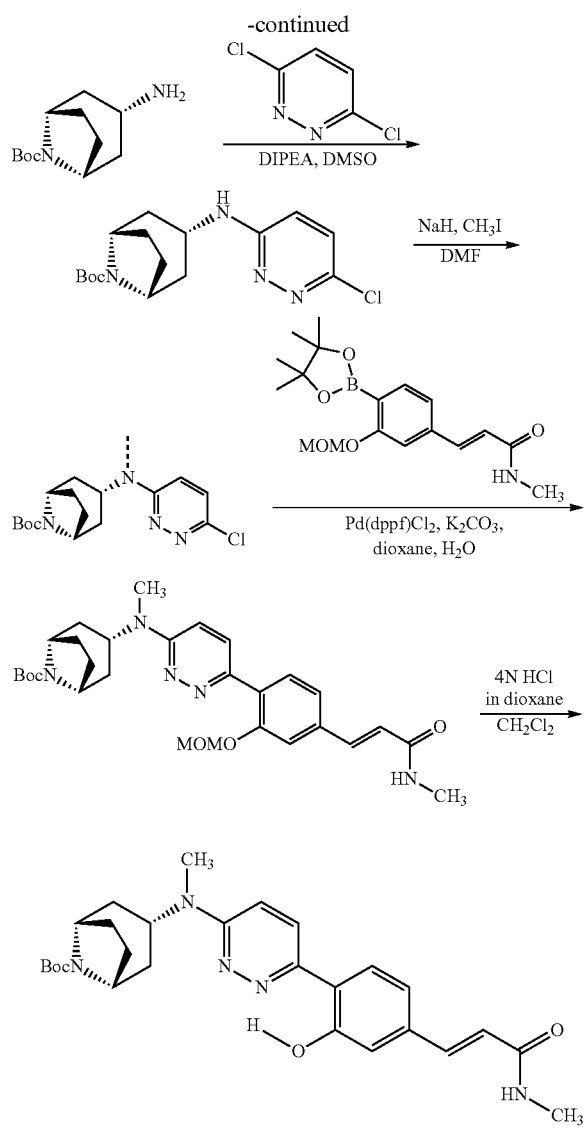

Synthesis of 1-bromo-4-iodo-2-(methoxymethoxy)benzene

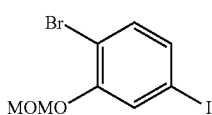

Methoxymethyl bromide (1.25 g, 10 mmol) was added to a stirred solution of 2-bromo-5-iodophenol (1.5 g, 5 mmol) and K₂CO₃ (1.38 g, 10 mmol) in 20 mL of DMF at 0° C. The mixture was stirred at room temperature for 16 h, quenched with 20 mL of H₂O and extracted with ethyl acetate (EtOAc) (20 mL, 3 times). The combined organic solvents were dried over anhydrous Na₂SO₄, concentrated and purified by silica gel column (0-5% EtOAc/petroleum ether) to give 1.45 g of 1-bromo-4-iodo-2-(methoxymethoxy)benzene (79% yield).

Synthesis of (E)-ethyl 3-(4-bromo-3-(methoxymethoxy)phenyl)acrylate

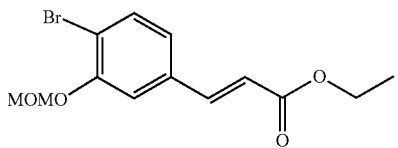

A mixture of 1-bromo-4-iodo-2-(methoxymethoxy)benzene (2 g, 5.8 mmol), ethyl acrylate (580 mg, 5.8 mmol), Pd(OAc)₂ (130 mg, 0.58 mmol), P(o-tol)₃ (530 mg, 1.74 mmol) and TEA (1.17 g, 11.6 mmol) in 10 mL of CH₃CN was purged with nitrogen and sealed. The mixture was stirred at 80° C. for 3 h, concentrated and purified by silica gel chromatography (0-18% EtOAc/petroleum ether) to give 1.6 g of (E)-ethyl 3-(4-bromo-3-(methoxymethoxy)phenyl) acrylate (80% yield). LCMS: m/z 314.8 [M+H]⁺.

Synthesis of (E)-3-(4-bromo-3-(methoxymethoxy) phenyl)acrylic acid

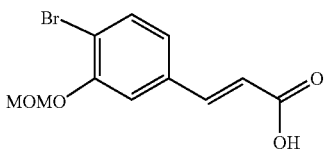

A solution of NaOH (366 mg, 9.16 mmol) in H₂O (15 mL) was added slowly to a stirred solution of (E)-ethyl 3-(4-bromo-3-(methoxymethoxy)phenyl)acrylate (1.44 g, 4.58 mmol) in MeOH (15 mL) at rt. Then the mixture was stirred at 50° C. for 16 h and cooled to rt. HCl (2N aqueous solution) was added to adjust to pH=3. The mixture was extracted with EtOAc (50 mL, 3 times), dried over anhydrous Na₂SO₄, and concentrated to give 1.17 g of (E)-3-(4-bromo-3-(methoxymethoxy)phenyl)acrylic acid (89% yield), which was used directly to next step. LCMS: m/z 286.9 [M+H]⁺.

Synthesis of (E)-3-(4-bromo-3-(methoxymethoxy) phenyl)-N-methylacrylamide

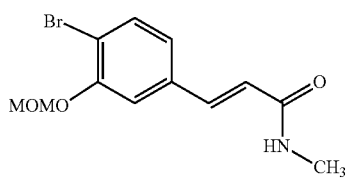

A mixture of (E)-3-(4-bromo-3-(methoxymethoxy)phenyl)acrylic acid (883 mg, 3.08 mmol), methylamine hydrochloride (419 mg, 6.16 mmol), HATU (1.4 g, 3.70 mmol) and DIPEA (1.99 g, 15.4 mmol) in 5 mL of DMF was stirred at rt for 2 h. The mixture was quenched with water (60 mL), extracted with EtOAc (60 mL, 3 times), and concentrated to give 1.08 g of (E)-3-(4-bromo-3-(methoxymethoxy)phenyl)-N-methylacrylamide (89% yield), which was used directly to next step without further purification. LCMS: m/z 301.9 [M+H]⁺.

Synthesis of (E)-3-(3-(methoxymethoxy)-4-(4,4,5,5-tetramethyl-1,3,2-dioxaborolan-2-yl)phenyl)-N-methylacrylamide

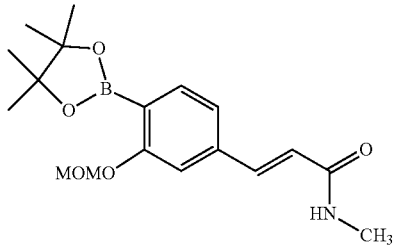

A mixture of (E)-3-(4-bromo-3-(methoxymethoxy)phenyl)-N-methylacrylamide (300 mg, 1.0 mmol.), 4,4,4',4',5,5,5',5'-octamethyl-2,2'-bi(1,3,2-dioxaborolane) (507 mg 2.0 mmol), Pd(dppf)Cl₂ (111 mg, 0.15 mmol) and KOAc (198 mg, 2.0 mmol) in 3 mL of dioxane was degassed and stirred at 100° C. for 3 h. The mixture was cooled to room temperature, concentrated, and purified by silica gel chromatography (0-50% EtOAc/petroleum ether) to give 502 mg of (E)-3-(3-(methoxymethoxy)-4-(4,4,5,5-tetramethyl-1,3,2-dioxaborolan-2-yl)phenyl)-N-methylacrylamide (100% yield). LCMS: m/z 348.1 [M+H]⁺.

Synthesis of tert-butyl 3-(6-chloropyridazin-3-ylamino)-8-azabicyclo[3.2.1]octane-8-carboxylate

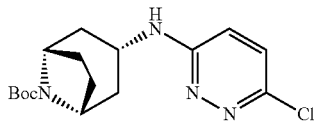 [SMILES: CC(C)(C)OC(=O)N1[C@@H]2CC[C@H]1C[C@H](Nc1ccc(Cl)nn1)C2]

A mixture of tert-butyl 3-amino-8-azabicyclo[3.2.1]octane-8-carboxylate (400 mg, 1.77 mmol), 3,6-dichloropyridazine (489 mg, 3.28 mmol) and DIPEA (652 mg, 5.1 mmol) in 4 mL of DMSO was stirred at 120° C. for 18 h. After cooling to room temperature, the mixture was quenched with 10 mL of water, extracted with EtOAc (20 mL, 3 times). The combined organic solvents were washed with water (10 mL), concentrated, and purified by silica gel column (5-80% EtOAc/petroleum ether) to give 320 mg of tert-butyl 3-(6-chloropyridazin-3-ylamino)-8-azabicyclo[3.2.1]octane-8-carboxylate (53% yield). LCMS: m/z 339.2 [M+H]⁺.

Synthesis of tert-butyl 3-((6-chloropyridazin-3-yl)(methyl)amino)-8-azabicyclo[3.2.1]octane-8-carboxylate

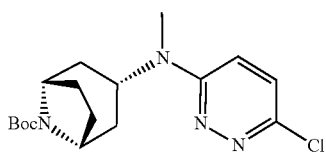

NaH (89 mg, 2.23 mmol, 60% in mineral oil) was added to a stirred solution of tert-butyl 3-(6-chloropyridazin-3-ylamino)-8-azabicyclo[3.2.1]octane-8-carboxylate (300 mg, 0.89 mmol) in 4 mL of DMF at 0° C. After stirring at 0° C. for 40 min, MeI (253 mg, 1.78 mmol) was added. The mixture was then allowed to warm up to room temperature and stirred for 2 h. The mixture was quenched with water (10 mL), extracted with EtOAc (30 mL, 3 times), concentrated, and purified by silica gel column (5-60% EtOAc/petroleum ether) to give 300 mg of tert-butyl 3-((6-chloropyridazin-3-yl)(methyl)amino)-8-azabicyclo[3.2.1]octane-8-carboxylate (96% yield). LCMS: m/z 353.0 [M+H]⁺.

Synthesis of (1R,3s,5S)-tert-butyl 3-((6-(2-(methoxymethoxy)-4-((E)-3-(methylamino)-3-oxo-prop-1-enyl)phenyl)pyridazin-3-yl)(methyl)amino)-8-azabicyclo[3.2.1]octane-8-carboxylate

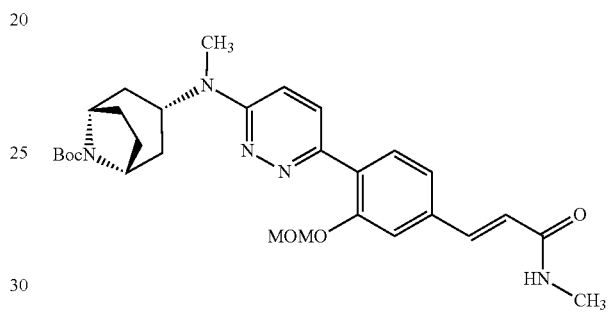

A mixture of (1R,3s,5S)-tert-butyl 3-((6-chloropyridazin-3-yl)(methyl)amino)-8-azabicyclo[3.2.1]octane-8-carboxylate (150 mg, 0.42 mmol), (E)-3-(3-(methoxymethoxy)-4-(4,4,5,5-tetramethyl-1,3,2-dioxaborolan-2-yl)phenyl)-N-methylacrylamide (182 mg, 0.42 mmol), Pd(dppf)Cl₂ (61 mg, 0.084 mmol) and K₂CO₃ (116 mg, 0.84 mmol) in 2 mL of dioxane and 0.25 mL of H₂O was degassed and stirred at 100° C. for 5 h. The mixture was concentrated and purified by silica gel column (0-100% EtOAc/Petroleum ether) to give 117 mg of (1R,3s,5S)-tert-butyl 3-((6-(2-(methoxymethoxy)-4-((E)-3-(methylamino)-3-oxoprop-1-enyl)phenyl)pyridazin-3-yl)(methyl)amino)-8-azabicyclo[3.2.1]octane-8-carboxylate (52% yield). LCMS: m/z 537.8 [M+H]⁺.

Synthesis of (E)-3-(4-(6-(((1R,3s,5S)-8-azabicyclo[3.2.1]octan-3-yl(methyl)amino)pyridazin-3-yl)-3-hydroxyphenyl)-N-methylacrylamide

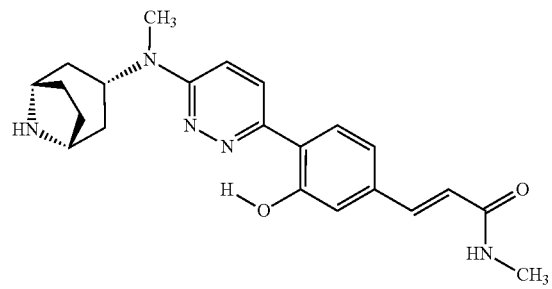 [SMILES: CNC(=O)/C=C/c1ccc(-c2ccc(N(C)[C@@H]3C[C@H]4CC[C@@H](C3)N4)nn2)c(O)c1]

6 mL of HCl in dioxane (4N) was added to a stirred solution of (1R,3s,5S)-tert-butyl 3-((6-(2-

(methoxymethoxy)-4-((E)-3-(methylamino)-3-oxoprop-1-enyl)phenyl)pyridazin-3-yl)(methyl)amino)-8-azabicyclo[3.2.1]octane-8-carboxylate (117 mg, 0.22 mmol) in 3 mL of $CH_2Cl_2$. The mixture was stirred at room temperature for 2 h, concentrated under reduced pressure. The residue was purified by Prep-HPLC to give 35 mg of (E)-3-(4-(6-(((1R,3s,5S)-8-azabicyclo[3.2.1]octan-3-yl(methyl)amino)pyridazin-3-yl)-3-hydroxyphenyl)-N-methylacrylamide (41% yield). $^1$H NMR (400 MHz, DMSO-$d_6$) δ 8.20 (d, J=10.0 Hz, 1H), 8.08 (d, J=4.8 Hz, 1H), 7.91 (d, J=8.1 Hz, 1H), 7.42-7.31 (m, 2H), 7.12 (d, J=8.3 Hz, 2H), 6.63 (d, J=15.8 Hz, 1H), 5.04-4.77 (m, 1H), 3.52 (s, 2H), 2.94 (s, 3H), 2.71 (d, J=4.6 Hz, 3H), 1.80 (s, 6H), 1.60-1.46 (m, 2H). m/z 394.3 $[M+H]^+$.

PHARMACEUTICAL COMPOSITIONS

Example A-1: Parenteral Composition

To prepare a parenteral pharmaceutical composition suitable for administration by injection, 100 mg of a water-soluble salt of a compound of Formula (I), Formula (II), or Formula (III), or a pharmaceutically acceptable solvate thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A-2: Oral Composition

To prepare a pharmaceutical composition for oral delivery, 100 mg of a compound of Formula (I) or Formula (II), or a pharmaceutically acceptable salt or solvate thereof, is mixed with 750 mg of starch. The mixture is incorporated into an oral dosage unit for, such as a hard gelatin capsule, which is suitable for oral administration.

BIOLOGY EXAMPLES

Various cells lines will be treated with a compound of Formula (I), Formula (II), or Formula (III). RNA will then be isolated, cDNA synthesized, and qPCR performed to determine the levels of the A2 and BC FOXM1 variants in the various cell samples.

Materials

Cells to Ct kit: ThermoFisher, AM1728. TaqMan Gene Expression Master Mix: ThermoFisher, 4369542. PPIA probe/primer: ThermoFisher, Hs03045993 gH, VIC-MGB PL.

```
FOXMI A2 probe/primer: IDT DNA:
Forward primer:
ACA GGT GGT GTT TGG TTA CA;

Reverse primer:
AAA TTA AAC AAG CTG GTG ATG GG;
and

Probe:
/56-FAM/AG TTC TTT A/Zen/G TGG CGA TCT GCG AGA

/3IABkFQ/.

FOXMI BC probe/primer: ThermoFisher:
Forward primer:
GAG CTT GCC CGC CAT AG;

Reverse primer:
CTG GTC CTG CAG AAG AAA GAG;
and

Probe:
CCA AGG TGC TGC TAG CTG AGG A (VIC reporter;
MGB-NFQ quencher).

AGS cells: ATCC, CRL-1739:
Grown in F-12K media (ATCC; 30-2004) + 10% FBS
(ATCC; SCRR-30-2020).
A549 cells: ATCC, CCL-185:
Grown in F-12K media (ATCC; 30-2004) + 10% FBS
(ATCC; SCRR-30-2020).
LoVo cells: ATCC CCL-229:
Grown in F-12K media (ATCC; 30-2004) + 10% FBS
(ATCC; SCRR-30-2020).
PANC1 cells:
Grown in DMEM media (ATCC; 30-2002) + 10% FBS
(ATCC; SCRR-30-2020).
U251MG cells:
Grown in EMEM media (ATCC; 30-2003) + 10% FBS
(ATCC; SCRR-30-2020).
```

Protocol

On the day of the experiment, seed a 96-well plate with the cell lines of interest. The cells should be diluted with full growth media to a concentration of $2.0 \times 10^5$ cells/mL and 100 µL of cells added to each well (20,000 cells per well). The cells can be treated with a compound disclosed herein immediately after plating.

Add the compounds disclosed herein to the cell plate using the HP compound dispenser.

a. In the initial experiment, a top concentration of 10 µM and an 8 point 4-fold dilution scheme is used.

b. The stock compounds are made at a concentration of 5 mM, and the DMSO concentration is set to 0.2%.

c. DMSO is used to normalize all the compound-containing wells and the untreated cells.

Incubate the treated cells at 37° C. in a 5% $CO_2$ incubator for the desired amount of time.

a. Plates should be placed in a plastic bag with a wet paper towel to prevent evaporation.

Isolate the RNA using the Cells to Ct kit (ThermoFisher, AM1728).

a. Wash the cells once with 100 µL cold PBS.

b. Prepare the necessary amount of lysis buffer for the number of wells/tubes (49.5 µL lysis buffer+0.5 µL DNase I per well/tube). Ensure that additional reactions are prepared to account for loss during pipetting.

c. Add 50 µL lysis buffer to each well/tube.

d. Mix the lysis reaction by pipetting up and down 5 times. To avoid bubbles, mix only 35 µL of volume.

e. Incubate the plates/tubes at room temperature for 5 minutes.

f. Add 5 µL stop solution directly into each cell lysis reaction.

g. Mix the reaction by pipetting up and down 5 times. To avoid bubbles, mix only 35 µL of volume.

h. Incubate the plates/tubes at room temperature for 2 minutes. Place on ice if the cDNA synthesis is going to performed immediately. Otherwise, store at −80° C.

Perform the cDNA synthesis reactions.

a. Prepare the necessary amount of Reverse Transcription (RT) Master mix. Ensure that additional reactions are prepared to account for loss during pipetting.

| Component | Each reaction |
|---|---|
| 2x RT Buffer | 25 μL |
| 20x RT Enzyme Mix | 2.5 μL |
| Nuclease-free water | 12.5 μL | b. Add 40 μL RT master mix to PCR tubes or plate wells.
c. Add 10 μL of RNA to each tube/well.
d. Run the RT thermal cycler program
   i. Incubate at 37 C for 1 hour, then at 95 C for 5 minutes to deactivate the enzyme.

Perform the qPCR using a QuantStudio 6 instrument (ThermoFisher) and the following cycling conditions. All samples and standards should be analyzed in triplicate.

Cycle 1: 2 minutes at 50° C.

Cycle 2: 10 minutes at 95° C.

Cycle 3 (repeat 40 times): 15 seconds at 95° C., 1 minute at 60° C.

A2 or BC Standard Samples

| Component | Per qPCR well |
|---|---|
| 2x TaqMan Gene Expression MasterMix | 10 μL |
| 40x A2 OR BC probe/primer | 0.5 μL |
| Nuclease-free water | 4.5 μL |
| Standard DNA | 5 μL |

Unknown Sample (A2/BC Quantitation)

| Component | Per qPCR well |
|---|---|
| 2x TaqMan Gene Expression Master Mix | 10 μL |
| 40x A2 probe/primer | 0.5 μL |
| 40x BC probe/primer | 0.5 μL |
| Nuclease-free water | 5 μL |
| Sample DNA | 4 μL |

PPIA Standard Sample

| Component | Per qPCR well |
|---|---|
| 2x TaqMan Gene Expression Master Mix | 10 μL |
| 60x PPIA probe/primer | 0.33 μL |
| Nuclease-free water | 4.67 μL |
| Standard DNA | 5 μL |

Unknown Sample (PPIA Quantitation)

| Component | Per qPCR well |
|---|---|
| 2x TaqMan Gene Expression Master Mix | 10 μL |
| 60x PPIA probe/primer | 0.33 μL |
| Nuclease-free water | 5.67 μL |
| Sample DNA | 4 μL |

The determined A2 and BC quantities can then be used to determine the A2:BC ratio at the various compound concentrations. The PPIA quantities can be used in the normalization to account of cell proliferation effects of the compounds.

Standard construction
FOXM1 A2 STANDARD
G Block sequence (IDT DNA)
GGCTAGCCTCGAGAATTCGTTTTTGGGGAACAGGTGGTGTTTGGTTACAT
GAGTAAGTTCTTTAGTGGCGATCTGCGAGATTTTGGTACACCCATCACCA
GCTTGTTTAATTTTATCTTTCTTTGTTTATCAGCGGCCGCTTCCCTTTAG FOXM1 BC STANDARD
G Block sequence (IDT DNA)
GGCTAGCCTCGAGAATTCGGCGGAAGATGAAGCCACTGCTACCACGGGTC
AGCTCATACCTGGTACCTATCCAGTTCCCGGTGAACCAGTCACTGGTGTT
GCAGCCCTCGGTGAAGGTGCCATTGCCCTGGCGGCTTCCCTCATGAGCT
CAGAGCTTGCCCGCCATAGCAAGCGAGTCCGCATTGCCCCCAAGGTGCTG
CTAGCTGAGGAGGGGATAGCTCCTCTTTCTTCTGCAGGACCAGGGAAAGA
GGAGAAACTCCTGTTTGGAGAAGGGTTTTCTCCTTTGCTTCCAGTTCAGA
CTATCAAGGAGGAAGAAATCCAGCCTGGGGAGGAAATGCCACACTTAGCG
AGACCCATCAAAGTGGAGAGCCCTCCCTTGGAAGAGTGGCCCTCCCCGGC
CCCATCTTTCAAAGAGGAATCATCTCACTCCTGGGAGGATTCGTCCCAAT
CTCCCACCCCAAGACCCAAGAAGTCCTACAGTGGGCTTAGGTCCCCAACC
CGGTGTGTCTCGGAAATGCTTGTGATTCAACACAGGGAGAGGAGGGAGAG
GAGCCGGTCTCGGAGGAAACAGCATCTACTGCCTCCCTGTGTGGATGAGC
CGGAGCTGCTCTTCTCAGAGGGGCCCAGTACTTCCCGCTGGGCCGCAGAG
CTCCCGTTCCCAGCAGACTCCTCTGACCCTGCCTCCCAGCTCAGCTACTC
CCAGGAAGTGGGAGGACCTTTTAAGACACCCATTAAGGAAACGCTGCCCA
TCTCCTCCACCCCGAGCAAATCTGTCCTCCCCAGAACCCCTGAATCCTGG
AGGCTCACGCCCCCAGCCAAAGTAGGGGGACTGGATTTCAGCCCAGTACA
AACCTCCCAGGGTGCCTCTGACCCCTTGCCTGACCCCCTGGGGCTGATGG
ATCTCAGCACCACTCCCTTGCAAAGTGCTCCCCCCCTTGAATCACCGCAA
AGGCTCCTCAGTTCAGAACCCTTAGACCTCATCTCCGTCCCCTTTGGCAA
CTCTTCTCCCTCAGCGGCCGCTTCCCTTTAG PPIA STANDARD
G Block sequence (IDT DNA)
GGCTAGCCTCGAGAATTCGGCCAGGCTCGTGCCGTTTTGCAGACGCCACC
GCCGAGGAAAACCGTGTACTATTAGCCATGGTCAACCCCACCGTGTTCTT
CGACATTGCCGTCGACGGCGAGCCCTTGGGCCGCGTCTCCTTTGAGCTGT
TTGCAGACAAGGTCCCAAAGACAGCAGAAAATTTTCGTGCTCTGAGCACT
GGAGAGAAAGGATTTGGTTATAAGGGTTCCTGCTTTCACAGAATTATTCC
AGGGTTTATGTGTCAGGGTGGTGACTTCACACGCCATAATGGCACTGGTG
GCAAGTCCATCTATGGGGAGAAATTTGAAGATGAGAACTTCATCCTAAAG
CATACGGGTCCTGGCATCTTGTCCATGGCAAATGCTGGACCCAACACAAA
TGGTTCCCGCGGCCGCTTCCCTTTAG The G Blocks are inserted into the pCI-neo mammalian expression vector (Promega) at the EcoRI and NotI restriction sites (in bold) using Infusion cloning technology (Clontech). The plasmids are then purified using standard miniprep (A2 and BC) or maxiprep kits (Macherey Nagel).

Standard Curve Preparation

The dilution of the stock plasmid necessary to make the top standard is calculated at the following website. https:// www.thermofisher.com/us/en/home/brands/thermo-scientific/molecular-biology/molecular-biology-learning-center/molecular-biology-resource-library/thermo-scientific-web-tools/dna-copy-number- calculator.html A top concentration of 200,000,000 copies/µL is prepared in TE buffer. A series of 10-fold dilutions, also in TE, are then made. A total of 5 µL of each standard will be used in a qPCR well to generate to following samples: $10^9$ copies, $10^8$ copies, $10^7$ copies, $10^6$ copies, $10^5$ copies, $10^4$ copies, $10^3$ copies, $10^2$ copies, $10^1$ copies, $10^0$ copies.

Cell Viability and Proliferation

Small molecule splicing modulators were tested in a dose-response assay using different cell lines. Cells were first plated in 96-well plastic tissue culture plates (10,000 cells per well). The cells were treated with 500 nM of SMSM or vehicle alone (DMSO) for 48 hours. Following treatment, the cells were washed with PBS, stained with a crystal violet staining solution, and allowed to dry for 48-72 hrs. After drying, sodium citrate buffer was added to each well and allowed to incubate for 5 min at room temperature. The absorbance was measured at 450 nM using a microplate reader (Biorad; Hercules, Calif.). The relative cell proliferation for each of the cancer cell lines was determined.

To measure cell viability, cells were plated in 96-well plastic tissue culture plates at a density of $5\times10^3$ cells/well. Twenty-four hours after plating, cells were treated with various SMSMs. After 72 hours, the cell culture media were removed and plates were stained with 100 mL/well of a solution containing 0.5% crystal violet and 25% methanol, rinsed with deionized water, dried overnight, and resuspended in 100 mL citrate buffer (0.1 M sodium citrate in 50% ethanol) to assess plating efficiency. Intensity of crystal violet staining, assessed at 570 nm and quantified using a Vmax Kinetic Microplate Reader and Softmax software (Molecular Devices Corp., Menlo Park, Calif.), were directly proportional to cell number. Data were normalized to vehicle-treated cells and were presented as the mean±SE from representative experiments. SMSMs that are effective were determined for various cells lines.

Figure 2:
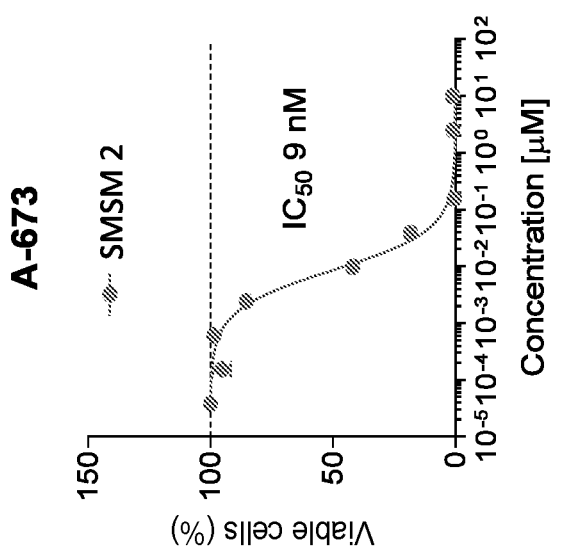
FIG. 2 depicts a graph of viable A-673 cells when incubated with the indicated concentrations of SMSM-2.
Figure 3:
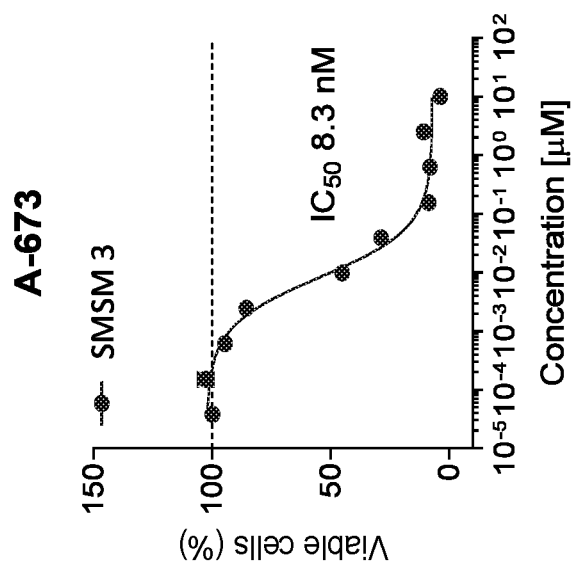
FIG. 3 depicts a graph of viable A-673 cells when incubated with the indicated concentrations of SMSM-3.
Figure 4:
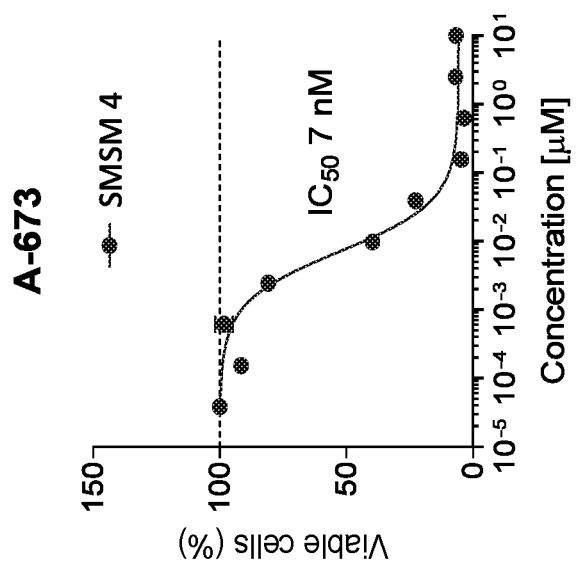
FIG. 4 depicts a graph of viable A-673 cells when incubated with the indicated concentrations of SMSM-4.
Figure 5:
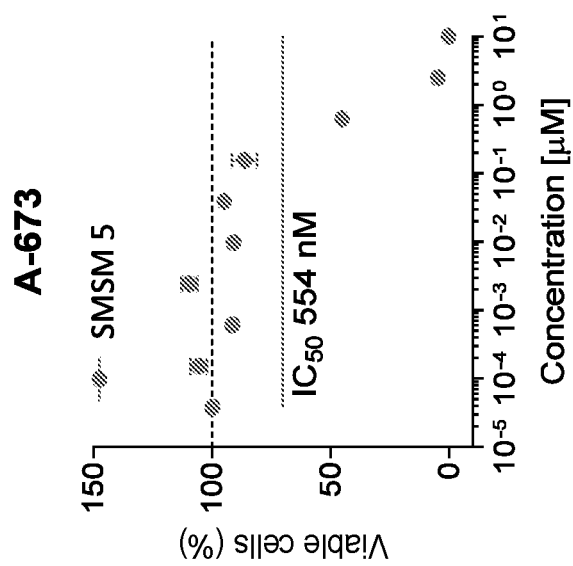
FIG. 5 depicts a graph of viable A-673 cells when incubated with the indicated concentrations of SMSM-5.
Figure 6:
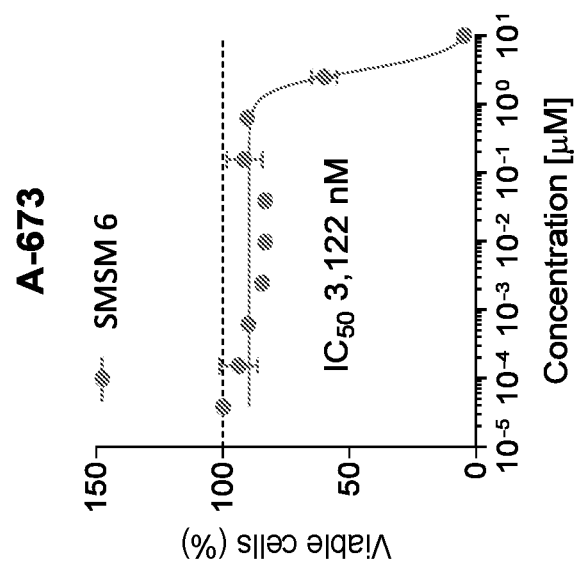
FIG. 6 depicts a graph of viable A-673 cells when incubated with the indicated concentrations of SMSM-6.
Figure 7:
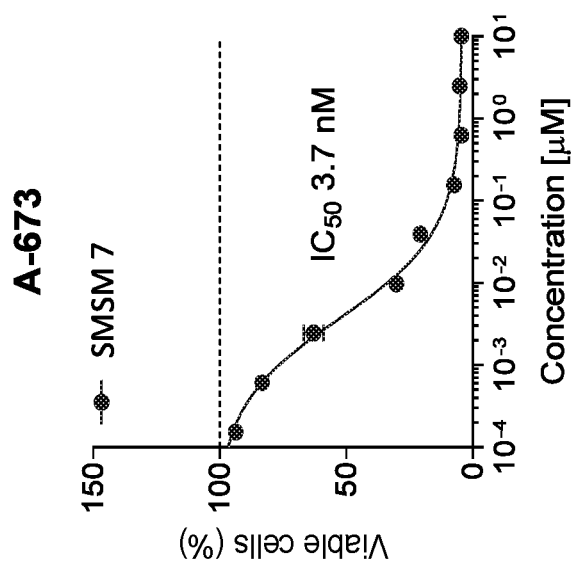
FIG. 7 depicts a graph of viable A-673 cells when incubated with the indicated concentrations of SMSM-7.
Figure 8:
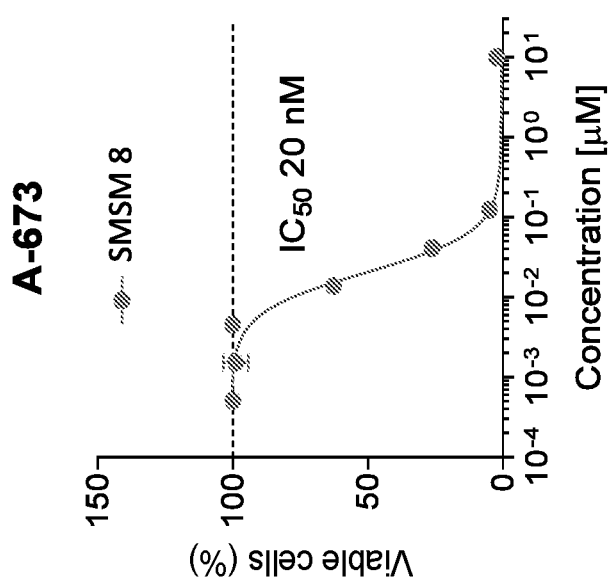
FIG. 8 depicts a graph of viable A-673 cells when incubated with the indicated concentrations of SMSM-8.
Figure 9:
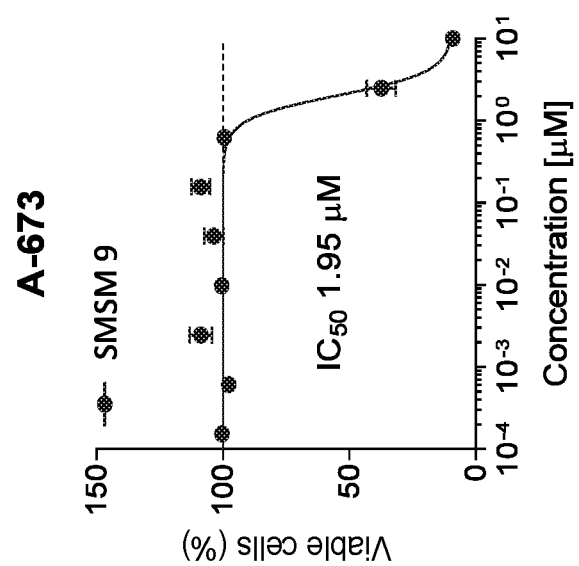
FIG. 9 depicts a graph of viable A-673 cells when incubated with the indicated concentrations of SMSM-9.
Figure 10:
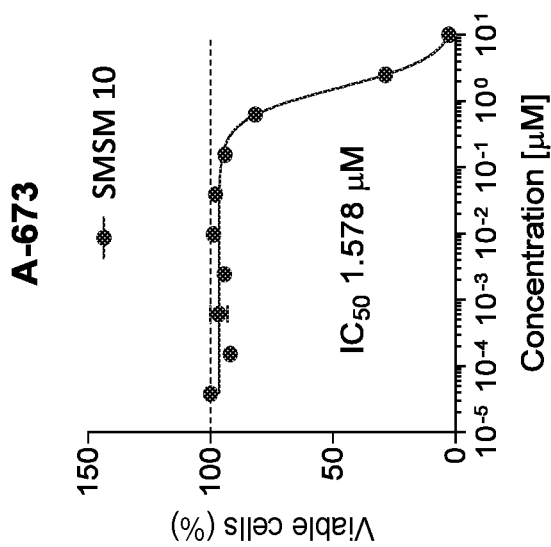
FIG. 10 depicts a graph of viable A-673 cells when incubated with the indicated concentrations of SMSM-10.
Figure 11:
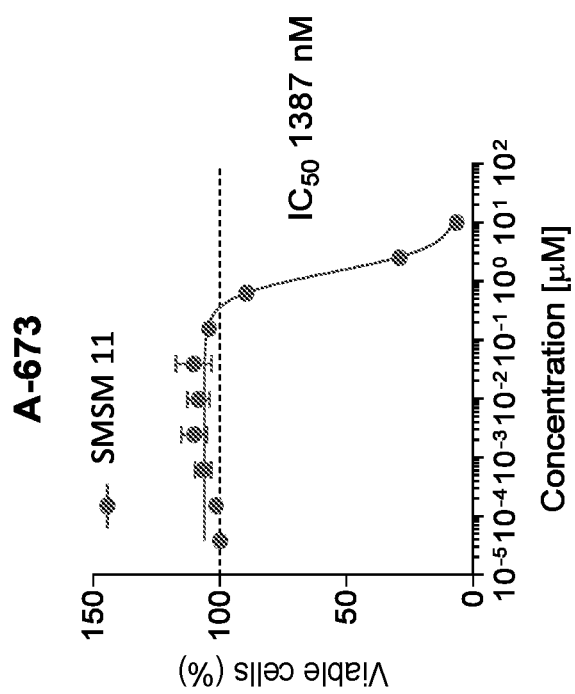
FIG. 11 depicts a graph of viable A-673 cells when incubated with the indicated concentrations of SMSM-11.
Figure 12:
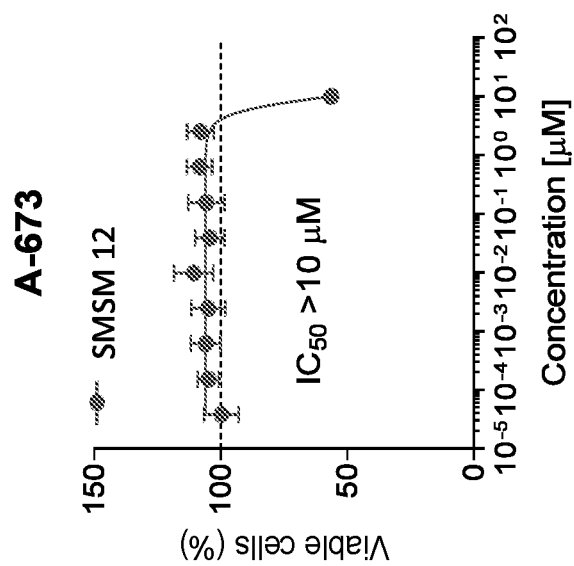
FIG. 12 depicts a graph of viable A-673 cells when incubated with the indicated concentrations of SMSM-12.
Figure 13:
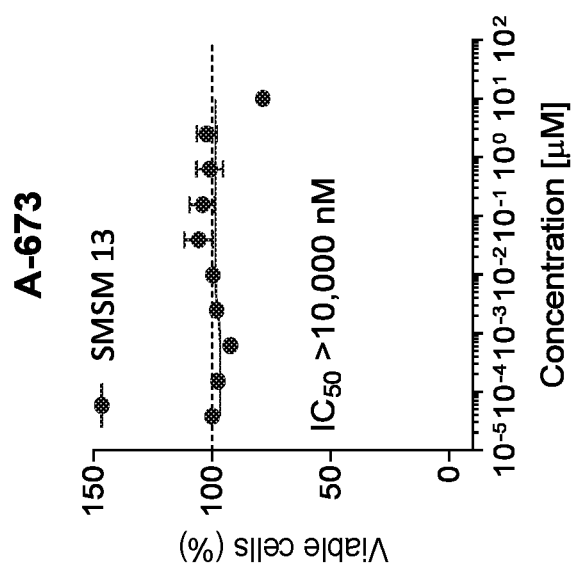
FIG. 13 depicts a graph of viable A-673 cells when incubated with the indicated concentrations of SMSM-13.
Figure 14:
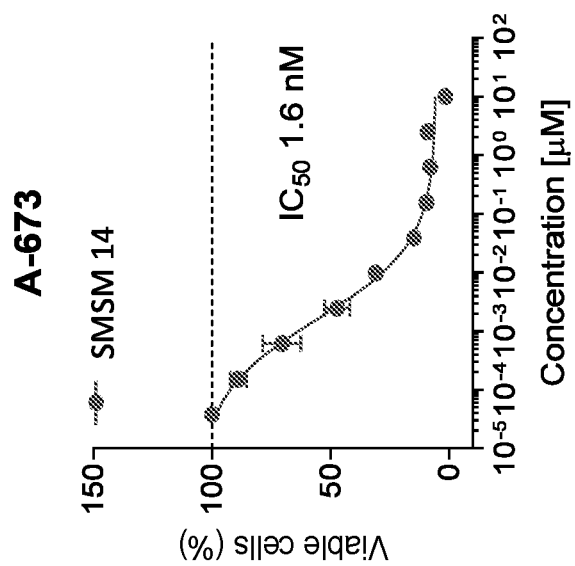
FIG. 14 depicts a graph of viable A-673 cells when incubated with the indicated concentrations of SMSM-14.
Figure 15:
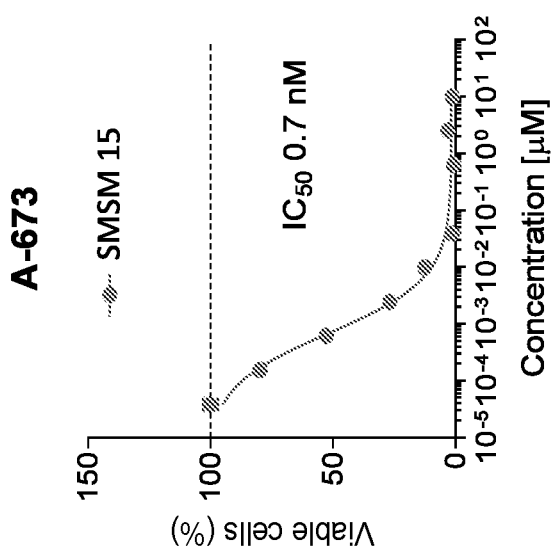
FIG. 15 depicts a graph of viable A-673 cells when incubated with the indicated concentrations of SMSM-15.
Figure 16:
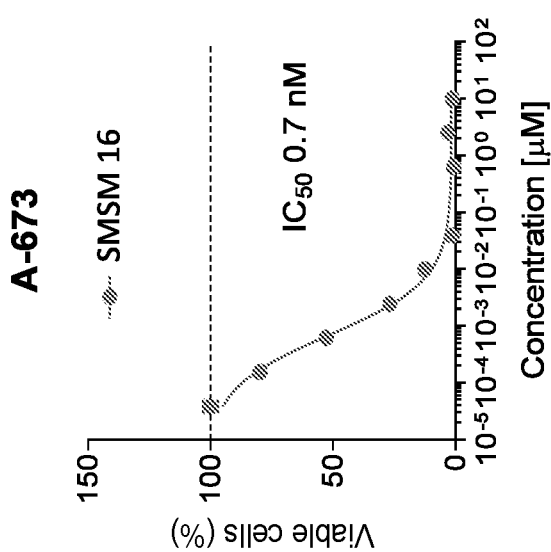
FIG. 16 depicts a graph of viable A-673 cells when incubated with the indicated concentrations of SMSM-16.
Figure 17:
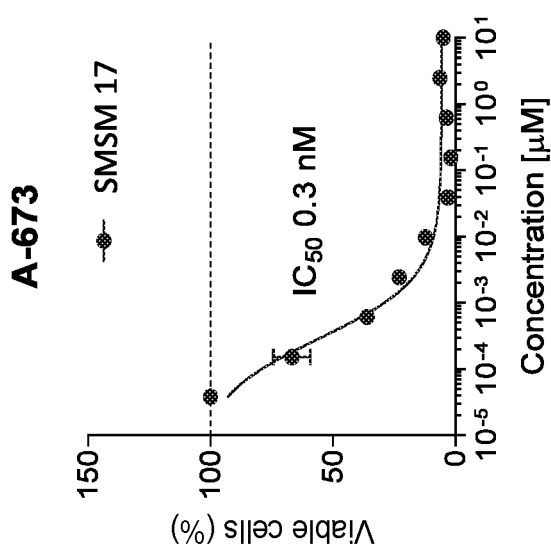
FIG. 17 depicts a graph of viable A-673 cells when incubated with the indicated concentrations of SMSM-17.
Figure 18:
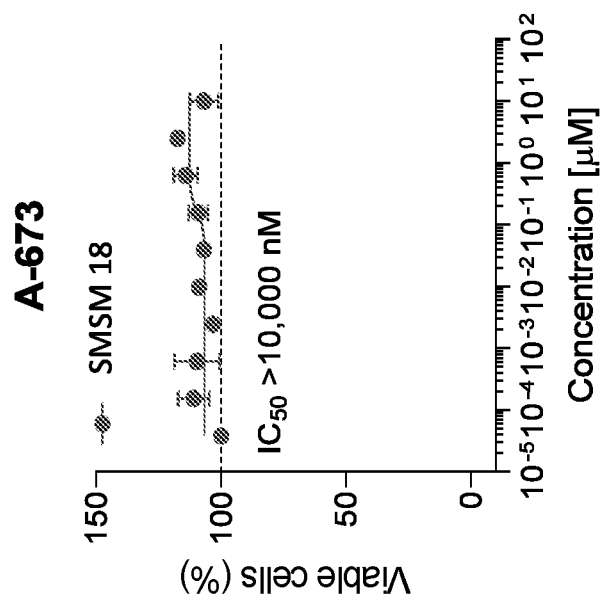
FIG. 18 depicts a graph of viable A-673 cells when incubated with the indicated concentrations of SMSM-18.
Figure 19:
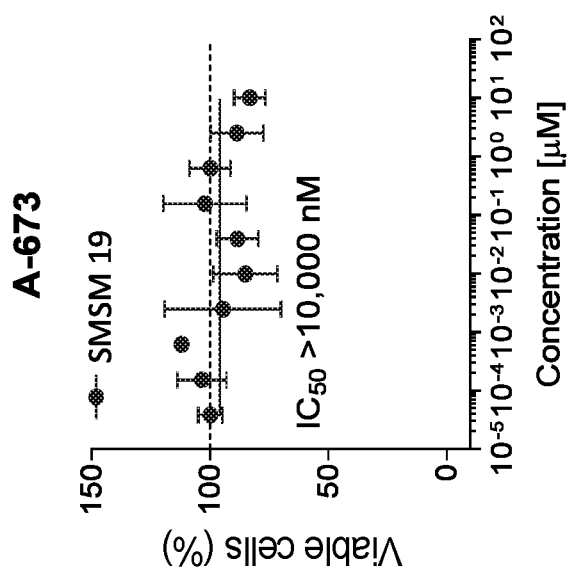
FIG. 19 depicts a graph of viable A-673 cells when incubated with the indicated concentrations of SMSM-19.
Figure 20:
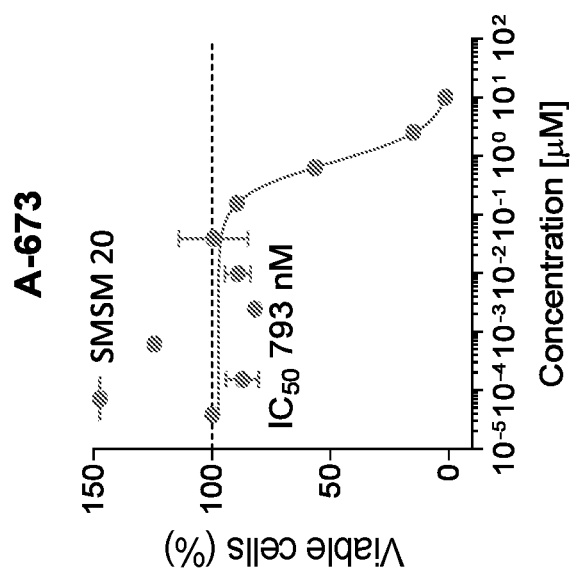
FIG. 20 depicts a graph of viable A-673 cells when incubated with the indicated concentrations of SMSM-20.
Figure 21:
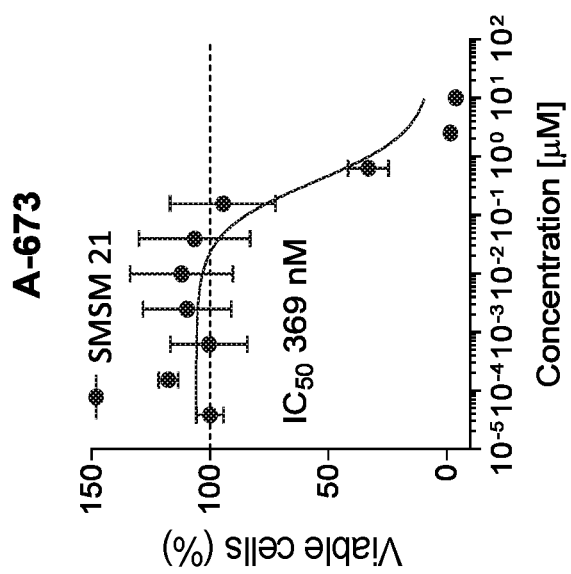
FIG. 21 depicts a graph of viable A-673 cells when incubated with the indicated concentrations of SMSM-21.
Figure 22:
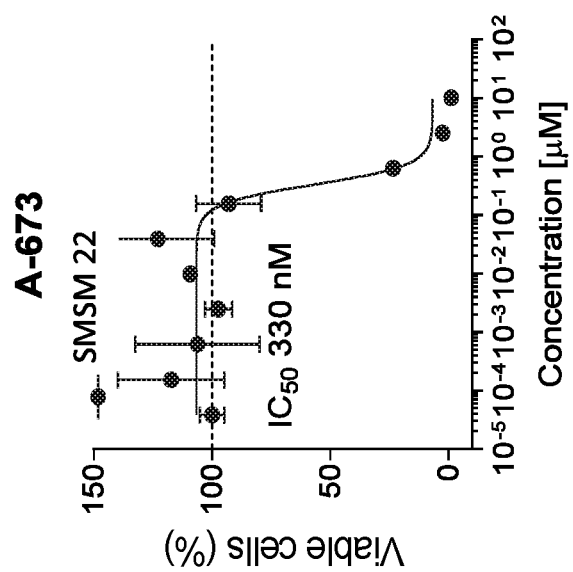
FIG. 22 depicts a graph of viable A-673 cells when incubated with the indicated concentrations of SMSM-22.
Figure 23:
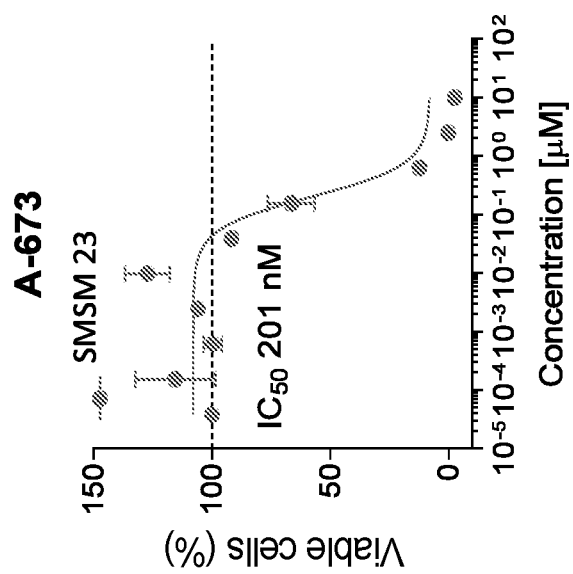
FIG. 23 depicts a graph of viable A-673 cells when incubated with the indicated concentrations of SMSM-23.

Small molecule splicing modulators were tested in a dose-response assay using A673 cells. A673 cells were first plated in 96-well plastic tissue culture plates (10,000 cells per well). The cells were treated with vehicle alone (DMSO), or increasing concentrations of SMSM compounds for 72 h. Following treatment, cell proliferation was determined using a crystal violet assay. The relative cell proliferation at each concentration was determined. Exemplary results are shown in the Table 6 and FIGS. 1-23.

TABLE 6

Patient FOXM1 Data

| Compound Number | IC$_{50}$ Proliferation (nM) |
| --- | --- |
| SMSM 1 | 91 |
| SMSM 2 | 9 |
| SMSM 3 | 8.3 |
| SMSM 4 | 7 |
| SMSM 5 | 554 |
| SMSM 6 | 3122 |
| SMSM 7 | 3.7 |
| SMSM 8 | 20 |
| SMSM 9 | 1950 |
| SMSM 10 | 1578 |
| SMSM 11 | 1387 |
| SMSM 12 | >1000 |
| SMSM 13 | >1000 |
| SMSM 14 | 1.6 |
| SMSM 15 | 0.7 |

TABLE 6-continued

Patient FOXM1 Data

| Compound Number | IC$_{50}$ Proliferation (nM) |
| --- | --- |
| SMSM 16 | 0.2 |
| SMSM 17 | 0.3 |
| SMSM 18 | >1000 |
| SMSM 19 | >1000 |
| SMSM 20 | 793 |
| SMSM 21 | 369 |
| SMSM 22 | 330 |
| SMSM 23 | 201 |

Example B-1: Monitoring Expression Levels of FOXM1 Splice Variants Using Real-Time Quantitative PCR Human fibroblasts are plated at 10,000 cells/well in 200 µL DMEM with GlutaMAX and 10% FBS in 96-well plates in a cell culture incubator (37° C., 5% CO2, 100% relative humidity). Cells are then treated with compounds of Formula (I), Formula (II), or Formula (III) at different concentrations (0.1-300 nM, each in 0.5% DMSO) in triplicate for 24 hours. RNA extraction is performed as per instructions mentioned in the Ambion® Cells-to-CT™ Kits from Applied Biosystems®. RNA samples are frozen at −20° C. until further analysis. Relative expression levels of full-length FOXM1 (FOXM1_FL) or FOXM1 lacking exon VIIa (FOXM1_ΔVIIa) with GAPDH for internal control, is measured using one-step multiplex reverse transcription-polymerase chain reaction (RT-PCR). TaqMan® FAM probes are used for relative quantitation of FOXM1_FL or FOXM1_ΔVIIa expression levels and TaqMan® VIC probes are used for relative quantitation of human GAPDH levels. The fidelity of the amplification methods is determined using the ΔΔCt relative quantification method for quantitative PCR.

Compounds Induce Alternative Splicing of FOXM1 Towards Full-Length FOXM1

To investigate an effect on splicing of FOXM1, human fibroblasts are treated for 24 hours with compounds of the Formula (I), Formula (II), or Formula (III) in dose response, and analyzed by RT-qPCR for presence of mRNA including (FOXM1_FL) or excluding the exon VIIa (FOXM1_ΔVIIa). Compounds of Formula (I), Formula (II), or Formula (III) increase expression of the FOXM1_FL mRNA. Correspondingly, the mRNAs for FOXM1_ΔVIIa declined. The data demonstrate that upregulation of FOXM1_FL with downregulation of FOXM1_ΔVIIa by treatment with compounds of present disclosure are directly correlated, indicating an effect of the compounds on alternative splicing of FOXM1. The resulting concentration dependence curves of the FOXM1_ΔVIIa splice variant are fitted to a Hill binding equation to yield IC50 values. Taken together, the data underline a splicing modifying activity in the FOXM1 gene. This may result in arrest of cell cycle and induction of apoptosis, as the FOXM1_FL variant created by compound treatment is functionally inactive, and therefore will antagonize the pro-proliferating effect of functional FOXM1 (H. Ye, T. F. Kelly, U. Samadani, L. Lim, S. Rubio, D. G. Overdier, K. A. Roebuck, R. H. Costa, Mol. Cell Biol. 17 (1997) 1626-1641).

The examples and embodiments described herein are for illustrative purposes only and various modifications or changes suggested to persons skilled in the art are to be included within the spirit and purview of this application and scope of the appended claims.

What is claimed is:

1. A compound of Formula (II), or a pharmaceutically acceptable salt thereof:

Formula (II)

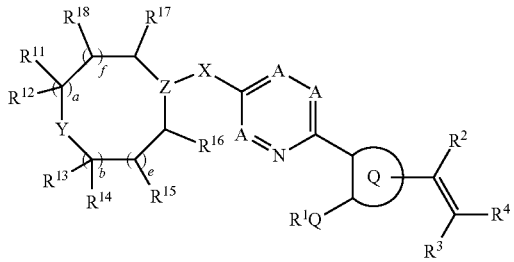

wherein, is

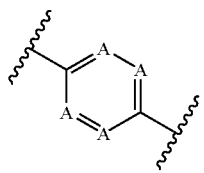

is

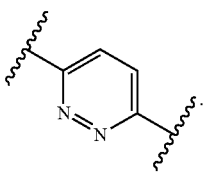 [SMILES: *c1ccc(*)nn1]

is

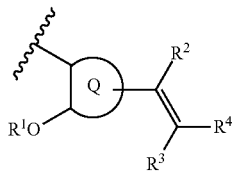

is wherein each $R^Q$ is independently selected from cyano, halogen, hydroxy, $C_1$-$C_6$alkyl, $C_2$-$C_6$alkenyl, $C_2$-$C_6$alkynyl, $C_1$-$C_6$alkoxy, $C_3$-$C_7$cycloalkyl, $C_2$-$C_8$heterocycloalkyl, heteroaryl, $C_2$-$C_{10}$heterocycloalkyl-$C_1$-$C_6$alkyl, $C_1$-$C_6$alkyl-aryl, $C_1$-$C_6$alkyl-$C_2$-$C_{10}$heterocycloalkyl, $C_1$-$C_6$alkyl-heteroaryl, $C_1$-$C_6$alkoxy-aryl, $C_1$-$C_6$alkoxy-$C_2$-$C_{10}$heterocycloalkyl, and $C_1$-$C_6$alkoxy-heteroaryl, wherein each of the alkyl, alkenyl, alkynyl, alkoxy, cycloalkyl, heterocycloalkyl, aryl, and heteroaryl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —SC$_1$-C$_4$alkyl, —S(=O)C$_1$-C$_4$alkyl, —S(=O)$_2$C$_1$-C$_4$alkyl, and oxo;

n is 0, 1, 2, or 3;

X is absent or —NR$^7$—;

each $R^1$ and $R^5$ is independently H, D, $C_1$-$C_6$alkyl, $C_1$-$C_6$haloalkyl, $C_1$-$C_6$heteroalkyl, $C_3$-$C_8$cycloalkyl, $C_2$-$C_7$heterocycloalkyl, aryl, or heteroaryl, wherein each of the alkyl, haloalkyl, heteroalkyl, cycloalkyl, heterocycloalkyl, aryl and heteroaryl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —SC$_1$-C$_4$alkyl, —S(=O)C$_1$-C$_4$alkyl, —S(=O)$_2$C$_1$-C$_4$alkyl, and oxo;

each $R^2$ and $R^3$ is independently H, D, halogen, $C_1$-$C_6$alkyl, $C_1$-$C_6$haloalkyl, aryl, monocyclic heteroaryl, —OR$^5$, —N(R$^5$)$_2$, —CH$_2$OR$^5$, —C(=O)R$^5$, —C(=O)OR$^5$, —C(=O)N(R$^5$)$_2$, —S(=O)R$^5$, —S(=O)$_2$R$^5$, or —NR$^5$C(=O)R$^5$, wherein each of the alkyl, haloalkyl, aryl and heteroaryl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

R$^4$ is —C(=O)R$^5$, —C(=O)OR$^5$, —C(=O)N(R$^6$)$_2$, —C=(O)N(OR$^5$)(R$^5$), —P(=O)(R$^6$)$_2$, —P(=O)(R$^6$)N(R$^6$)$_2$, —S(=O)R$^6$, —S(=O)$_2$R$^6$, —S(=O)(=NR$^5$)R$^5$, —N(R$^6$)C(=O)R$^6$, N(R$^6$)S(=O)R$^6$, N(R$^6$)S(=O)$_2$R$^6$, —C(=O)N(R$^6$)S(=O)$_2$R$^6$, —N(R$^6$)C(=O)N(R$^6$)$_2$, cycloalkyl, C$_2$-C$_{10}$heterocycloalkyl, aryl, or heteroaryl, wherein each of the cycloalkyl, heterocycloalkyl, aryl and heteroaryl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

each R$^6$ is independently H, D, C$_1$-C$_6$alkyl, C$_1$-C$_6$haloalkyl, aryl, monocyclic heteroaryl, —OR$^5$, —N(R$^5$)$_2$, —CH$_2$OR$^5$, —C(=O)R$^5$, —C(=O)OR$^5$, —C(=O)N(R$^5$)$_2$, —S(=O)R$^5$, —S(=O)$_2$R$^5$, or —NR$^5$C(=O)R$^5$, wherein each of the alkyl, haloalkyl, aryl and heteroaryl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo; or two R$^6$ groups on the same nitrogen atom are taken together with the nitrogen atom to which they are attached to form C$_2$-C$_{10}$heterocycloalkyl, which is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

R$^7$ is H or C$_1$-C$_6$alkyl, wherein the alkyl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

Y is NR or CR$^5$R$^6$;

Z is N or CR$^6$;

R is selected from the group consisting of H, C$_1$-C$_6$alkyl, C$_1$-C$_6$fluoroalkyl, C$_1$-C$_6$heteroalkyl, C$_3$-C$_8$cycloalkyl, C$_2$-C$_7$heterocycloalkyl, aryl, and heteroaryl, wherein each of the alkyl, fluoroalkyl, and heteroalkyl is unsubstituted or substituted with hydroxy, amino, mono-C$_1$-C$_6$alkylamino or di-C$_1$-C$_6$alkylamino; and wherein each of the cycloalkyl, heterocycloalkyl, aryl and heteroaryl is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

R$^{11}$, R$^{12}$, R$^{13}$, R$^{14}$, R$^{15}$, R$^{16}$, R$^{17}$, and R$^{18}$ are each independently selected from the group consisting of H, F, OR$^5$, C$_1$-C$_6$alkyl, C$_1$-C$_6$fluoroalkyl, and C$_1$-C$_6$heteroalkyl, wherein each of the alkyl, fluoroalkyl, and heteroalkyl is unsubstituted or substituted with hydroxy, amino, methoxy, mono-C$_1$-C$_6$akylamino or di-C$_1$-C$_6$akylamino; or R$^{11}$ and R$^{13}$ are taken together to form C$_1$-C$_3$alkylene group or C$_1$-C$_3$heteroalkylene group, each of which is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo; or R$^{11}$ and R$^{15}$ are taken together to form C$_1$-C$_3$alkylene group, which is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo; or R$^{15}$ and R$^{18}$ are taken together to form a bond or C$_1$-C$_3$alkylene group, which is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

R$^{16}$ and R$^{17}$ are taken together to form C$_1$-C$_3$alkylene group, which is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$ alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo;

R$^{13}$ and R$^{14}$ are taken together with the carbon atom to which they are attached, to form a spirocyclic C$_3$-C$_8$cycloalkyl; or when Z is CR$^6$, then R$^{17}$ and R$^6$ are taken together to form a bond or C$_1$-C$_3$alkylene group, which is unsubstituted or substituted with one or more substituents selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, —S(=O)$_2$C$_1$-C$_4$alkyl, and oxo; or when X is —NR$^7$— and Z is CR$^6$, then R$^7$ and R$^6$ are taken together with the intervening atoms to which they are attached to form a monocyclic 4, 5, or 6-membered ring; or when X is —NR$^7$—, then R$^7$ and R$^{16}$ are taken together with the intervening atoms to which they are attached to form a monocyclic 4, 5, or 6-membered ring;

a and b are each independently selected from 0, 1, 2, or 3; and e and f are each independently selected from 0, 1, or 2;

wherein each of the heterocycloalkyl is independently monocyclic or bicyclic and contains 1-4 N atoms, 0-2 O atoms, 0-2 P atoms, and 0-1 S atoms in the ring, wherein each of the heteroaryl is independently 5 or 6 membered monocyclic heteroaryl that contains 1-4 N atoms, 0-1 O atoms and 0-1 S atoms, and wherein each of the heteroalkyl independently contains one or more skeletal atoms selected from O, N and S, and is attached to the rest of the molecule at a carbon or heteroatom of the heteroalkyl.

2. The compound of claim 1, or a pharmaceutically acceptable salt thereof, wherein:

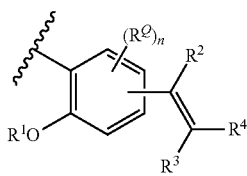

is

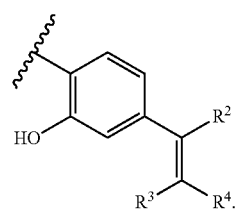

3. The compound of claim 1, or a pharmaceutically acceptable salt thereof, wherein X is —NR$^7$—.

4. The compound of claim 3, or a pharmaceutically acceptable salt thereof, wherein R$^7$ is C$_1$-C$_6$alkyl which is unsubstituted or substituted with one or more halogens.

5. The compound of claim 4, or a pharmaceutically acceptable salt thereof, wherein R$^7$ is —CH$_3$, —CH$_2$CH$_2$F, or —CF$_3$.

6. The compound of claim 1, or a pharmaceutically acceptable salt thereof, wherein Y is NR and

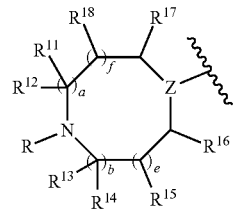

is

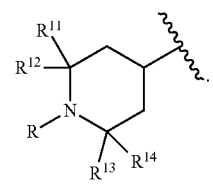

7. The compound of claim 6, or a pharmaceutically acceptable salt thereof, wherein

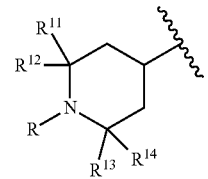

is

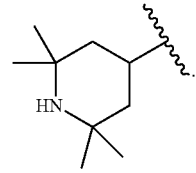 [SMILES: *C1CC(C)(C)NC(C)(C)C1]

8. The compound of claim 1, or a pharmaceutically acceptable salt thereof, wherein Y is NR and

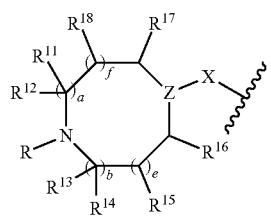

is

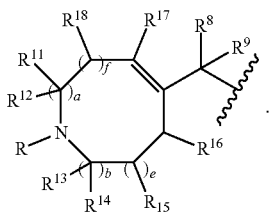

9. A pharmaceutical composition comprising a compound of claim 1, or a pharmaceutically acceptable salt thereof, and at least one pharmaceutically acceptable excipient.

10. A combination comprising a therapeutically effective amount of a compound of claim 1, or a pharmaceutically acceptable salt thereof, and one or more therapeutically active co-agents.

11. The compound of claim 1, or a pharmaceutically acceptable salt thereof, wherein:
Y is NR and

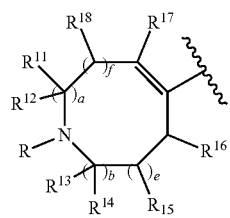

is

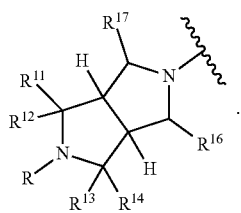

12. The compound of claim 11, or a pharmaceutically acceptable salt thereof, wherein:

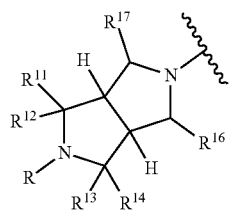

is

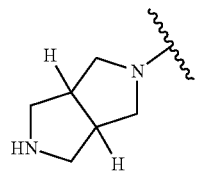

13. The compound of claim 1, or a pharmaceutically acceptable salt thereof, wherein the compound has the structure of Formula (IId):

Formula(IId)

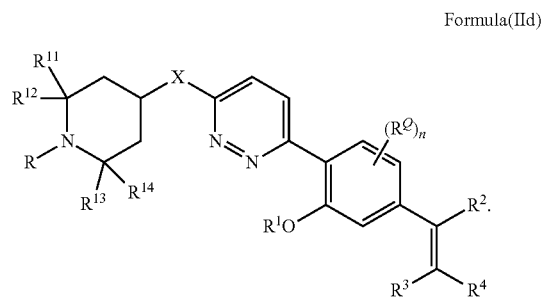

Formula (IId).

14. The compound of claim 1, or a pharmaceutically acceptable salt thereof, wherein the compound has the structure of Formula (IIe):

Formula(IIe)

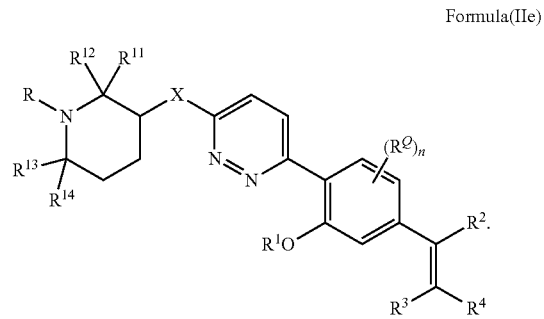

Formula (IIe).

15. The compound of claim 1, or a pharmaceutically acceptable salt thereof, wherein each $R^2$ and $R^3$ is independently H, D, halogen, or $C_1$-$C_6$alkyl.

16. The compound of claim 1, or a pharmaceutically acceptable salt thereof, wherein each $R^2$ and $R^3$ is hydrogen, $R^2$ is hydrogen and $R^3$ is $CH_3$, or $R^2$ is $CH_3$ and $R^3$ is hydrogen.

17. The compound of claim 1, or a pharmaceutically acceptable salt thereof, wherein $R^4$ is —C(=O)OH, —C(=O)NH$_2$, —C(=O)NHCH$_3$, —C(=O)N(CH$_3$)$_2$, —C(=O)NH(OH), —C(=O)NH(OCH$_3$), —C(=O)N(CH$_3$)OH, C(=O)N(CH$_3$)OCH$_3$, —N(C(=O)CH$_3$)OH, —P(=O)(OH)$_2$, —PH(=O)(OH), —S(=O)$_2$OH, —S(=O)OH, —S(=O)$_2$CH$_3$, —S(=O)CH$_3$, —S(=O)$_2$NH$_2$, —S(=O)NH$_2$, —S(=O)$_2$NH(CH$_3$), —S(=O)NH(CH$_3$), —S(=O)$_2$N(CH$_3$)$_2$, —S(=O)N(CH$_3$)$_2$, —S(=O)(=NH)CH$_3$, —S(=O)(=NCH$_3$)CH$_3$, —NH(S(=O)$_2$CH$_3$), —C(=O)NH(S(=O)$_2$CH$_3$), —C(=O)NH(S(=O)$_2$N(CH$_3$)$_2$), or —NHC(=O)NH(C(=O)CH$_3$).

18. The compound of claim 1, or a pharmaceutically acceptable salt thereof, wherein R⁴ is

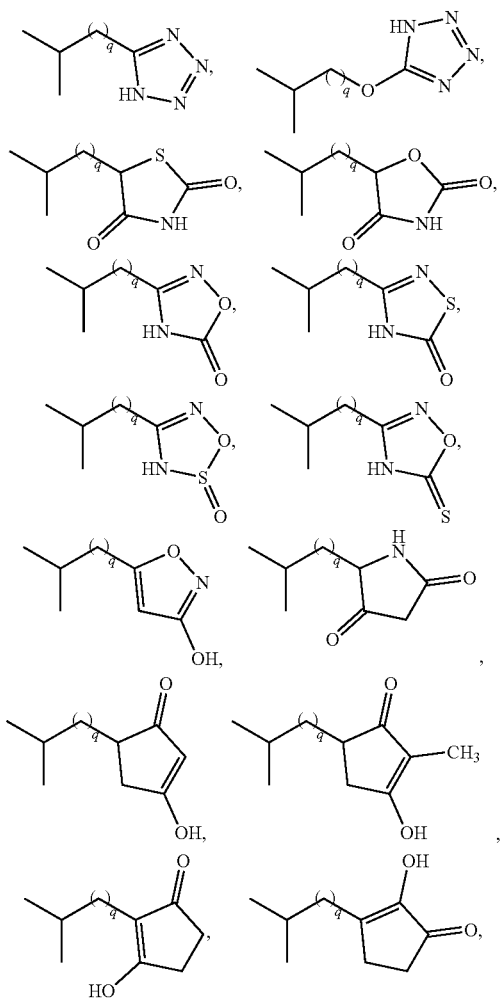
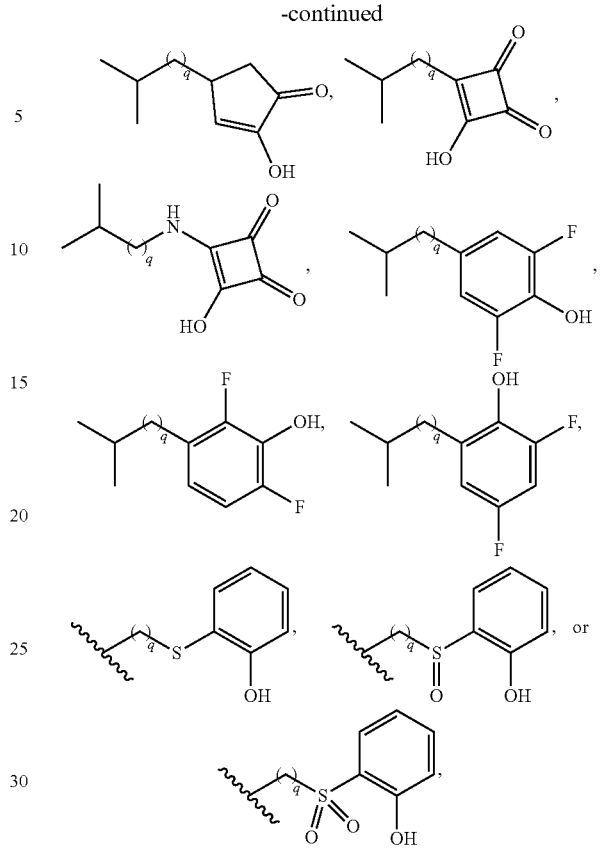

wherein q is 0, 1, or 2.

19. The compound of claim 1, or a pharmaceutically acceptable salt thereof, wherein Y is NR, and R is selected from the group consisting of H, $C_1$-$C_6$alkyl, substituted or unsubstituted $C_1$-$C_6$fluoroalkyl, and $C_1$-$C_6$heteroalkyl.

20. The compound of claim 1, or a pharmaceutically acceptable salt thereof, wherein each $R^Q$ is hydrogen.

* * * * *